(12) United States Patent
Fukui et al.

(10) Patent No.: US 7,795,363 B2
(45) Date of Patent: Sep. 14, 2010

(54) POLYMER HAVING A SULFONIC GROUP OR A SULFONATE GROUP AND AN AMIDE GROUP AND METHOD OF PRODUCING SAME

(75) Inventors: Tatsuki Fukui, Yamato (JP); Takashi Kenmoku, Mishima (JP); Ako Kusakari, Tokyo (JP); Chieko Mihara, Isehara (JP); Tetsuya Yano, Atsugi (JP); Norikazu Fujimoto, Susono (JP)

(73) Assignee: Canon Kabushiki Kaisha, Tokyo (JP)

( * ) Notice: Subject to any disclaimer, the term of this patent is extended or adjusted under 35 U.S.C. 154(b) by 973 days.

(21) Appl. No.: 10/557,413

(22) PCT Filed: May 11, 2005

(86) PCT No.: PCT/JP2005/009015

§ 371 (c)(1), (2), (4) Date: Aug. 15, 2006

(87) PCT Pub. No.: WO2005/108441

PCT Pub. Date: Nov. 17, 2005

(65) Prior Publication Data
US 2007/0059627 A1    Mar. 15, 2007

(30) Foreign Application Priority Data
May 12, 2004    (JP) ............................. 2004-142882

(51) Int. Cl.
*C08F 26/02* (2006.01)

(52) U.S. Cl. ........................................ 526/288; 558/57

(58) Field of Classification Search ............... 526/288; 558/57
See application file for complete search history.

(56) References Cited

U.S. PATENT DOCUMENTS

| | | | |
|---|---|---|---|
| 3,902,906 A | 9/1975 | Iwama et al. | 96/115 R |
| 3,956,354 A | 5/1976 | Schroeck | 558/49 |
| 4,883,735 A | 11/1989 | Watanabe | 430/109 |
| 5,128,419 A | 7/1992 | Fong et al. | 525/351 |
| 5,183,720 A | 2/1993 | Kato et al. | 430/96 |
| 5,302,192 A | 4/1994 | McLearie et al. | 106/18.33 |

FOREIGN PATENT DOCUMENTS

EP    0079157    5/1983

(Continued)

OTHER PUBLICATIONS

English translation of JP 2003-286322 pubhlished Oct. 2003.*

(Continued)

*Primary Examiner*—Mark F Huff
*Assistant Examiner*—Peter L Vajda
(74) *Attorney, Agent, or Firm*—Fitzpatrick, Cella, Harper & Scinto

(57) ABSTRACT

A polymer is provided in which a sulfonic group or a derivative thereof is introduced. The polymer includes a unit represented by the following chemical formula (1): wherein R represents -$A_1$-$SO_2R_1$; $A_1$ is selected from an alkylene group, a heterocyclic ring, an aromatic ring; and —$SO_2R_1$ is a sulfonic group or of a derivative of a sulfonic acid.

(1)

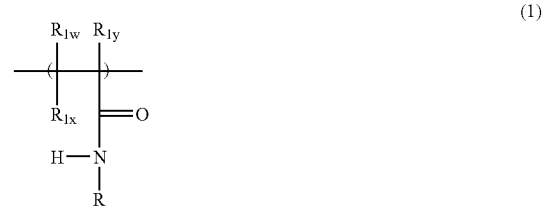

16 Claims, 9 Drawing Sheets

FOREIGN PATENT DOCUMENTS

| | | |
|---|---|---|
| EP | 0276963 | 8/1988 |
| EP | 0 475 602 A2 | 3/1992 |
| EP | 1248158 | 10/2002 |
| EP | 1336635 | 1/2007 |
| GB | 932620 | 7/1963 |
| GB | 1352802 | 5/1974 |
| GB | 1 418 216 | 12/1975 |
| JP | 49-062203 | 6/1974 |
| JP | 63184762 | 7/1988 |
| JP | 3-056974 | 3/1991 |
| JP | 04-233918 | 8/1992 |
| JP | 05-504365 | 7/1993 |
| JP | 2000-056518 | 2/2000 |
| JP | 2000-231194 | 8/2000 |
| JP | 2001-098198 | 4/2001 |
| JP | 2002351147 | 12/2002 |
| JP | 2003-286322 | * 10/2003 |
| SU | 1257074 | 9/1986 |
| WO | WO 91/09915 | 7/1991 |
| WO | WO 01/98376 | 12/2001 |
| WO | WO 2004/038512 | 5/2004 |

OTHER PUBLICATIONS

Chem. Abstracts, XP-002364025 for JP 2001-098198, Apr. 2001.

"A New Method for the Esterification of Sulphonic Acids", *Synthetic Communications*, 15 (12), 1057-1062, (1985).

* cited by examiner

POLYMER HAVING A SULFONIC GROUP OR A SULFONATE GROUP AND AN AMIDE GROUP AND METHOD OF PRODUCING SAME

TECHNICAL FIELD

The present invention relates to: a polymer having a sulfonic group or a derivative of the sulfonic group; a method of producing the polymer; and a novel compound for producing the polymer.

The present invention also relates to a charge control agent, a toner for developing an electrostatic charge image, an image forming method, and an image forming apparatus using the toner used for a recording method utilizing an electrophotographic method, an electrostatic recording method, a magnetic recording method, or the like.

BACKGROUND ART

A polymer having a hydrophilic group such as a sulfonic group is expected to find use in a wide variety of applications.

In addition, the synthesis of such a polymer containing a sulfonic group is generally limited to one involving the use of a specific vinyl monomer containing a sulfonic functional group. Specific examples of the monomer include sulfonated styrene and AMPS (2-acrylamide-2-methylpropanesulfonic acid) (for example, see JP-A 2002-351147).

DISCLOSURE OF THE INVENTION

In order to respond to the above expectation, it has been desired to provide a method of synthesizing a polymer containing the sulfonic group from a monomer other than the specific vinyl monomer described above and provision of a novel polymer containing the sulfonic group.

In view of the above background art, an object of the present invention is to provide: a polymer into which a sulfonic group or a derivative thereof is introduced; a method of producing the polymer; and a compound for producing the polymer.

The inventors of the present invention have made extensive studies with a view to developing a novel polymer into which a hydrophilic group or a polar group, which is considered to be useful in improving various kinds of functionalities, is introduced. As a result, they have completed the invention shown below.

A polymer according to a first aspect of the invention is characterized by including one or more units each having a structure represented by the following chemical formula (1).

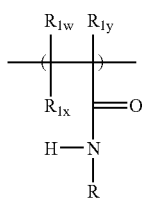

(1)

(In the formula, R represents $-A_1-SO_2R_1$. $R_{1w}$, $R_{1x}$, and $R_{1y}$ are selected from combinations described in the Following items (i) and (ii). For the item (i), $A_1$ and $R_1$ are selected from combinations described in the following items (i-A) to (i-G).

For the item (ii), $A_1$ and $R_1$ are selected from combinations described in the following item (ii-A).

(i) $R_{1w}$ and $R_{1x}$ each represent a hydrogen atom, and $R_{1y}$ represents a $CH_3$ group or a hydrogen atom.

(i-A) $A_1$ represents a methylene group, an ethylene group, a linear or branched alkylene group having 3 carbon atoms, an alkylene group having 4 carbon atoms selected from the chemical formulae (101), an alkylene group having 5 carbon atoms selected from the chemical formulae (402), a linear or branched alkylene group having 6 to 8 carbon atoms, an unsubstituted aromatic ring structure represented by the chemical formula (104a) or (104b), or an unsubstituted heterocyclic structure. $R_1$ represents a halogen atom or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-B) $A_1$ represents an unsubstituted aromatic ring structure represented by the chemical formula (105). $R_1$ represents a halogen atom or $OR_{1a}$. $R_{1a}$ represents a methyl group, a linear or branched alkyl group having 3 to 8 carbon atoms, a substituted or unsubstituted aromatic ring structure, or a substituted or unsubstituted heterocyclic structure.

(i-C) $A_1$ represents a branched alkylene group having 4 carbon atoms represented by the chemical formula (106). $R_1$ represents a halogen atom or $OR_{1a}$. $R_{1a}$ represents a linear or branched alkyl group having 3 carbon atoms, a branched alkyl group having 4 carbon atoms, a linear or branched alkyl group having 5 to 8 carbon atoms, a substituted or unsubstituted aromatic ring structure, or a substituted or unsubstituted heterocyclic structure.

(i-D) $A_1$ represents a branched alkylene group having 4 carbon atoms represented by the chemical formula (107). $R_1$ represents a halogen atom or $OR_{1a}$. $R_{1a}$ represents a linear or branched alkyl group having 2 to 8 carbon atoms, a substituted or unsubstituted aromatic ring structure, or a substituted or unsubstituted heterocyclic structure.

(i-E) $A_1$ represents a substituted aromatic ring structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-F) $A_1$ represents a substituted heterocyclic structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-G) $A_1$ represents an unsubstituted naphthalene structure. $R_1$ represents a halogen atom or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(ii) $R_{1w}$ and $R_{1x}$ each independently represent a halogen atom or a hydrogen atom. $R_{1y}$ represents a $CH_3$ group, a halogen atom, or a hydrogen atom. At least one of $R_{1w}$, $R_{1x}$, and $R_{1y}$ represents a halogen atom.

(ii-A) $A_1$ represents a substituted or unsubstituted aliphatic hydrocarbon structure, a substituted or unsubstituted aromatic ring structure, or a substituted or unsubstituted heterocyclic structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.)

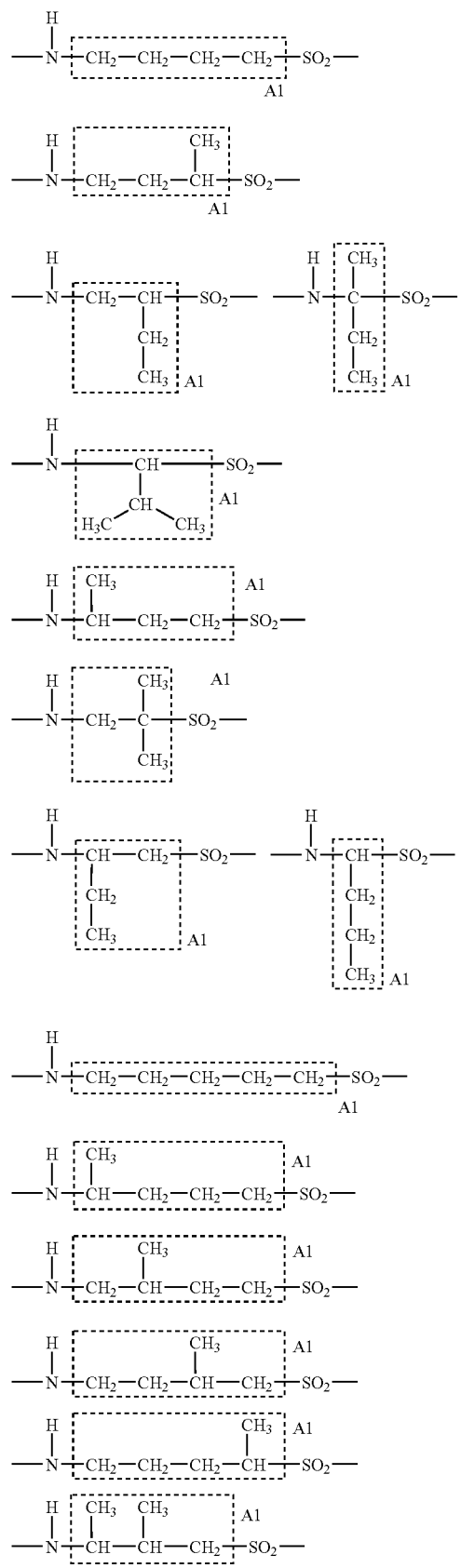
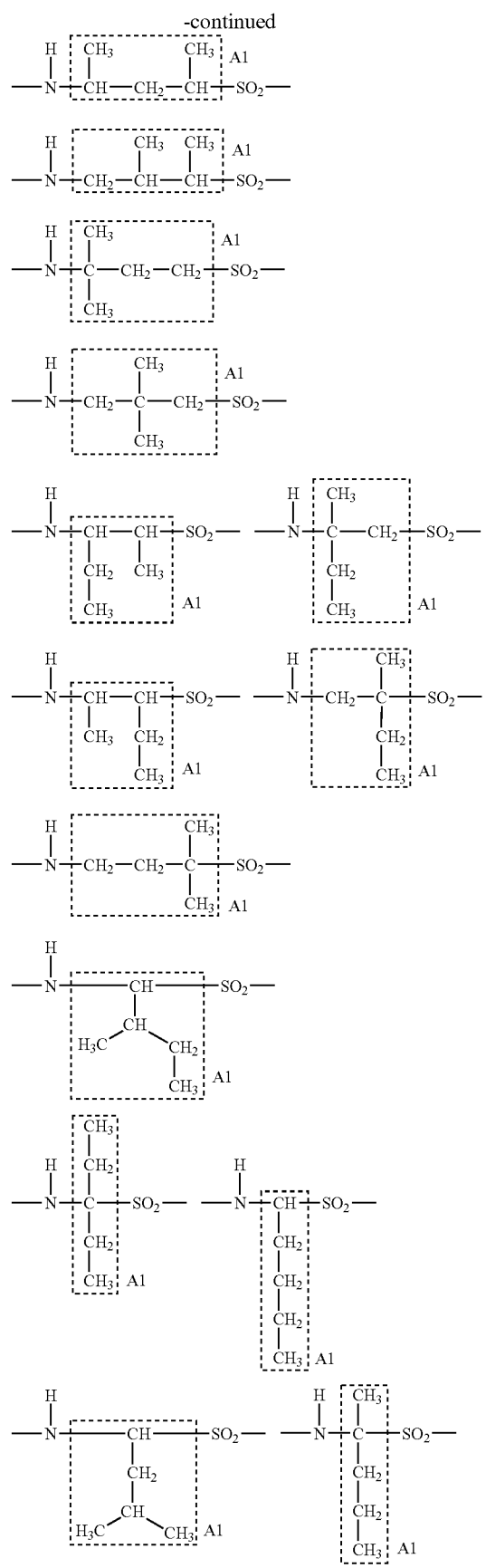

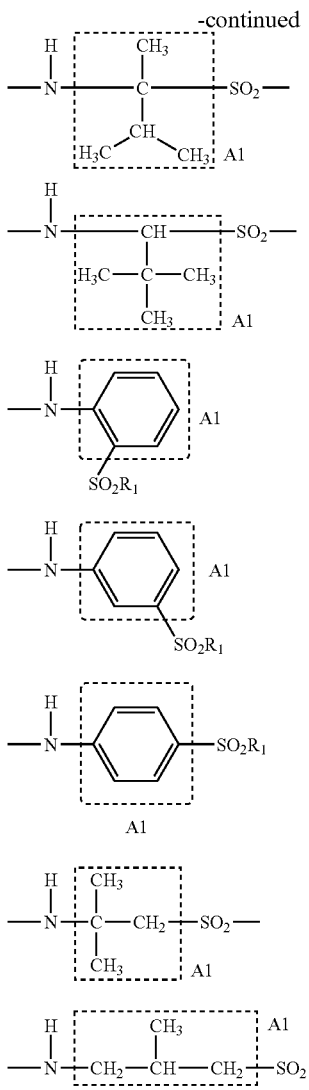

A compound according to a second aspect of the invention is represented by the chemical formula (617).

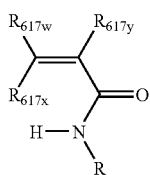

(In the formula, R represents -$A_{617}$-$SO_2R_{617}$. $R_{617w}$, $R_{617X}$, and $R_{617y}$ are selected from combinations described in the following items (i) and (ii). For the item (i), $A_{617}$ and $R_{617}$ are selected from combinations described in the following items (i-A) to (i-G). For the item (ii), $A_{617}$ and $R_{617}$ are selected from combinations described in the following item (ii-A).

(i) $R_{617w}$ and $R_{617X}$ each represent a hydrogen atom, and $R_{617y}$ represents a CH$_3$ group or a hydrogen atom.

(i-A) $A_{617}$ represents a methylene group, an ethylene group, a linear or branched alkylene group having 3 carbon atoms, an alkylene group having 4 carbon atoms selected from the chemical formulae (601), an alkylene group having 5 carbon atoms selected from the chemical formulae (602), a linear or branched alkylene group having 6 to 8 carbon atoms, an unsubstituted aromatic ring structure represented by the chemical formula (604a) or (604b), or an unsubstituted heterocyclic structure. $R_{617}$ represents a halogen atom or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-B) $A_{617}$ represents an unsubstituted aromatic ring structure represented by the chemical formula (605). $R_{617}$ represents a halogen atom or $OR_{617a}$. $R_{617a}$ represents a methyl group, a linear or branched alkyl group having 3 to 8 carbon atoms, a substituted or unsubstituted aromatic ring structure, or a substituted or unsubstituted heterocyclic structure.

(i-C) $A_{617}$ represents a branched alkylene group having 4 carbon atoms represented by the chemical formula (606). $R_{617a}$ represents a halogen atom or $OR_{617a}$. $R_{617a}$ represents a linear or branched alkyl group having 3 carbon atoms, a branched alkyl group having 4 carbon atoms, a linear or branched alkyl group having 5 to 8 carbon atoms, a substituted or unsubstituted aromatic ring structure, or a substituted or unsubstituted heterocyclic structure.

(i-D) $A_{617}$ represents a branched alkylene group having 4 carbon atoms represented by the chemical formula (607). $R_{617}$ represents a halogen atom or $OR_{617a}$. $R_{617a}$ represents a linear or branched alkyl group having 2 to 8 carbon atoms, a substituted or unsubstituted aromatic ring structure, or a substituted or unsubstituted heterocyclic structure.

(i-E) $A_{617}$ represents a substituted aromatic ring structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-F) $A_{617}$ represents a substituted heterocyclic structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-G) $A_{617}$ represents an unsubstituted naphthalene structure. $R_{617}$ represents a halogen atom or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(ii) $R_{617w}$ and $R_{617X}$ each independently represent a halogen atom or a hydrogen atom. $R_{617y}$ represents a CH$_3$ group, a halogen atom, or a hydrogen atom. At least one of $R_{617w}$, $R_{617X}$, and $R_{617y}$ represents a halogen atom.

(ii-A) $A_{617}$ represents a substituted or unsubstituted aliphatic hydrocarbon structure, a substituted or unsubstituted aromatic ring structure, or a substituted or unsubstituted heterocyclic structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.)

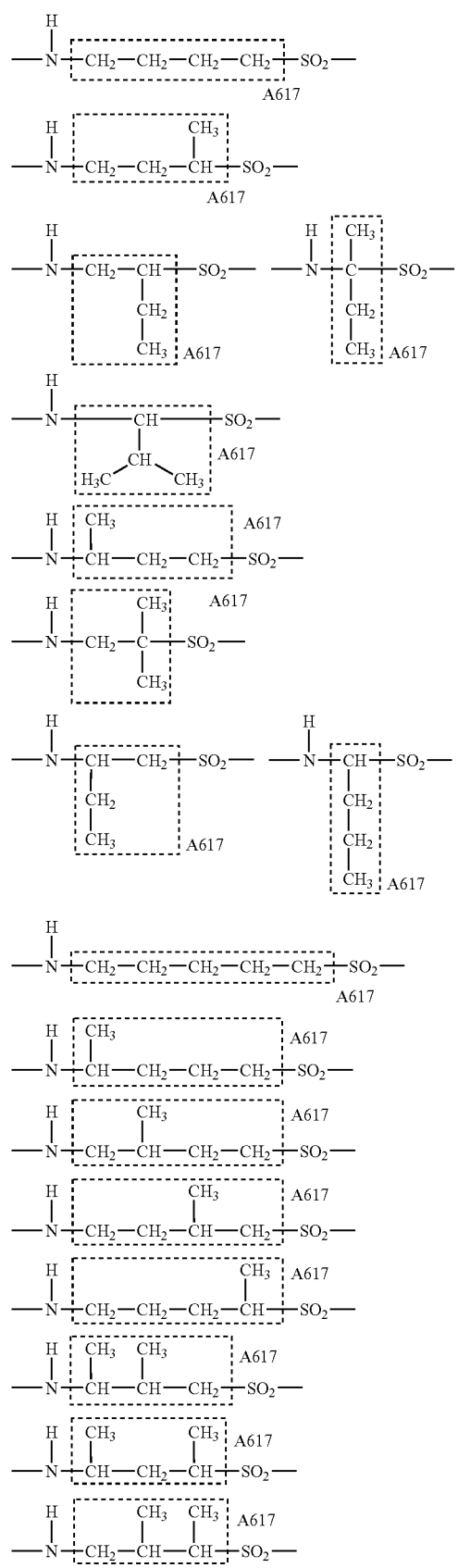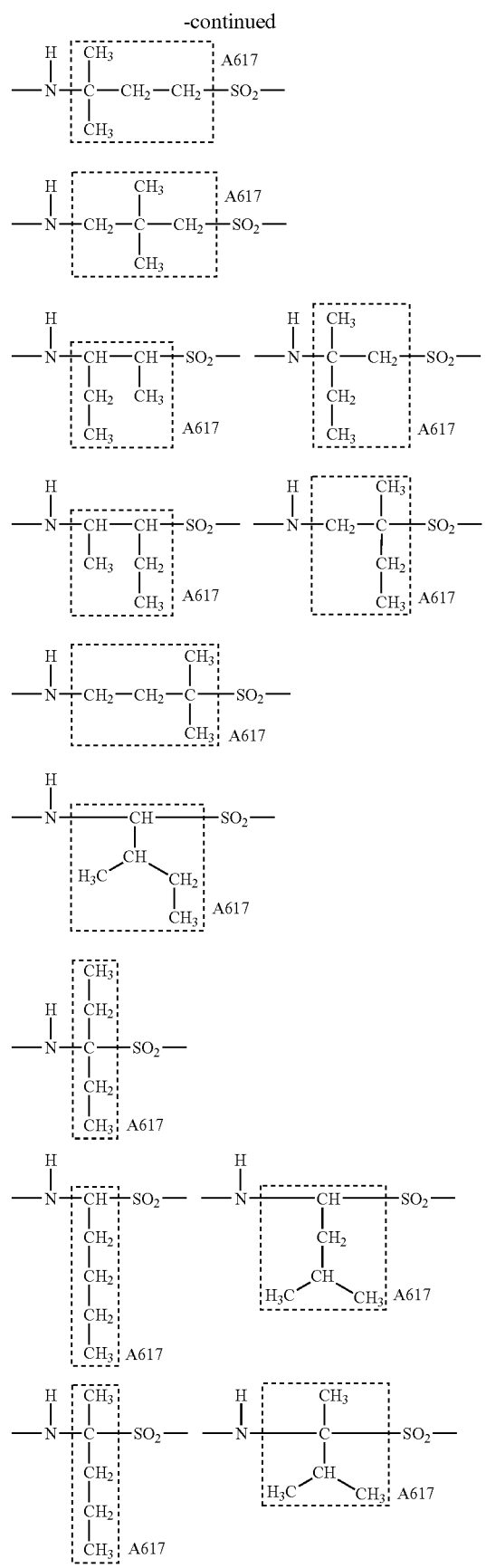

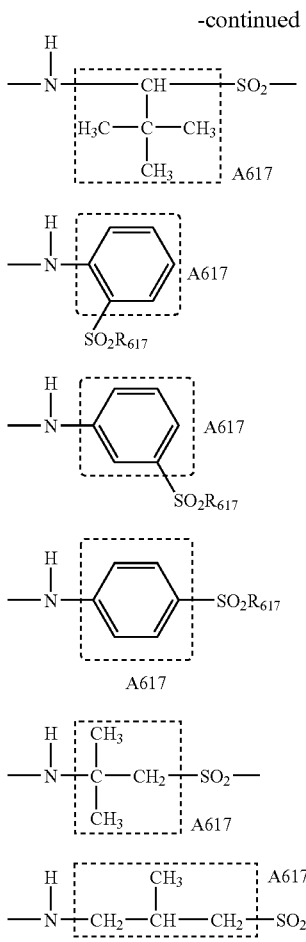

A method of producing a polymer according to the present invention is characterized by including polymerizing a compound represented by the chemical formula (617) to produce a polymer having a unit represented by the chemical formula (1).

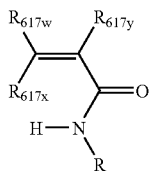

(In the formula, R represents $-A_{617}-SO_2R_{617}$. $R_{617w}$, $R_{617X}$, and $R_{617y}$ are selected from combinations described in the following items (i) and (ii). For the item (i), $A_{617}$ and $R_{617}$ are selected from combinations described in the following items (i-A) to (i-G). For the item (ii), $A_{617}$ and $R_{617}$ are selected from combinations described in the following item (ii-A).

(i) $R_{617w}$ and $R_{617X}$ each represent a hydrogen atom, and $R_{617y}$ represents a $CH_3$ group or a hydrogen atom.

(i-A) $A_{617}$ represents a methylene group, an ethylene group, a linear or branched alkylene group having 3 carbon atoms, an alkylene group having 4 carbon atoms selected from the chemical formulae (601), an alkylene group having 5 carbon atoms selected from the chemical formulae (602), a linear or branched alkylene group having 6 to 8 carbon atoms, an unsubstituted aromatic ring structure represented by the chemical formula (604a) or (604b), or an unsubstituted heterocyclic structure. $R_{617}$ represents a halogen atom or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-B) $A_{617}$ represents an unsubstituted aromatic ring structure represented by the chemical formula (605). $R_{617}$ represents a halogen atom or $OR_{617a}$. $R_{617a}$ represents a methyl group, a linear or branched alkyl group having 3 to 8 carbon atoms, a substituted or unsubstituted aromatic ring structure, or a substituted or unsubstituted heterocyclic structure.

(i-C) $A_{617}$ represents a branched alkylene group having 4 carbon atoms represented by the chemical formula (606). $R_{617}$ represents a halogen atom or $OR_{617a}$. $R_{617a}$ represents a linear or branched alkyl group having 3 carbon atoms, a branched alkyl group having 4 carbon atoms, a linear or branched alkyl group having 5 to 8 carbon atoms, a substituted or unsubstituted aromatic ring structure, or a substituted or unsubstituted heterocyclic structure.

(i-D) $A_{617}$ represents a branched alkylene group having 4 carbon atoms represented by the chemical formula (607). $R_{617}$ represents a halogen atom or $OR_{617a}$. $R_{617a}$ represents a linear or branched alkyl group having 2 to 8 carbon atoms, a substituted or unsubstituted aromatic ring structure, or a substituted or unsubstituted heterocyclic structure.

(i-E) $A_{617}$ represents a substituted aromatic ring structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-F) $A_{617}$ represents a substituted heterocyclic structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-G) $A_{617}$ represents an unsubstituted naphthalene structure. $R_{617}$ represents a halogen atom or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(ii) $R_{617w}$ and $R_{617X}$ each independently represent a halogen atom or a hydrogen atom. $R_{617y}$ represents a $CH_3$ group, a halogen atom, or a hydrogen atom. At least one of $R_{617w}$, $R_{617X}$, and $R_{617y}$ represents a halogen atom.

(ii-A) $A_{617}$ represents a substituted or unsubstituted aliphatic hydrocarbon structure, a substituted or unsubstituted aromatic ring structure, or a substituted or unsubstituted heterocyclic structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.)

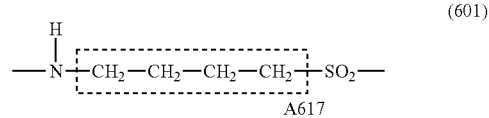

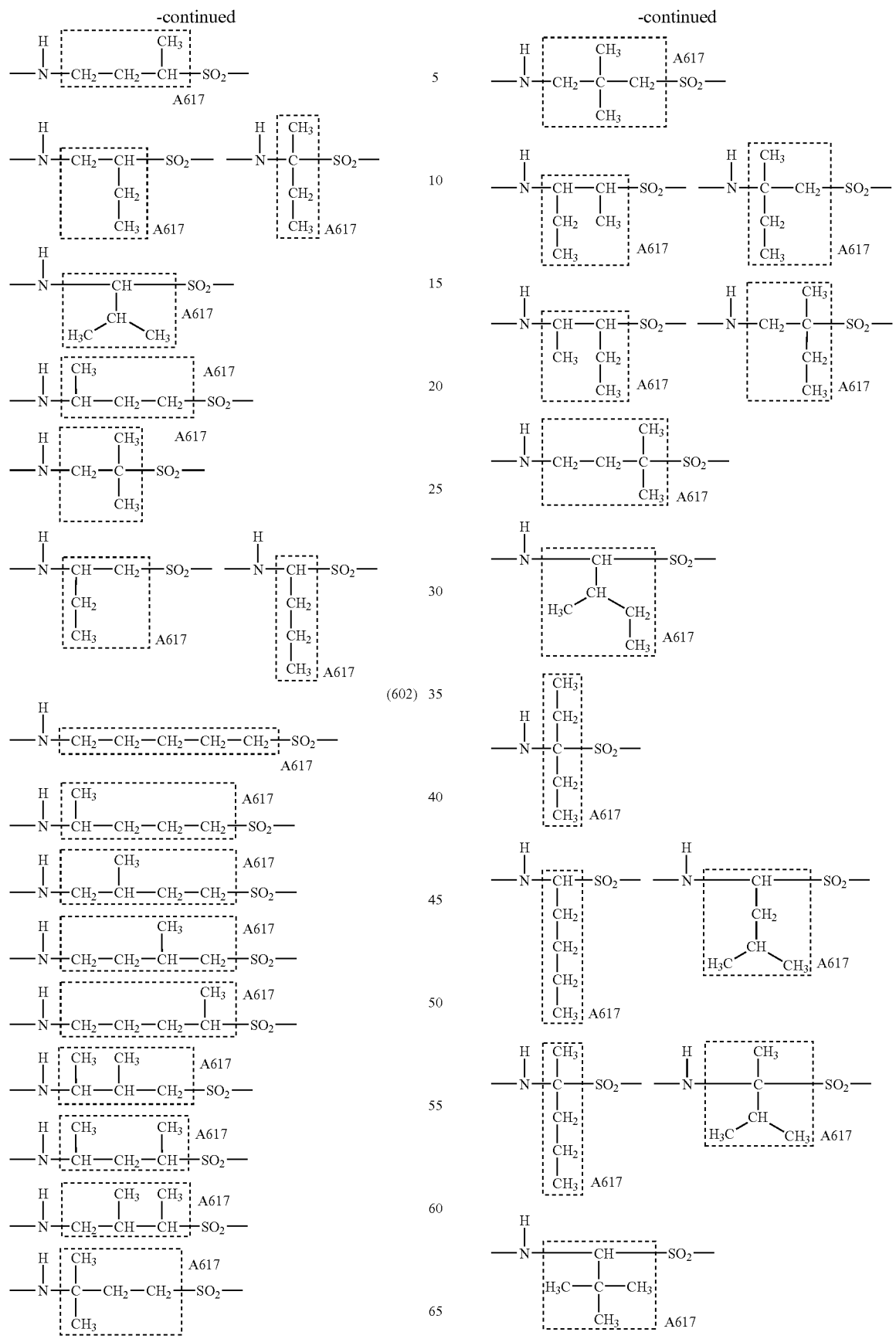

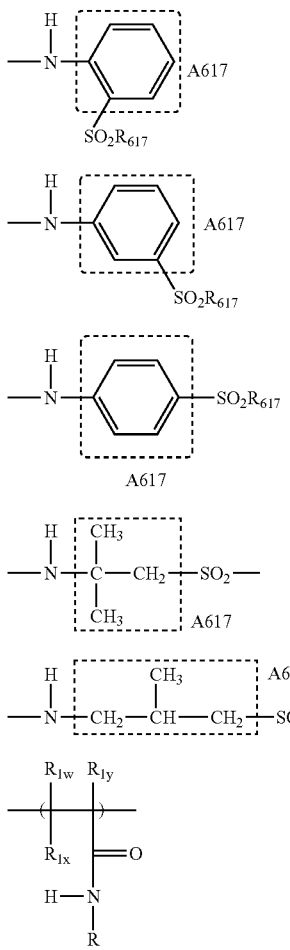

(In the formula, R represents -A₁-SO₂R₁, $R_{1w}$, $R_{1x}$, and $R_{1y}$ are selected from combinations described in the following items (i) and (ii). For the item (i), $A_1$ and $R_1$ are selected from combinations described in the following items (i-A) to (i-G). For the item (ii), $A_1$ and $R_1$ are selected from combinations described in the following item (ii-A).

(i) $R_{1w}$ and $R_{1x}$ each represent a hydrogen atom, and $R_{1y}$ represents a CH₃ group or a hydrogen atom.

(i-A) $A_1$ represents a methylene group, an ethylene group, a linear or branched alkylene group having 3 carbon atoms, an alkylene group having 4 carbon atoms selected from the chemical formulae (101), an alkylene group having 5 carbon atoms selected from the chemical formulae (402), a linear or branched alkylene group having 6 to 8 carbon atoms, an unsubstituted aromatic ring structure represented by the chemical formula (104a) or (104b), or an unsubstituted heterocyclic structure. $R_1$ represents a halogen atom or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-B) $A_1$ represents an unsubstituted aromatic ring structure represented by the chemical formula (105). $R_1$ represents a halogen atom or $OR_{1a}$. $R_{1a}$ represents a methyl group, a linear or branched alkyl group having 3 to 8 carbon atoms, a substituted or unsubstituted aromatic ring structure, or a substituted or unsubstituted heterocyclic structure.

(i-C) $A_1$ represents a branched alkylene group having 4 carbon atoms represented by the chemical formula (106). $R_1$ represents a halogen atom or $OR_{1a}$. $R_{1a}$ represents a linear or branched alkyl group having 3 carbon atoms, a branched alkyl group having 4 carbon atoms, a linear or branched alkyl group having 5 to 8 carbon atoms, a substituted or unsubstituted aromatic ring structure, or a substituted or unsubstituted heterocyclic structure.

(i-D) $A_1$ represents a branched alkylene group having 4 carbon atoms represented by the chemical formula (107). $R_1$ represents a halogen atom or $OR_{1a}$. $R_{1a}$ represents a linear or branched alkyl-group having 2 to 8 carbon atoms, a substituted or unsubstituted aromatic ring structure, or a substituted or unsubstituted heterocyclic structure.

(i-E) $A_1$ represents a substituted aromatic ring structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-F) $A_1$ represents a substituted heterocyclic structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-G) $A_1$ represents an unsubstituted naphthalene structure. $R_1$ represents a halogen atom or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(ii) $R_{1w}$ and $R_{1X}$ each independently represent a halogen atom or a hydrogen atom. $R_{1y}$ represents a CH₃ group, a halogen atom, or a hydrogen atom. At least one of $R_{1w}$, $R_{1X}$, and $R_{1y}$ represents a halogen atom.

(ii-A) $A_1$ represents a substituted or unsubstituted aliphatic hydrocarbon structure, a substituted or unsubstituted aromatic ring structure, or a substituted or unsubstituted heterocyclic structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.)

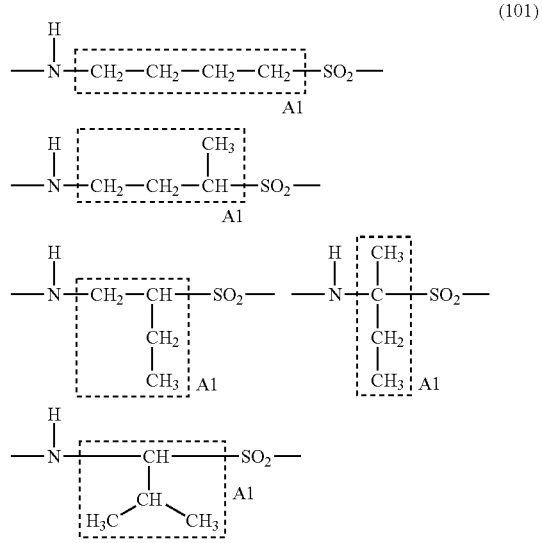

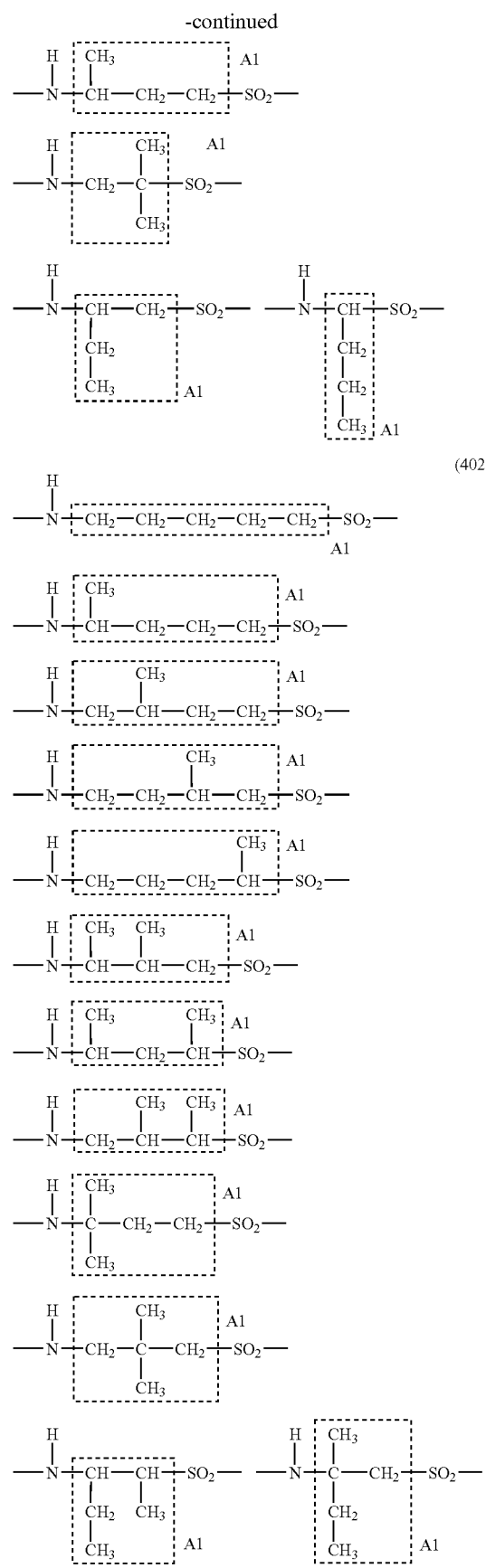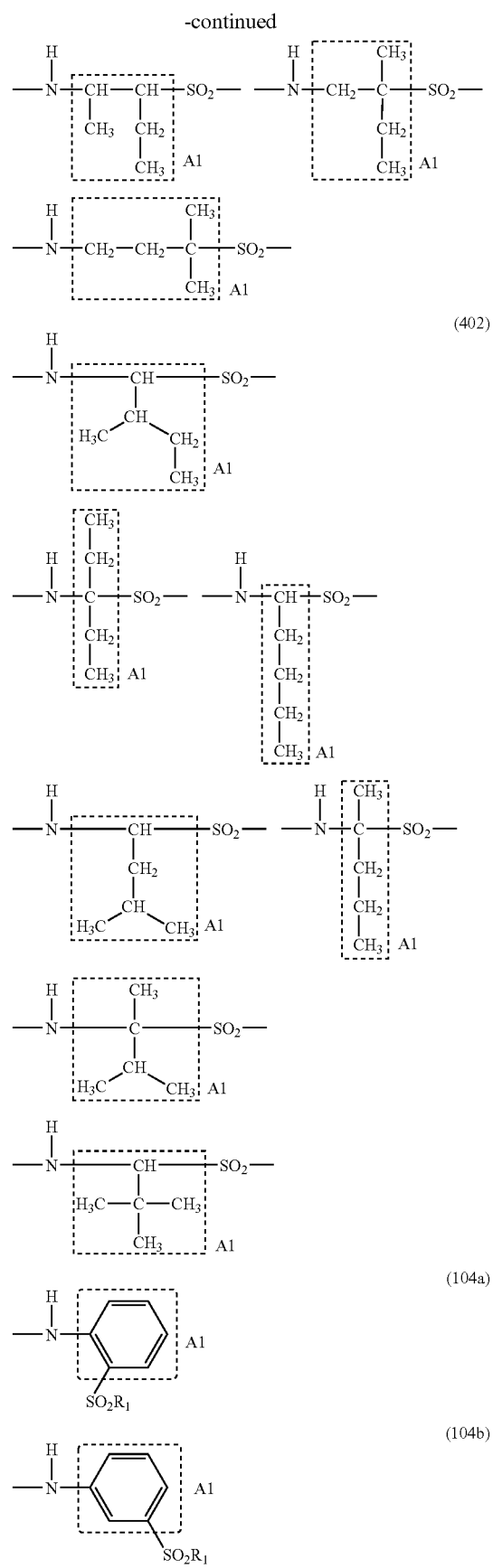

-continued

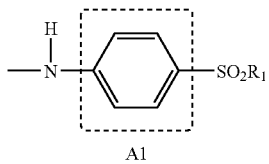

(105)

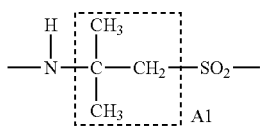

(106)

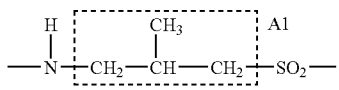

(107)

A method of producing a polymer represented by the chemical formula (16) according to the present invention is characterized by including subjecting a polymer having a unit represented by the chemical formula (14) and at least one kind of amine compound represented by the chemical formula (15) to a condensation reaction to produce a polymer having a unit represented by the chemical formula (16).

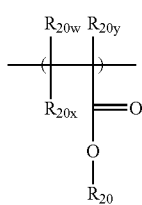

(14)

(In the formula, $R_{20w}$ and $R_{20x}$ each independently represent a halogen atom or a hydrogen atom. $R_{20y}$ represents a $CH_3$ group, a halogen atom, or a hydrogen atom. $R_{20}$ represents an H atom, an Na atom, or a K atom.)

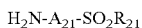

(15)

(In the formula, $R_{21}$ represents OH, a halogen atom, ONa, OK, or $OR_{21a}$. $A_{21}$ and $R_{21a}$ each independently represent a substituted or unsubstituted aliphatic hydrocarbon structure, a substituted or unsubstituted aromatic ring structure, or a substituted or unsubstituted heterocyclic structure.)

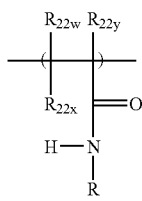

(16)

(In the formula, R represents $-A_{22}-SO_2R_{22}$. $R_{22w}$ and $R_{22x}$ each independently represent a halogen atom or a hydrogen atom. $R_{22y}$ represents a $CH_3$ group, a halogen atom, or a hydrogen atom. $R_{22}$ represents OH, a halogen atom, ONa, OK, or $OR_{22a}$. $A_{22}$ and $R_{22a}$ each independently represent a substituted or unsubstituted aliphatic hydrocarbon structure, a substituted or unsubstituted aromatic ring structure, or a substituted or unsubstituted heterocyclic structure.)

A method of producing a polymer having a unit represented by the chemical formula (18) according to the present invention is characterized by including esterifying a polymer having a unit represented by the chemical formula (17) by using an esterifying agent.

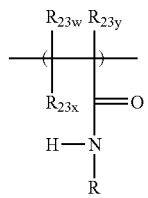

(17)

(In the formula, R represents $-A_{23}-SO_2R_{23}$. $R_{23w}$ and $R_{23x}$ each independently represent a halogen atom or a hydrogen atom. $R_{23y}$ represents a $CH_3$ group, a halogen atom, or a hydrogen atom. $R_{23}$ represents OH, a halogen atom, ONa, or OK. $A_{23}$ represents a substituted or unsubstituted aliphatic hydrocarbon structure, a substituted or unsubstituted aromatic ring structure, or a substituted or unsubstituted heterocyclic structure.)

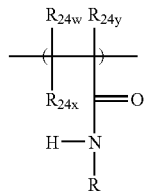

(18)

(In the formula, R represents $-A_{24}-SO_3R_{24}$. $R_{24w}$ and $R_{24x}$ each independently represent a halogen atom or a hydrogen atom. $R_{24y}$ represents a $CH_3$ group, a halogen atom, or a hydrogen atom. $A_{24}$ and $R_{24}$ each independently represent a substituted or unsubstituted aliphatic hydrocarbon structure, a substituted or unsubstituted aromatic ring structure, or a substituted or unsubstituted heterocyclic structure.)

A charge control agent for controlling a charged state of powder according to the present invention is characterized by including a polymer having a unit having a structure represented by the chemical formula (19).

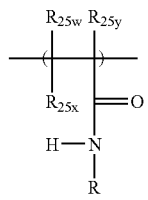

(19)

(In the formula, R represents $-A_{25}-SO_2R_{25}$. $R_{25w}$, $R_{25x}$, and $R_{25y}$ are selected from combinations described in the following items (i) and (ii). For the item (i), $A_{25}$ and $R_{25}$ are selected from combinations described in the following items (i-A) and (i-B). For the item (ii), $A_{25}$ and $R_{25}$ are selected from combinations described in the following item (ii-A).

(i) $R_{25w}$ and $R_{25X}$ each represent a hydrogen atom, and $R_{25y}$ represents a $CH_3$ group or a hydrogen atom.

(i-A) $A_{25}$ represents a substituted or unsubstituted aliphatic hydrocarbon structure. $R_{25}$ represents a halogen atom or $OR_{25a}$. $R_{25a}$ represents a substituted dr unsubstituted aliphatic hydrocarbon structure, a substituted or unsubstituted aromatic ring structure, or a substituted or unsubstituted heterocyclic structure.

(i-B) $A_{25}$ represents a substituted or unsubstituted aromatic ring structure, or a substituted or unsubstituted heterocyclic structure. $R_{25}$ represents OH, a halogen atom, ONa, OK, or $OR_{25a}$. $R_{25a}$ represents a substituted or unsubstituted aliphatic hydrocarbon structure, a substituted or unsubstituted aromatic ring structure, or a substituted or unsubstituted heterocyclic structure.

(ii) $R_{25w}$ and $R_{25X}$ each independently represent a halogen atom or a hydrogen atom. $R_{25y}$ represents a $CH_3$ group, a halogen atom, or a hydrogen atom. At least one of $R_{25w}$, $R_{25X}$, and $R_{25y}$ represents a halogen atom (ii-A) $A_{25}$ represents a substituted or unsubstituted aliphatic hydrocarbon structure, a substituted or unsubstituted aromatic ring structure, or a substituted or unsubstituted heterocyclic structure. $R_{25}$ represents OH, a halogen atom, ONa, OK, or $OR_{25a}$. $R_{25a}$ represents a substituted or unsubstituted aliphatic hydrocarbon structure, a substituted or unsubstituted aromatic ring structure, or a substituted or unsubstituted heterocyclic structure.)

A charge control agent for controlling a charged state of powder according to the present invention is characterized by containing at least one kind of polymer containing one or more units each having the structure represented by the chemical formula (1).

A toner for developing an electrostatic charge image according to the present invention is characterized by containing at least: a binder resin; a colorant; and a charge control agent having a structure represented by the chemical formula (1) or the chemical formula (19).

According to the present invention, an image forming method is provided including at least the steps of: applying a voltage from an outside to a charging member to charge an electrostatic latent image-bearing member; forming an electrostatic charge image on the charged electrostatic latent image-bearing member; developing the electrostatic charge image with toner for developing an electrostatic charge image to form a toner image on the electrostatic latent image-bearing member; transferring the toner image on the electrostatic latent image-bearing member onto a recording material; and fixing the toner image on the recording material under heating, wherein the toner for developing an electrostatic charge image having the above structure is used.

According to the present invention, an image forming apparatus is provided including at least: a means for externally applying a voltage to a charging member to charge an electrostatic latent image-bearing member; a means for forming an electrostatic charge image on the charged electrostatic latent image-bearing member; a means for developing the electrostatic charge image with toner for developing an electrostatic charge image to form a toner image on the electrostatic latent image-bearing member; a means for transferring the toner image on the electrostatic latent image-bearing member onto a recording material; and a means for fixing the toner image on the recording material under heating, wherein the toner for developing an electrostatic charge image having the above structure is used as the toner for developing an electrostatic charge image;

EFFECT OF THE INVENTION

The present invention provides a polymer into which a sulfonic group or a derivative of the sulfonic group is introduced, a method of producing the same, and a compound for producing the polymer.

Figure 1:
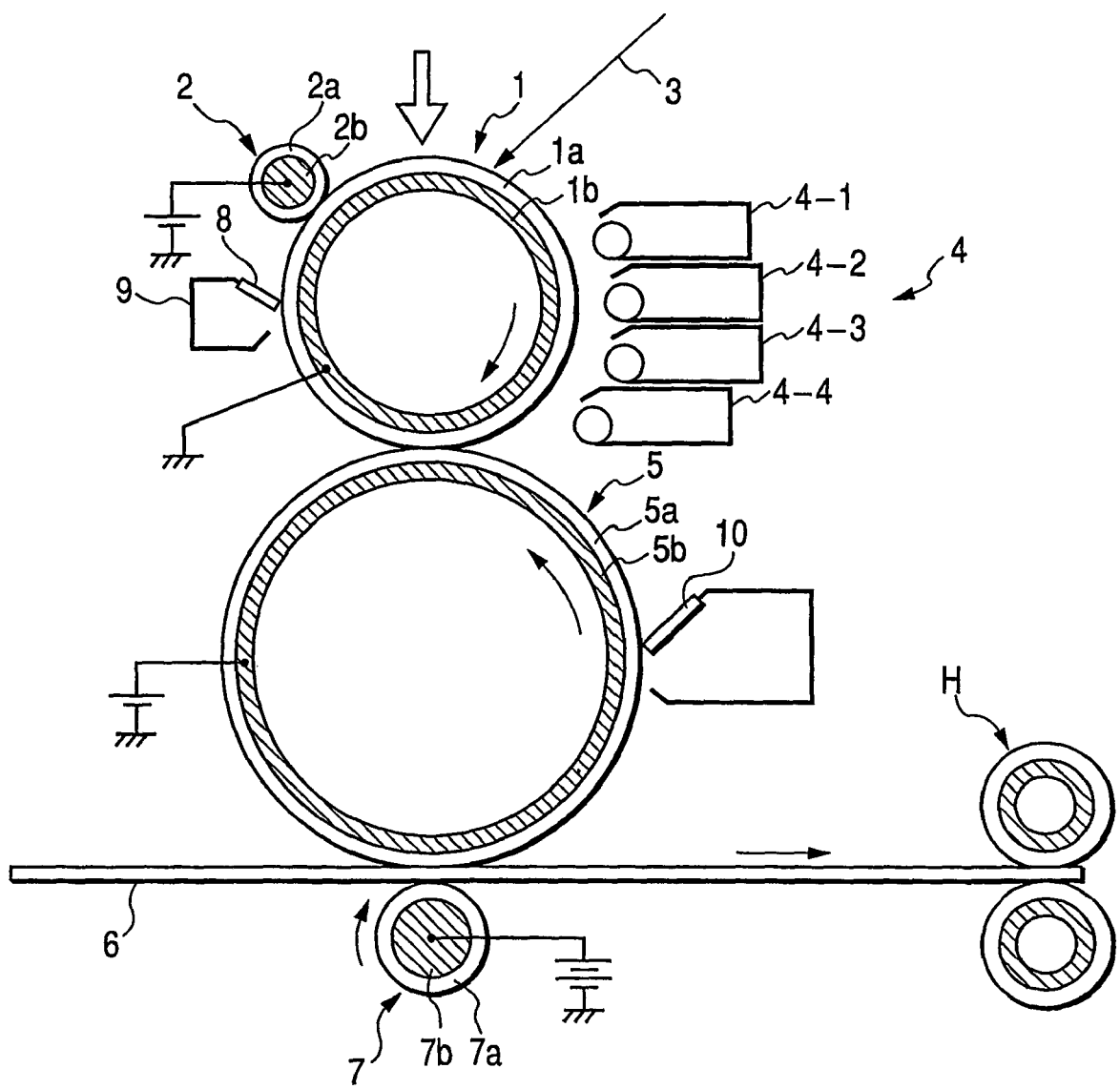
FIG. 1 is a schematic view for explaining an image forming apparatus used in each of Examples 31 to 36 and Comparative Examples 7 to 12.

BEST MODE FOR CARRYING OUT THE INVENTION (Polymer and Compound According to the Present Invention)

(1) A polymer according to a first invention is characterized by including one or more units each having a structure represented by the chemical formula (1).

(1)

(In the formula, R represents $-A_1-SO_2R_1$. $R_{1w}$, $R_{1x}$, and $R_{1y}$ are selected from combinations described in the following items (i) and (ii). For the item (i), $A_1$ and $R_1$ are selected from combinations described in the following items (i-A) to (i-G). For the item (ii), $A_1$ and $R_1$ are selected from combinations described in the following item (ii-A).

(i) $R_{1w}$ and $R_{1x}$ each represent a hydrogen atom, and $R_{1y}$ represents a $CH_3$ group or a hydrogen atom.

(i-A) $A_1$ represents a methylene group, an ethylene group, a linear or branched alkylene group having 3 carbon atoms, an alkylene group having 4 carbon atoms selected from the chemical formulae (101), an alkylene group having 5 carbon atoms selected from the chemical formulae (402), a linear or branched alkylene group having 6 to 8 carbon atoms, an unsubstituted aromatic ring structure represented by the chemical formula (104a) or (104b), or an unsubstituted heterocyclic structure. $R_1$ represents a halogen atom or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-B) $A_1$ represents an unsubstituted aromatic ring structure represented by the chemical formula (105). $R_1$ represents a halogen atom or $OR_{1a}$. $R_{1a}$ represents a methyl group, a linear or branched alkyl group having 3 to 8 carbon atoms, a substituted or unsubstituted aromatic ring structure, or a substituted or unsubstituted heterocyclic structure.

(i-C) $A_1$ represents a branched alkylene group having 4 carbon atoms represented by the chemical formula (106). $R_1$ represents a halogen atom or $OR_{1a}$. $R_{1a}$ represents a linear or branched alkyl group having 3 carbon atoms, a branched alkyl group having 4 carbon atoms, a linear or branched alkyl group having 5 to 8 carbon atoms, a substituted or unsubstituted aromatic ring structure, or a substituted or unsubstituted heterocyclic structure.

(i-D) $A_1$ represents a branched alkylene group having 4 carbon atoms represented by the chemical formula (107). $R_1$ represents a halogen atom or $OR_{1a}$. $R_{1a}$ represents a linear or branched alkyl group having 2 to 8 carbon atoms, a substituted or unsubstituted aromatic ring structure, or a substituted or unsubstituted heterocyclic structure.

(i-E) $A_1$ represents a substituted aromatic ring structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-F) $A_1$ represents a substituted heterocyclic structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(i-G) $A_1$ represents an unsubstituted naphthalene structure. $R_1$ represents a halogen atom or $OR_{1a}$. $R_{1a}$ represents a substituted or unsubstituted aliphatic hydrocarbon structure, a substituted or unsubstituted aromatic ring structure, or a substituted or unsubstituted heterocyclic structure.

(ii) $R_{1w}$ and $R_{1x}$ each independently represent a halogen atom or a hydrogen atom. $R_{1y}$ represents a $CH_3$ group, a halogen atom, or a hydrogen atom. At least one of $R_{1w}$, $R_{1x}$, and $R_{1y}$ represents a halogen atom.

(ii-A) $A_1$ represents a substituted or unsubstituted aliphatic hydrocarbon structure, a substituted or unsubstituted aromatic ring structure, or a substituted or unsubstituted heterocyclic structure. $R_1$ represents OH, a halogen atom, ONa, OK, or $OR_{1a}$. $R_{1a}$ represents a substituted or unsubstituted aliphatic hydrocarbon structure, a substituted or unsubstituted aromatic ring structure, or a substituted or unsubstituted heterocyclic structure.)

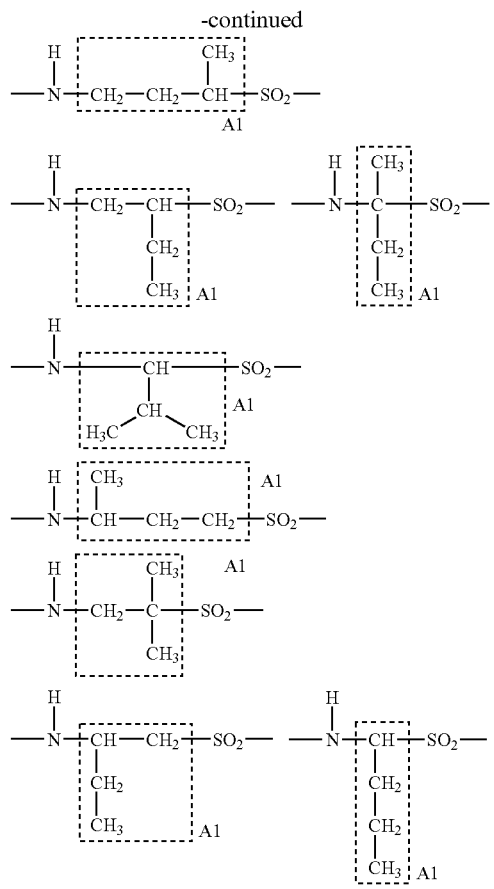

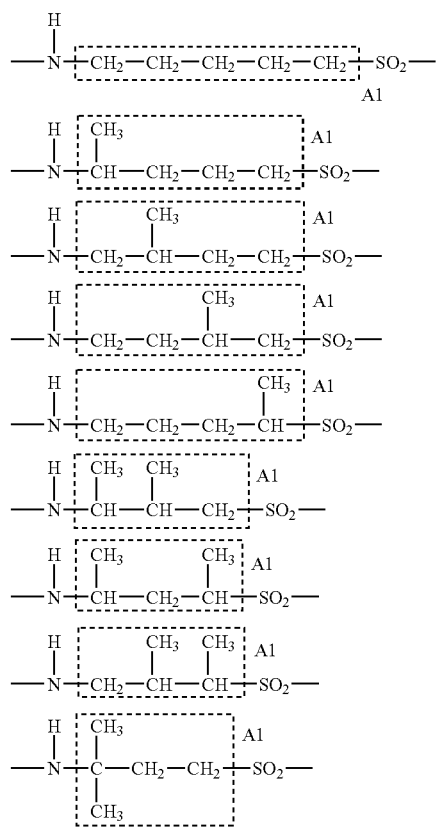

-continued

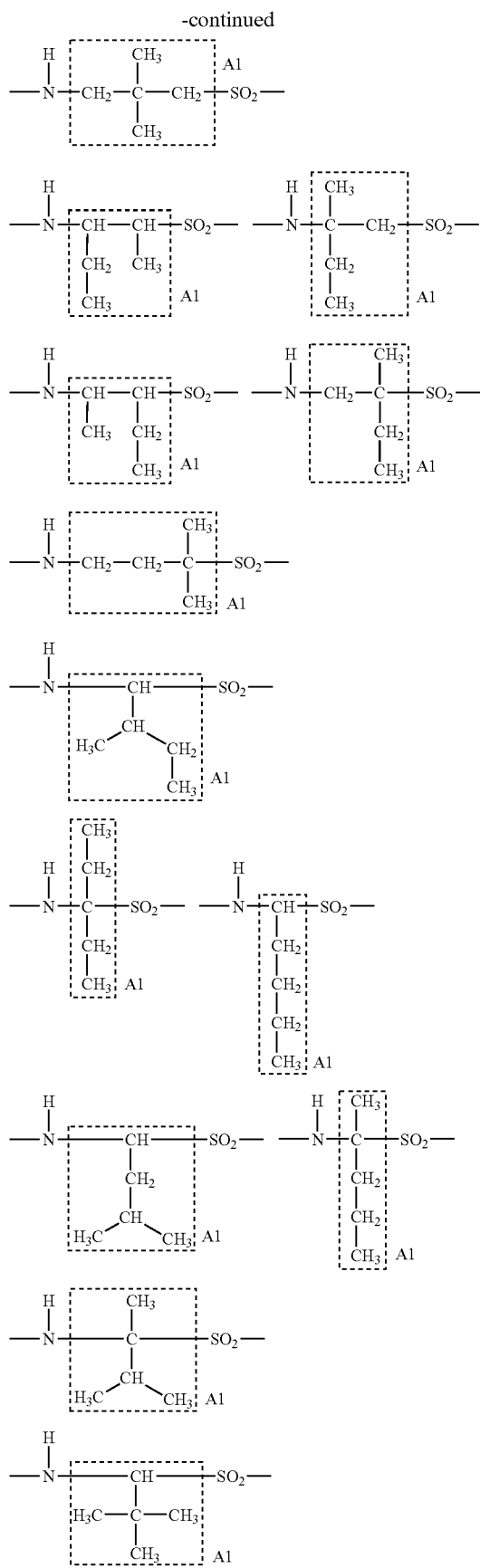

-continued

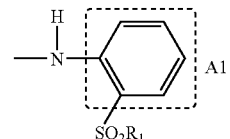
(104a)

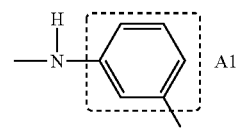
(104b)

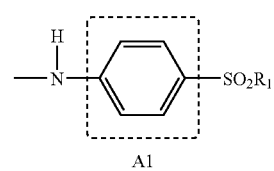
(105)

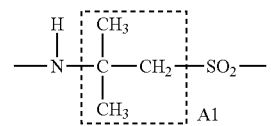
(106)

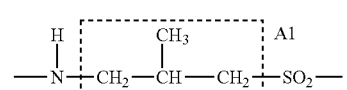
(107)

In the present invention, when multiple kinds of units selected from the above combinations are present in the polymer, the respective units are independent from each other. That is, the present invention includes the case where the polymer is comprised of the same kind of unit and the case where the polymer is comprised of units different from each other.

(2) A polymer according to a second invention is characterized in that the structure represented by the chemical formula (1) corresponds to the chemical formula (2).

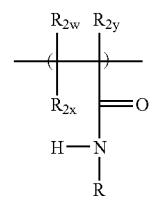
(2)

(In the formula, R represents -$A_2$-$SO_2R_2$. $R_{2w}$ and $R_{2x}$ each represent a hydrogen atom, and $R_{2y}$ represents a $CH_3$ group or a hydrogen atom. $A_2$ represents a methylene group, an ethylene group, a linear or branched alkylene group having 3 carbon atoms, an alkylene group having 4 carbon atoms represented by the chemical formula (401), an alkylene group having 5 carbon atoms represented by the chemical formula (502), a linear or branched alkylene group having 6 to 8 carbon atoms, an unsubstituted aromatic ring structure represented by the chemical formula (409a) or (409b), or an unsubstituted heterocyclic structure. $R_2$ represents a halogen atom or $OR_{2a}$. $R_{2a}$ represents a linear or branched alkyl group having 1 to 8 carbon atoms, or a substituted or unsubstituted phenyl group.)
(401)
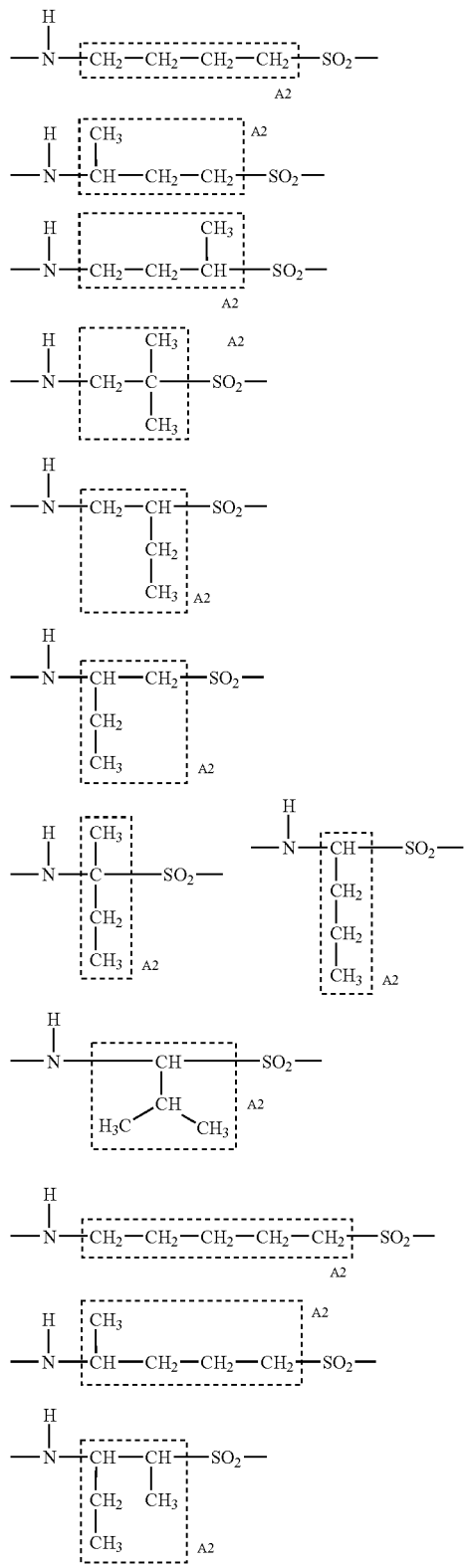
(502)
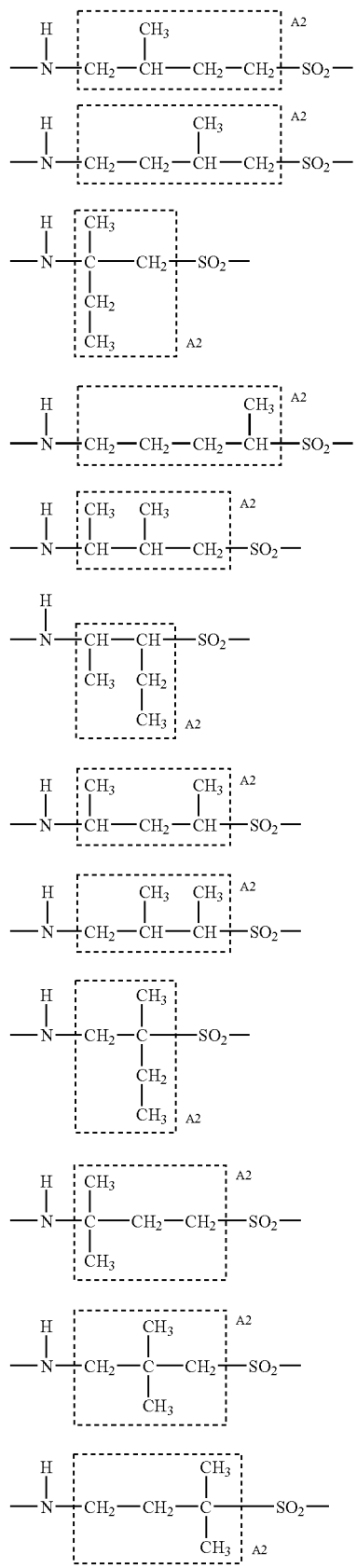

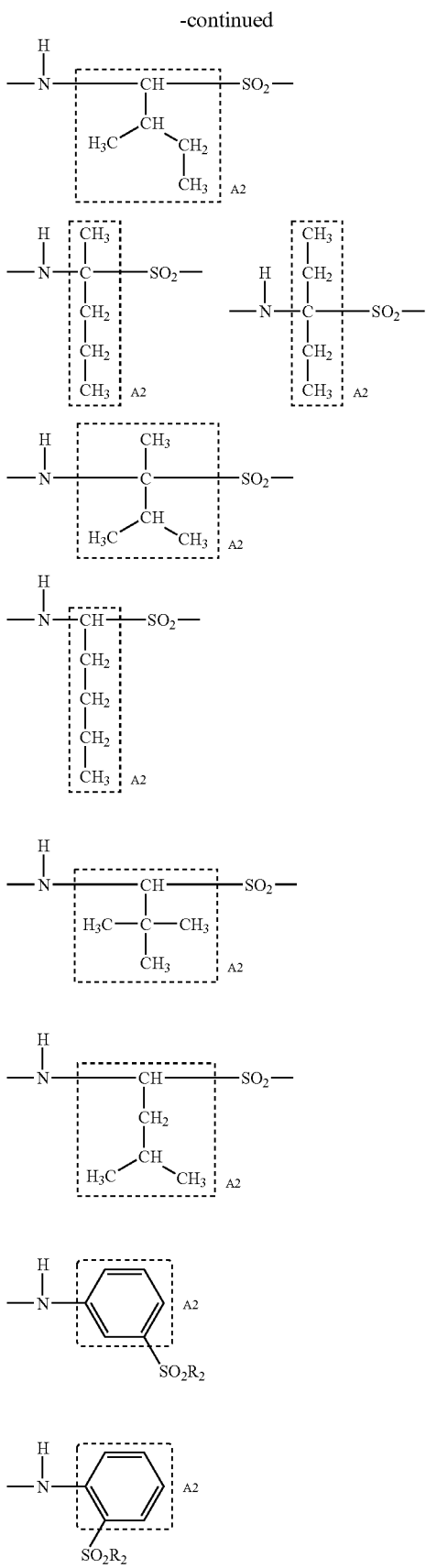

(409a)

(409b)

(3) A polymer according to a third invention is characterized in that the structure represented by the chemical formula (1) corresponds to the chemical formula (5).

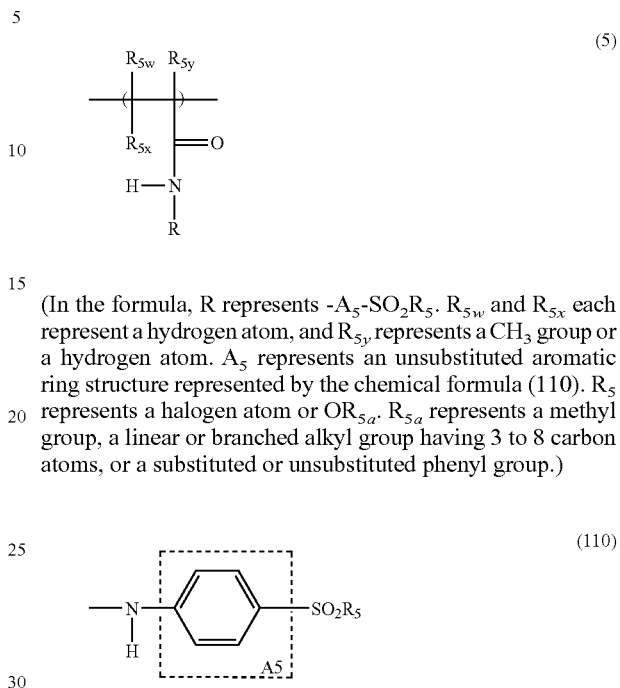

(In the formula, R represents $-A_5-SO_2R_5$. $R_{5w}$ and $R_{5x}$ each represent a hydrogen atom, and $R_{5y}$ represents a $CH_3$ group or a hydrogen atom. $A_5$ represents an unsubstituted aromatic ring structure represented by the chemical formula (110). $R_5$ represents a halogen atom or $OR_{5a}$. $R_{5a}$ represents a methyl group, a linear or branched alkyl group having 3 to 8 carbon atoms, or a substituted or unsubstituted phenyl group.)

(4) A polymer according to a fourth invention is characterized in that the structure represented by the chemical formula (1) corresponds to the chemical formula (6).

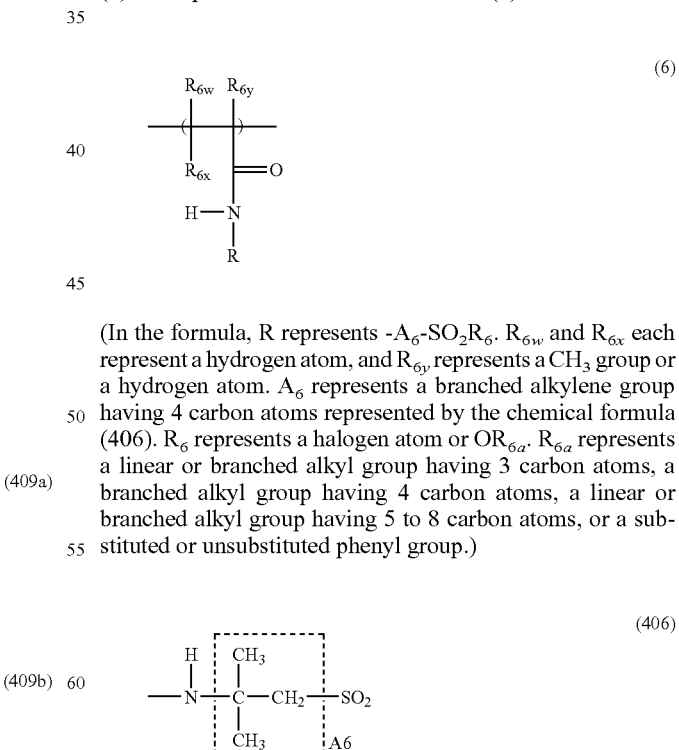

(In the formula, R represents $-A_6-SO_2R_6$. $R_{6w}$ and $R_{6x}$ each represent a hydrogen atom, and $R_{6y}$ represents a $CH_3$ group or a hydrogen atom. $A_6$ represents a branched alkylene group having 4 carbon atoms represented by the chemical formula (406). $R_6$ represents a halogen atom or $OR_{6a}$. $R_{6a}$ represents a linear or branched alkyl group having 3 carbon atoms, a branched alkyl group having 4 carbon atoms, a linear or branched alkyl group having 5 to 8 carbon atoms, or a substituted or unsubstituted phenyl group.)

(5) A polymer according to a fifth invention is characterized in that the structure represented by the chemical formula (1) corresponds to the chemical formula (7).

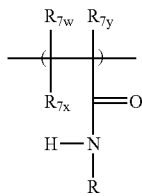
(7)

(In the formula, R represents -$A_7$-$SO_2R_7$. $R_{7w}$ and $R_{7x}$ each represent a hydrogen atom, and $R_{7y}$ represents a $CH_3$ group or a hydrogen atom. $A_7$ represents a branched alkylene group having 4 carbon atoms represented by the chemical formula (407). $R_7$ represents a halogen atom or $OR_{7a}$. $R_{7a}$ represents a linear or branched alkyl group having 2 to 8 carbon atoms, or a substituted or unsubstituted phenyl group.)

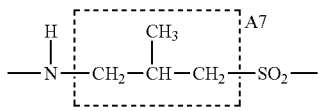
(407)

(6) A polymer according to a sixth invention is characterized in that the structure represented by the chemical formula (1) corresponds to the chemical formula (8).

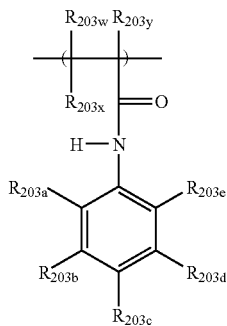
(8)

(In the formula, $R_{203w}$ and $R_{203x}$ each represent a hydrogen atom, and $R_{203y}$ represents a $CH_3$ group or a hydrogen atom. At least one of $R_{203a}$, $R_{203b}$, $R_{203c}$, $R_{203d}$, and $R_{203e}$ represents $SO_2R_{203f}$ ($R_{203f}$ represents OH, a halogen atom, ONa, OK, or $OR_{203}$-h. $R_{203h}$ represents a linear or branched alkyl group having 1 to 8 carbon atoms, or a substituted or unsubstituted phenyl group). Each of $R_{203a}$, $R_{203b}$, $R_{203c}$, $R_{203d}$, and $R_{203e}$ is selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{203g}$ ($R_{203g}$ represents an H atom, an Na atom, or a K atom), an acetamide group, an OPh group, an NHPh group, a $CF_3$ group, a $C_2F_5$ group, and a $C_3F_7$ group. Up to three of $R_{203a}$, $R_{203b}$, $R_{203c}$, $R_{203d}$, and $R_{203e}$ can represent hydrogen atoms.)

(7) A polymer according to a seventh invention is characterized in that the structure represented by the chemical formula (1) corresponds to the chemical formula (507).

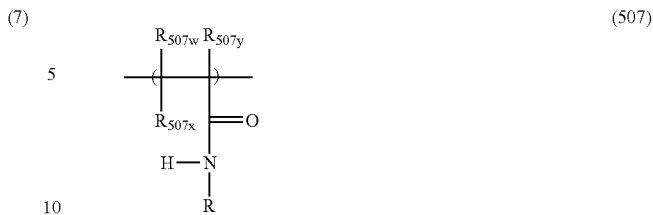
(507)

(In the formula, R represents -$A_{507}$-$SO_2R_{507}$. $R_{507w}$ and $R_{507x}$ each represent a hydrogen atom, and $R_{507y}$ represents a $CH_3$ group or a hydrogen atom. $A_{507}$ represents a substituted heterocyclic structure. $R_{507}$ represents OH, a halogen atom, ONa, OK, or $OR_{507a}$. $R_{507a}$ represents a linear or branched alkyl group having 1 to 8 carbon atoms, or a substituted or unsubstituted phenyl group.)

(8) A polymer according to an eighth invention is characterized in that the structure represented by the chemical formula (1) corresponds to the chemical formula (509a) or (509b).

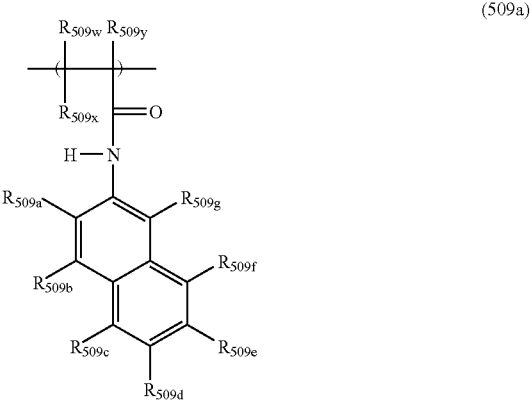
(509a)

(In the formula, $R_{509w}$ and $R_{509x}$ each represent a hydrogen atom, and $R_{509y}$ represents a $CH_3$ group or a hydrogen atom. One of $R_{509a}$, $R_{509b}$, $R_{509c}$, $R_{509d}$, $R_{509e}$, $R_{509f}$ and $R_{509o}$ represents $SO_2R_{509o}$ ($R_{509o}$ represents a halogen atom or $OR_{509s}$. $R_{509s}$ represents a linear or branched alkyl group having 1 to 8 carbon atoms, or a substituted or unsubstituted phenyl group). The others represent hydrogen atoms.)

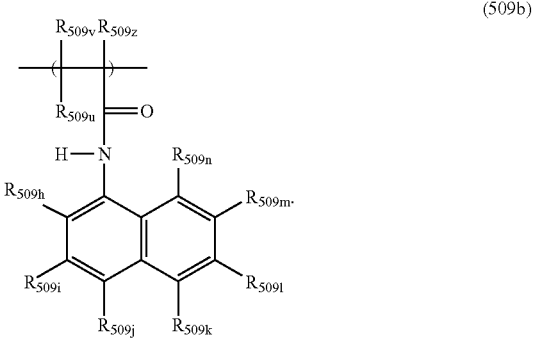
(509b)

(In the formula, $R_{509v}$ and $R_{509u}$ each represent a hydrogen atom, and $R_{509z}$ represents a $CH_3$ group or a hydrogen atom. One of $R_{509h}$, $R_{509i}$, $R_{509j}$, $R_{509k}$, $R_{509l}$, $R_{509m}$, and $R_{509n}$ represents $SO_2R_{509q}$ ($R_{509q}$ represents a halogen atom or $OR_{509r}$. $R_{509r}$ represents a linear or branched alkyl group having 1 to 8 carbon atoms, or a substituted or unsubstituted phenyl group). The others represent hydrogen atoms.)

(9) A polymer according to a ninth invention is characterized in that the structure represented by the chemical formula (1) corresponds to the chemical formula (9a) or (9b).

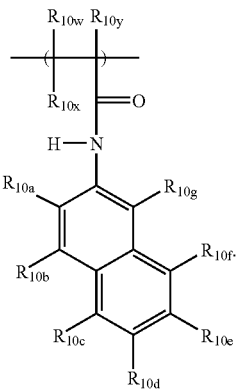

(9a)

(In the formula, $R_{10w}$ and $R_{10x}$ each represent a hydrogen atom, and $R_{10y}$ represents a $CH_3$ group or a hydrogen atom. At least one of $R_{10a}$, $R_{10b}$, $R_{10c}$, $R_{10d}$, $R_{10e}$, $R_{10f}$, and $R_{10g}$ represents $SO_2R_{10o}$ ($R_{10o}$ represents OH, a halogen atom, ONa, OK, or $OR_{10s}$. $R_{10s}$ represents a linear or branched alkyl group having 1 to 8 carbon atoms, or a substituted or unsubstituted phenyl group). Each of $R_{10a}$, $R_{10b}$, $R_{10c}$, $R_{10d}$, $R_{10e}$, $R_{10f}$, and $R_{10g}$ is selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{10p}$ ($R_{10p}$ represents an H atom, an Na atom, or a K atom), an acetamide group, an OPh group, an NHPh group, a $CF_3$ group, a $C_2F_5$ group, and a $C_3F_7$ group. Up to five of $R_{10a}$, $R_{10b}$, $R_{10c}$, $R_{10d}$, $R_{10e}$, $R_{10f}$, and $R_{10g}$ can represent hydrogen atoms.)

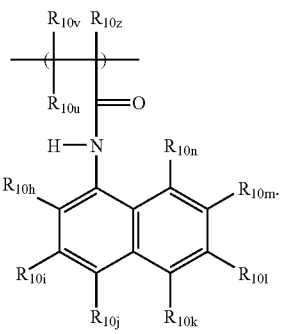

(9b)

(In the formula, $R_{10v}$ and $R_{10u}$ each represent a hydrogen atom, and $R_{10z}$ represents a $CH_3$ group or a hydrogen atom. At least one of $R_{10h}$, $R_{10i}$, $R_{10j}$, $R_{10k}$, $R_{10l}$, $R_{10m}$, and $R_{10n}$ represents $SO_2R_{10q}$ ($R_{10q}$ represents OH, a halogen atom, ONa, OK, or $OR_{10r}$. $R_{10r}$ represents a linear or branched alkyl group having 1 to 8 carbon atoms, or a substituted or unsubstituted phenyl group). Each of $R_{10h}$, $R_{10i}$, $R_{10j}$, $R_{10k}$, $R_{10l}$, $R_{10m}$, and $R_{10n}$ is selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{10r}$ ($R_{10r}$ represents an H atom, an Na atom, or a K atom), an acetamide group, an OPh group, an NHPh group, a $CF_3$ group, a $C_2F_5$ group, and a $C_3F_7$ group. Up to five of $R_{10h}$, $R_{10i}$, $R_{10j}$, $R_{10k}$, $R_{10l}$, $R_{10m}$, and $R_{10n}$ can represent hydrogen atoms.)

(10) A polymer according to a tenth invention is characterized in that the structure represented by the chemical formula (1) corresponds to the chemical formula (10).

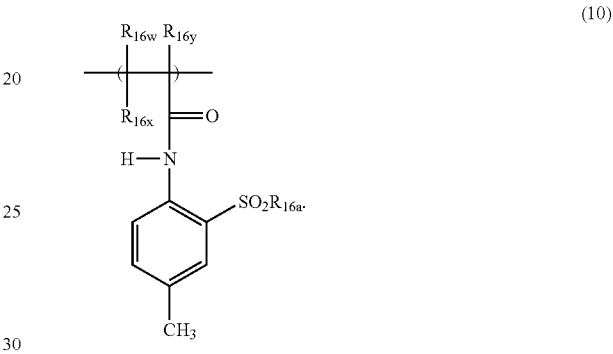

(10)

(In the formula, $R_{16w}$ and $R_{16x}$ each represent a hydrogen atom, and $R_{16y}$ represents a $CH_3$ group or a hydrogen atom. $R_{16a}$ represents OH, a halogen atom, ONa, OK, or $OR_{16b}$. $R_{16b}$ represents a linear or branched alkyl group having 1 to 8 carbon atoms, or a substituted or unsubstituted phenyl group.)

(11) A polymer according to an eleventh invention is characterized in that the structure represented by the chemical formula (1) corresponds to the chemical formula (11).

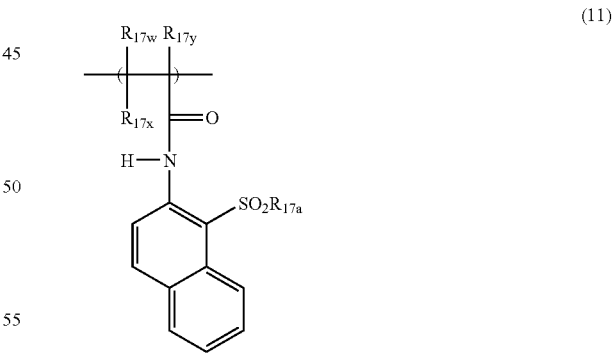

(11)

(In the formula, $R_{17w}$ and $R_{17x}$ each represent a hydrogen atom, and $R_{17y}$ represents a $CH_3$ group or a hydrogen atom. $R_{17a}$ represents a halogen atom or $OR_{17b}$. $R_{17b}$ represents a linear or branched alkyl group having 1 to 8 carbon atoms, or a substituted or unsubstituted phenyl group.)

(12) A polymer according to a twelfth invention is characterized in that the structure represented by the chemical formula (1) corresponds to the chemical formula (12).

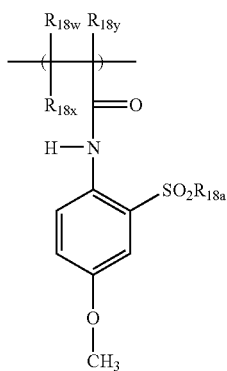

(12)

(In the formula, $R_{18w}$ and $R_{18x}$ each represent a hydrogen atom, and $R_{18y}$ represents a $CH_3$ group or a hydrogen atom. $R_{18a}$ represents OH, a halogen atom, ONa, OK, or $OR_{18b}$. $R_{18b}$ represents a linear or branched alkyl group having 1 to 8 carbon atoms, or a substituted or unsubstituted phenyl group.)

(13) A polymer according to a thirteenth invention is characterized in that the structure represented by the chemical formula (1) corresponds to the chemical formula (13).

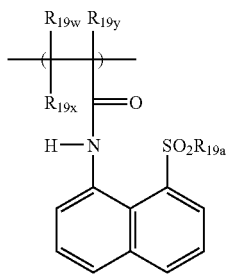

(13)

(In the formula, $R_{19w}$ and $R_{19x}$ each represent a hydrogen atom, and $R_{19y}$ represents a $CH_3$ group or a hydrogen atom. $R_{19a}$ represents OH, a halogen atom, ONa, OK, or $OR_{19b}$. $R_{19b}$ represents a linear or branched alkyl group having 1 to 8 carbon atoms, or a substituted or unsubstituted phenyl group.)

(14) A polymer according to a fourteenth invention is characterized in that the structure represented by the chemical formula (1) corresponds to the chemical formula (301).

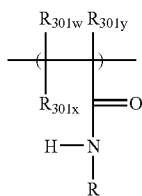

(301)

(In the formula, R represents -$A_{301}$-$SO_2R_{301}$. $R_{301w}$ and $R_{301x}$ each independently represent a halogen atom or a hydrogen atom, and $R_{301y}$ represents a $CH_3$ group, a halogen atom, or a hydrogen atom. At least one of $R_{301w}$, $R_{301x}$, and $R_{301y}$ represents a halogen atom. $A_{301}$ represents a substituted or unsubstituted aliphatic hydrocarbon structure, a substituted or unsubstituted aromatic ring structure, or a substituted or unsubstituted heterocyclic structure. $R_{301}$ represents OH, a halogen atom, ONa, OK, or $OR_{301a}$. $R_{301a}$ represents a linear or branched alkyl group having 1 to 8 carbon atoms, or a substituted or unsubstituted phenyl group.)

(15) A polymer according to a fifteenth invention is characterized by further including at least one unit derived from a vinyl-based monomer represented by the chemical formula (108) in addition to the unit represented by the chemical formula (1).

(108)

(In the formula, $R_{108w}$ and $R_{108x}$ each independently represent a halogen atom or a hydrogen atom, and $R_{108y}$ represents a $CH_3$ group, a halogen atom, or a hydrogen atom. $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{108a}$, —O—$R_{108b}$, —COO—$R_{108c}$, —OCO—$R_{108d}$, —CONR$_{108e}R_{108f}$, —CN, or a ring structure containing an N atom. $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.)

It is a matter of course that the 15th invention can be applied to any one of the 2nd to 14th invention.

(16) A polymer according to a sixteenth invention is characterized in that the polymer according to any one of the first to fifteenth invention has a number average molecular weight of 1,000 to 1,000,000.

(17) A compound according to a seventeenth invention is characterized by being represented by the chemical formula (617).

(617)

(In the formula, R represents -$A_{617}$-$SO_2R_{617}$. $R_{617w}$, $R_{617x}$, and $R_{617y}$ are selected from combinations described in the following items (i) and (ii). For the item (i), $A_{617}$ and $R_{617}$ are selected from combinations described in the following items (i-A) to (i-G). For the item (ii), $A_{617}$ and $R_{617}$ are selected from combinations described in the following item (ii-A).

(i) $R_{617w}$ and $R_{617x}$ each represent a hydrogen atom, and $R_{617y}$ represents a $CH_3$ group or a hydrogen atom.

(i-A) $A_{617}$ represents a methylene group, an ethylene group, a linear or branched alkylene group having 3 carbon atoms, an alkylene group having 4 carbon atoms selected from the chemical formulae. (601), an alkylene group having 5 carbon atoms selected from the chemical formulae (602), a linear or branched alkylene group having 6 to 8 carbon atoms, an unsubstituted aromatic ring structure represented by the chemical formula (604a) or (604b), or an unsubstituted heterocyclic structure. $R_{617}$ represents a halogen atom or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-B) $A_{617}$ represents an unsubstituted aromatic ring structure represented by the chemical formula (605). $R_{617}$ represents a halogen atom or $OR_{617a}$. $R_{617a}$ represents a methyl group, a linear or branched alkyl group having 3 to 8 carbon atoms, a substituted or unsubstituted aromatic ring structure, or a substituted or unsubstituted heterocyclic structure.

(i-C) $A_{617}$ represents a branched alkylene group having 4 carbon atoms represented by the chemical formula (606). $R_{617}$ represents a halogen atom or $OR_{617a}$. $R_{617a}$ represents a linear or branched alkyl group having 3 carbon atoms, a branched alkyl group having 4 carbon atoms, a linear or branched alkyl group having 5 to 8 carbon atoms, a substituted or unsubstituted aromatic ring structure, or a substituted or unsubstituted heterocyclic structure.

(i-D) $A_{617}$ represents a branched alkylene group having 4 carbon atoms represented by the chemical formula (607). $R_{617}$ represents a halogen atom or $OR_{617a}$. $R_{617a}$ represents a linear or branched alkyl group having 2 to 8 carbon atoms, a substituted or unsubstituted aromatic ring structure, or a substituted or unsubstituted heterocyclic structure.

(i-E) $A_{617}$ represents a substituted aromatic ring structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-F) $A_{617}$ represents a substituted heterocyclic structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(i-G) $A_{617}$ represents an unsubstituted naphthalene structure. $R_{617}$ represents a halogen atom or $OR_{617a}$. $R_{617a}$ represents a substituted or unsubstituted aliphatic hydrocarbon structure, a substituted or unsubstituted aromatic ring structure, or a substituted or unsubstituted heterocyclic structure.

(ii) $R_{617w}$ and $R_{617x}$ each independently represent a halogen atom or a hydrogen atom. $R_{617y}$ represents a $CH_3$ group, a halogen atom, or a hydrogen atom. At least one of $R_{617w}$, $R_{617x}$, and $R_{617y}$ represents a halogen atom.

(ii-A) $A_{617}$ represents a substituted or unsubstituted aliphatic hydrocarbon structure, a substituted or unsubstituted aromatic ring structure, or a substituted or unsubstituted heterocyclic structure. $R_{617}$ represents OH, a halogen atom, ONa, OK, or $OR_{617a}$. $R_{617a}$ represents a substituted or unsubstituted aliphatic hydrocarbon structure, a substituted or unsubstituted aromatic ring structure, or a substituted or unsubstituted heterocyclic structure.)

(601)

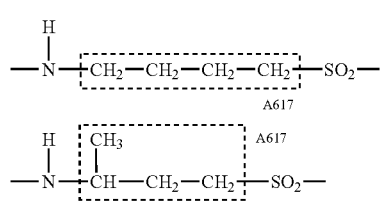

-continued

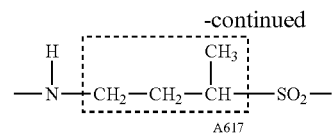

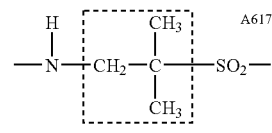

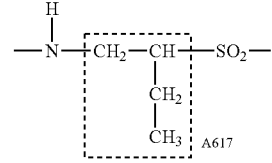

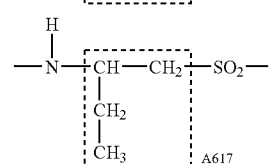

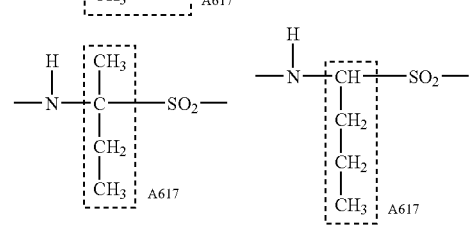

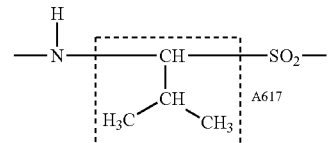

(602)

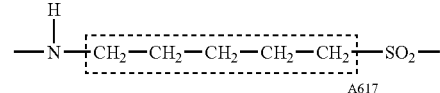

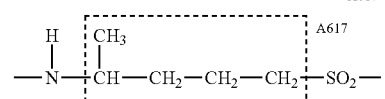

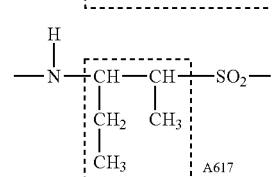

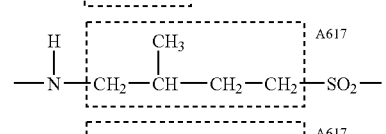

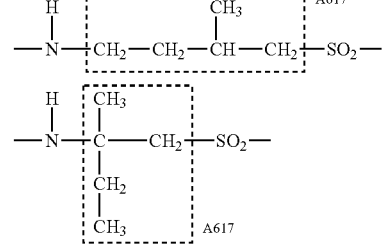

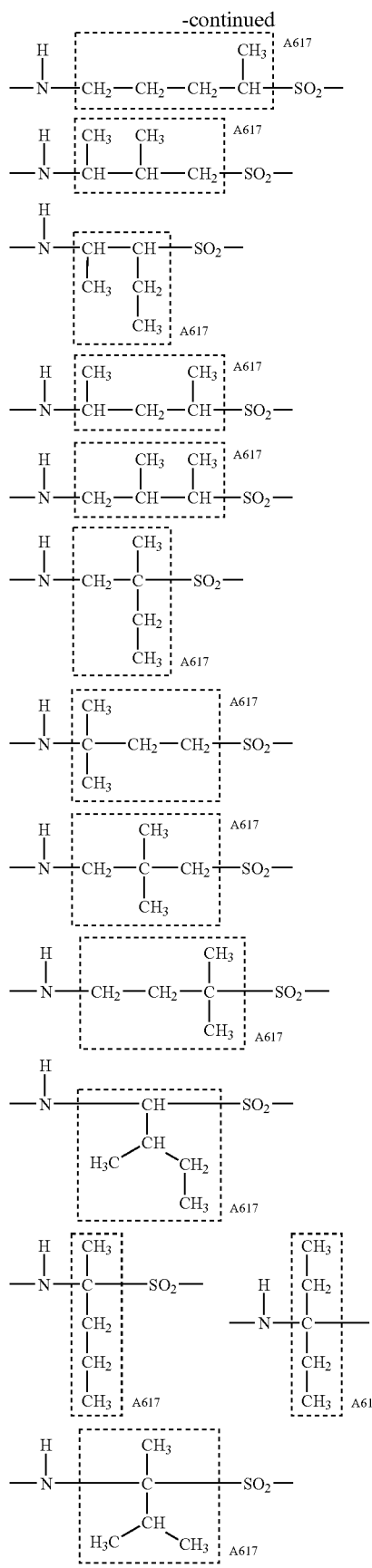
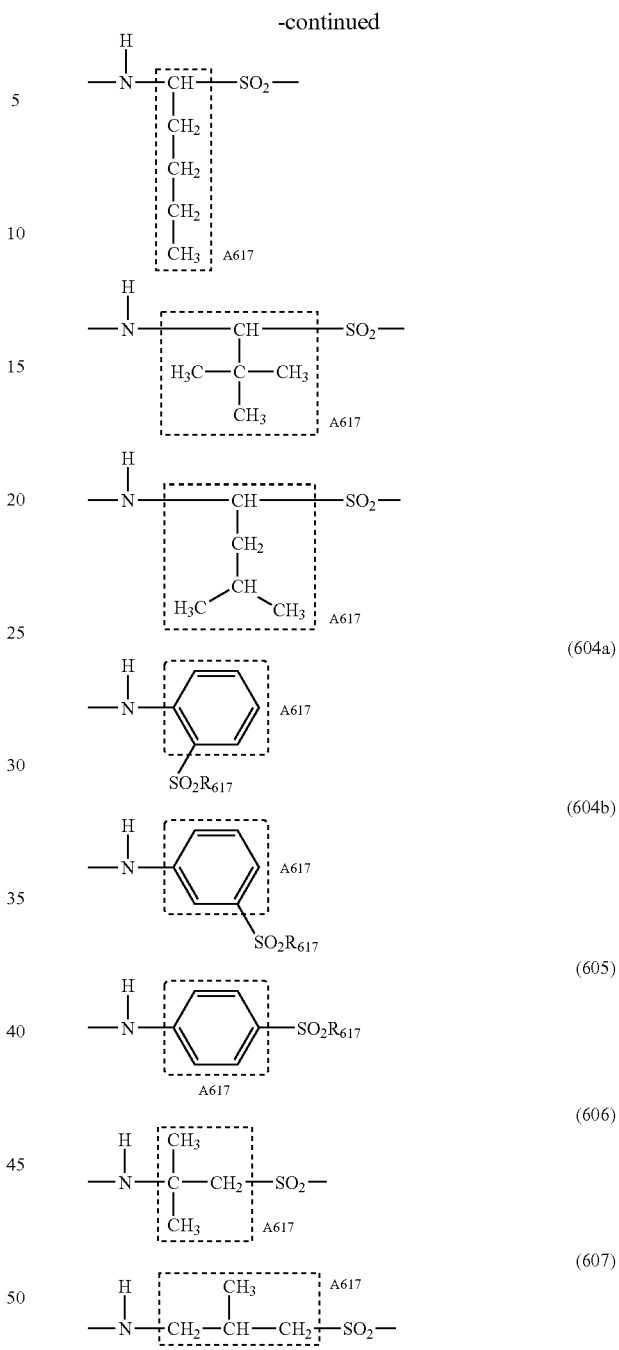
(18) A compound according to an eighteenth invention is characterized in that the compound represented by the chemical formula (617) has a structure represented by the chemical formula (618).
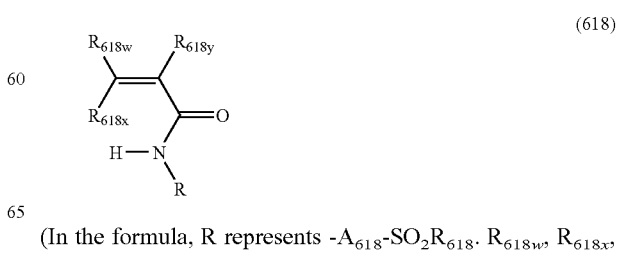
(In the formula, R represents $-A_{618}-SO_2R_{618}$. $R_{618w}$, $R_{618x}$, and $R_{618y}$ are selected from combinations described in the following items (i) and (ii). For the item (i), $A_{618}$ and $R_{618}$ are selected from combinations described in the following items (i-A) to (i-D). For the item (ii), $A_{618}$ and $R_{618}$ are selected from combinations described in the following item (ii-A).

(i) $R_{618w}$ and $R_{618x}$ each represent a hydrogen atom, and $R_{618y}$ represents a $CH_3$ group or a hydrogen atom.

(i-A) $A_{618}$ represents a methylene group, an ethylene group a linear or branched alkylene group having 3 carbon atoms, an alkylene group having 4 carbon atoms selected from the chemical formulae (701), an alkylene group having 5 carbon atoms selected from the chemical formulae (702), a linear or branched alkylene group having 6 to 8 carbon atoms, an unsubstituted aromatic ring structure, or an unsubstituted heterocyclic structure. $R_{618}$ represents a halogen atom or $OR_{618a}$. $R_{618a}$ represents a methyl group, an ethyl group, or a phenyl group.

(i-B) $A_{618}$ represents a branched alkylene group having 4 carbon atoms represented by the chemical formula (706). $R_{618}$ represents a halogen atom or $OR_{618a}$. $R_{618a}$ represents a phenyl group.

(i-C) $A_{618}$ represents a branched alkylene group having 4 carbon atoms represented by the chemical formula (707). $R_{618}$ represents a halogen atom, OK, or $OR_{618a}$. $R_{618a}$ represents an ethyl group or a phenyl group.

(i-D) $A_{618}$ represents a substituted aromatic ring structure or a substituted heterocyclic structure. $R_{618}$ represents OH, a halogen atom, ONa, OK, or $OR_{618a}$. $R_{618a}$ represents a methyl group, an ethyl group, or a phenyl group.

(ii) $R_{618w}$ and $R_{618x}$ each independently represent a halogen atom or a hydrogen atom. $R_{618y}$ represents a $CH_3$ group, a halogen atom, or a hydrogen atom. At least one of $R_{618w}$, $R_{618x}$, and $R_{618y}$ represents a halogen atom.

(ii-A) $A_{618}$ represents a substituted or unsubstituted aliphatic hydrocarbon structure, a substituted or unsubstituted aromatic ring structure, or a substituted or unsubstituted heterocyclic structure. $R_{618}$ represents OH, a halogen atom, ONa, OK, or $OR_{618a}$. $R_{618a}$ represents a methyl group, an ethyl group, or a phenyl group.)

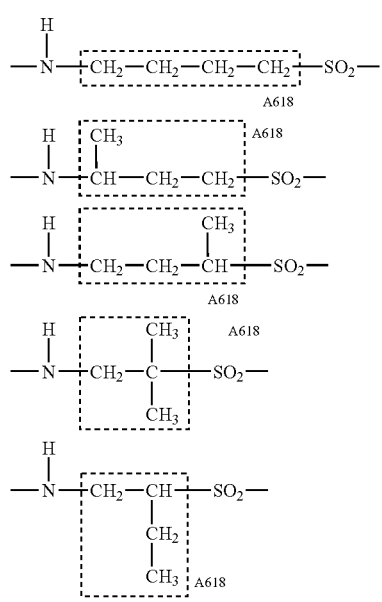

(701)

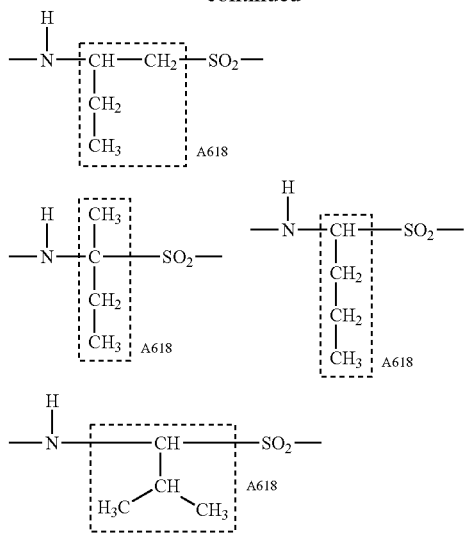

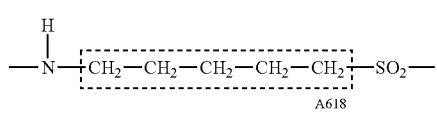

(702)

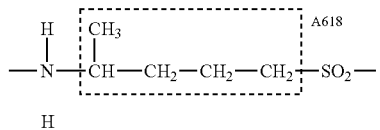

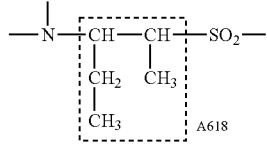

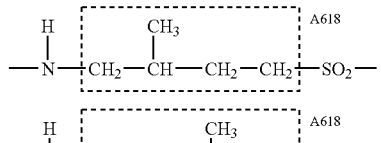

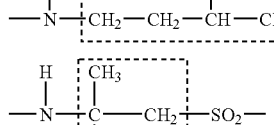

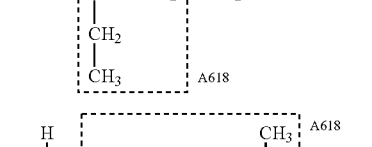

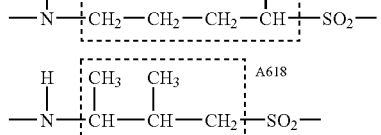

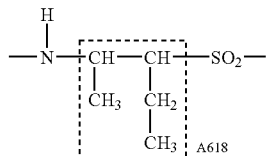

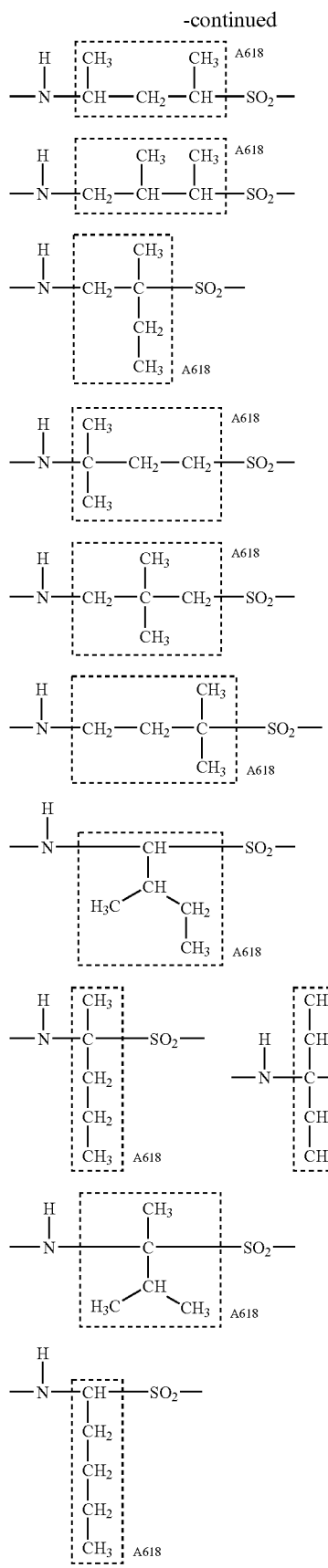

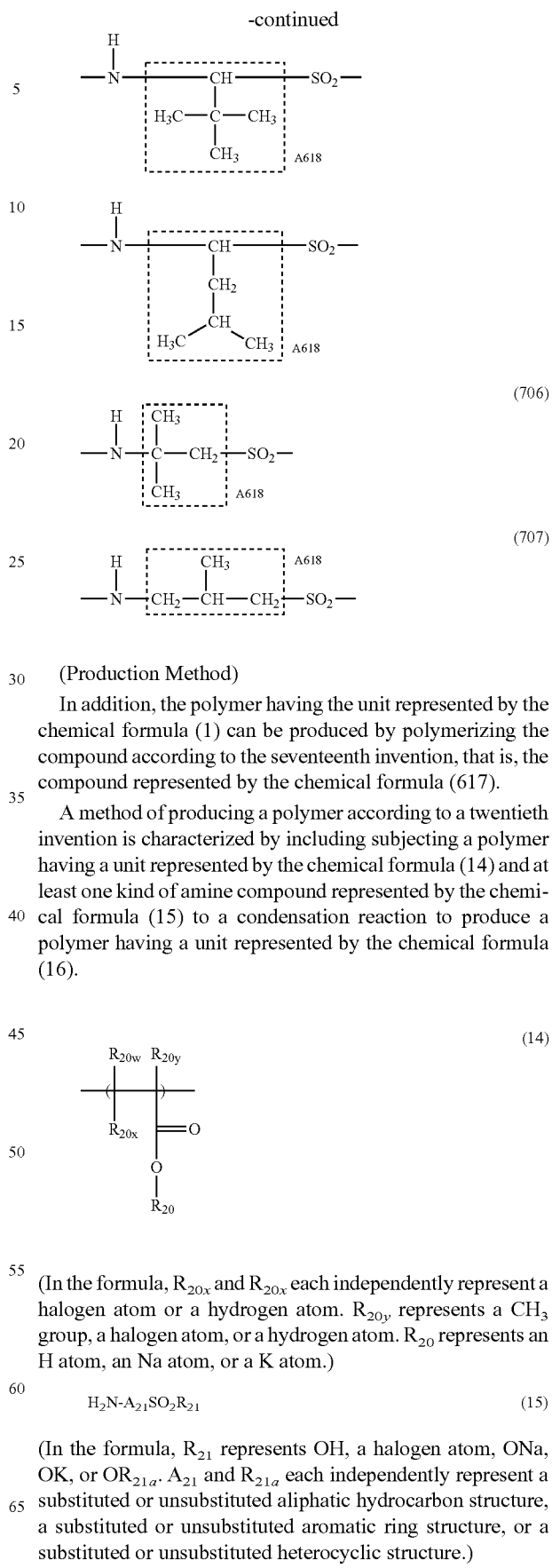

(Production Method)

In addition, the polymer having the unit represented by the chemical formula (1) can be produced by polymerizing the compound according to the seventeenth invention, that is, the compound represented by the chemical formula (617).

A method of producing a polymer according to a twentieth invention is characterized by including subjecting a polymer having a unit represented by the chemical formula (14) and at least one kind of amine compound represented by the chemical formula (15) to a condensation reaction to produce a polymer having a unit represented by the chemical formula (16).

(In the formula, $R_{20x}$ and $R_{20x}$ each independently represent a halogen atom or a hydrogen atom. $R_{20y}$ represents a $CH_3$ group, a halogen atom, or a hydrogen atom. $R_{20}$ represents an H atom, an Na atom, or a K atom.)

$$H_2N-A_{21}SO_2R_{21} \tag{15}$$

(In the formula, $R_{21}$ represents OH, a halogen atom, ONa, OK, or $OR_{21a}$. $A_{21}$ and $R_{21a}$ each independently represent a substituted or unsubstituted aliphatic hydrocarbon structure, a substituted or unsubstituted aromatic ring structure, or a substituted or unsubstituted heterocyclic structure.)

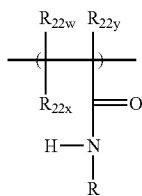

(16)

(In the formula, R represents -$A_{22}$-$SO_2R_{22}$. $R_{22w}$ and $R_{22x}$ each independently represent a halogen atom or a hydrogen atom. $R_{22y}$ represents a $CH_3$ group, a halogen atom, or a hydrogen atom. $R_{22}$ represents OH, a halogen atom, ONa, OK, or $OR_{22a}$. $A_{22}$ and $R_{22a}$ each independently represent a substituted or unsubstituted aliphatic hydrocarbon structure, a substituted or unsubstituted aromatic ring structure, or a substituted or unsubstituted heterocyclic structure.)

In the method of producing the polymer having the unit represented by the chemical formula (16), a condensation agent is preferably used to form an amide bond in an identical reaction field.

A phosphoric acid-based condensation agent can be used as the condensation agent in this case. For example, at least one selected from a phosphite-based condensation agent, a phosphorus chloride-based condensation agent, a phosphoric anhydride-based condensation agent, a phosphate-based condensation agent, and a phosphoric amide-based condensation agent can be used as the phosphoric acid-based condensation agent. In addition, the condensation reaction can be performed in the presence of pyridine.

A method of producing a polymer having a unit represented by the chemical formula (18) according to a twenty-fifth invention is characterized by including esterifying a polymer having a unit represented by the chemical formula (17) by using an esterifying agent to produce the polymer having the unit represented by the chemical formula (18).

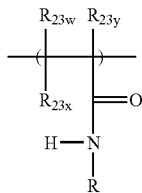

(17)

(In the formula, R represents -$A_{23}$-$SO_2R_{23}$. $R_{23w}$ and $R_{23x}$ each independently represent a halogen atom or a hydrogen atom. $R_{23y}$ represents a $CH_3$ group, a halogen atom, or a hydrogen atom. $R_{23}$ represents OH, a halogen atom, ONa, or OK. $A_{23}$ represents a substituted or unsubstituted aliphatic hydrocarbon structure, a substituted or unsubstituted aromatic ring structure, or a substituted or unsubstituted heterocyclic structure.)

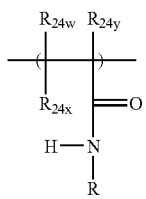

(18)

(In the formula, R represents -$A_{24}$-$SO_3R_{24}$. $R_{24w}$ and $R_{24x}$ each independently represent a halogen atom or a hydrogen atom. $R_{24y}$ represents a $CH_3$ group, a halogen atom, or a hydrogen atom. $A_{24}$ and $R_{24}$ each independently represent a substituted or unsubstituted aliphatic hydrocarbon structure, a substituted or unsubstituted aromatic ring structure, or a substituted or unsubstituted heterocyclic structure.)

Examples of the esterifying agent used in the method of producing the polymer having the unit represented by the chemical formula (18) include trimethylsilyldiazomethane, trimethyl orthoformate, and triethyl orthoformate.

Examples of an approach to synthesizing a sulfonic acid-containing polymer include an approach involving introducing a corresponding chemical structure into water-soluble polyacrylamide through an amide exchange reaction. In this approach, the acrylamide structure as a raw material may remain in a polymer to be obtained. Therefore, in this approach there is room for improvement. The present invention is more useful than the approach.

(Charge Control Agent)

A charge control agent for controlling a charged state of powder according to a twenty-eighth invention is characterized by including a polymer having a unit having a structure represented by the chemical formula (19).

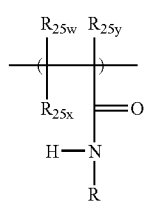

(19)

(In the formula, R represents -$A_{25}$-$SO_2R_{25}$. $R_{25w}$, $R_{25x}$, and $R_{25y}$ are selected from combinations described in the following items (i) and (ii). For the item (i), $A_{25}$ and $R_{25}$ are selected from combinations described in the following items (i-A) and (i-B). For the item (ii), $A_{25}$ and $R_{25}$ are selected from combinations described in the following item (ii-A).

(i) $R_{25w}$ and $R_{25x}$ each represent a hydrogen atom, and $R_{25y}$ represents a $CH_3$ group or a hydrogen atom.

(i-A) $A_{25}$ represents a substituted or unsubstituted aliphatic hydrocarbon structure. $R_{25}$ represents a halogen atom or $OR_{25a}$. $R_{25a}$ represents a substituted or unsubstituted aliphatic hydrocarbon structure, a substituted or unsubstituted aromatic ring structure, or a substituted or unsubstituted heterocyclic structure.

(i-B) $A_{25}$ represents a substituted or unsubstituted aromatic ring structure, or a substituted or unsubstituted heterocyclic structure. $R_{25}$ represents OH, a halogen atom, ONa, OK, or $OR_{25a}$. $R_{25a}$ represents a substituted or unsubstituted aliphatic hydrocarbon structure, a substituted or unsubstituted aromatic ring structure, or a substituted or unsubstituted heterocyclic structure.

(ii) $R_{25w}$ and $R_{25x}$ each independently represent a halogen atom or a hydrogen atom. $R_{25y}$ represents a $CH_3$ group, a halogen atom, or a hydrogen atom. At least one of $R_{25w}$, $R_{25x}$, and $R_{25y}$ represents a halogen atom.

(ii-A) $A_{25}$ represents a substituted or unsubstituted aliphatic hydrocarbon structure, a substituted or unsubstituted aromatic ring structure, or a substituted or unsubstituted heterocyclic structure. $R_{25}$ represents OH, a halogen atom, ONa, OK, or $OR_{25a}$. $R_{25a}$ represents a substituted or unsubstituted aliphatic hydrocarbon structure, a substituted or unsubstituted aromatic ring structure, or a substituted or unsubstituted heterocyclic structure.)

In addition, the powder is preferably a toner for developing an electrostatic charge image.

(Image Forming Method)

An image forming method according to a thirty-second invention is characterized by including the steps of: externally applying a voltage to a charging member to charge an electrostatic latent image-bearing member; forming an electrostatic charge image on the charged electrostatic latent image-bearing member; developing the electrostatic charge image with toner for developing an electrostatic charge image to form a toner image on the electrostatic latent image-bearing member; transferring the toner image on the electrostatic latent image-bearing member onto a recording material; and fixing the toner image on the recording material under heating. The image forming method is characterized in that the toner having the above constitution is used.

In the image forming method described above, a transferring step may be employed which is composed of two steps of: a first transferring step of transferring the toner image on the electrostatic latent image-bearing member onto an intermediate transfer member; and a second transferring step of transferring the toner image on the intermediate transfer member onto the recording material.

(Image Forming Apparatus)

An image forming apparatus according to a thirty-third invention is characterized by including the following means: means for externally applying a voltage to a charging member to charge an electrostatic latent image-bearing member; means for forming an electrostatic charge image on the charged electrostatic latent image-bearing member; means for developing the electrostatic charge image with toner for developing an electrostatic charge image to form a toner image on the electrostatic latent image-bearing member; means for transferring the toner image on the electrostatic latent image-bearing member onto a recording material; and means for fixing the toner image on the recording material under heating.

The image forming apparatus is characterized in that the toner for developing an electrostatic charge image is used for developing an electrostatic charge image.

The transferring means in the image forming apparatus may be composed of two means: a first transferring means for transferring the toner image on the electrostatic latent image-bearing member onto an intermediate transfer member and a second transferring means for transferring the toner image on the intermediate transfer member onto the recording material.

(More Specific Method of Producing Polymer According to the Present Invention)

Hereinafter, the present invention will be described in more detail by way of preferred embodiments. The polymer according to the present invention having each of the structures described above shows very excellent properties as a charge control agent, and has a high safety for a human body and environments. Furthermore, the polymer shows a remarkable advantage when used in toner for developing an electrostatic charge image, containing the charge control agent. The toner for developing an electrostatic charge image also shows a remarkable advantage when used in an image forming apparatus having a certain developing system. The following method can be exemplified for a method of producing the polymer.

For example, a polymer having a unit represented by the chemical formula (16) can be produced by a reaction of a polymer having a unit represented by the chemical formula (14) to be used as a starting material with at least one compound represented by the chemical formula (15).

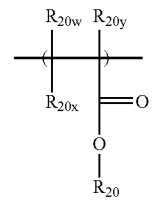

(14)

(In the formula, $R_{20w}$ and $R_{20x}$ each independently represent a halogen atom or a hydrogen atom. $R_{20y}$ represents a $CH_3$ group, a halogen atom, or a hydrogen atom. $R_{20}$ represents an H atom, a Na atom, or a K atom. When multiple units exist, $R_{20}$, $R_{20w}$, $R_{20x}$, and $R_{20y}$ each independently have the above meaning for each unit.)

$$H_2N-A_{21}-SO_2R_{21} \quad (15)$$

(In the formula, $R_{21}$ represents OH, a halogen atom, ONa, OK, or $OR_{21a}$. $A_{21}$ and $R_{21a}$ each independently represent a substituted or unsubstituted aliphatic hydrocarbon structure, a substituted or unsubstituted aromatic ring structure, or a substituted or unsubstituted heterocyclic structure.)

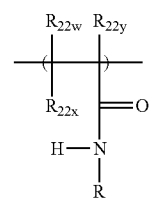

(16)

(In the formula, R represents $-A_{22}-SO_2R_{22}$. $R_{22w}$ and $R_{22x}$ each independently represent a halogen atom or a hydrogen atom. $R_{22y}$ represents a $CH_3$ group, a halogen atom, or a hydrogen atom. $R_{22}$ represents OH, a halogen atom, ONa, OK, or $OR_{22a}$. $A_{22}$ and $R_{22a}$ each independently represent a substituted or unsubstituted aliphatic hydrocarbon structure, a substituted or unsubstituted aromatic ring structure, or a substituted or unsubstituted heterocyclic structure. When multiple units exist, R, $A_{22}$, $R_{22}$, $R_{22a}$, $R_{22w}$, $R_{22x}$, and $R_{22y}$ each independently have the above meaning for each unit.)

(Method of Producing Polymer Having Unit Represented by Chemical Formula (14))

A polymer having a carboxyl group represented by the chemical formula (14) can be produced as a copolymer having a vinyl-based monomer unit represented by the chemical formula (108) in addition to the chemical formula (14) by using a conventionally known polymerization method and polymer reaction.

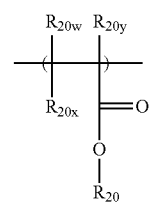

(14)

(In the formula, $R_{20w}$ and $R_{20x}$ each independently represent a halogen atom or a hydrogen atom. $R_{20y}$ represents a $CH_3$ group, a halogen atom, or a hydrogen atom. $R_{20}$ represents an H atom, an Na atom, or a K atom. When multiple units exist, $R_{20}$, $R_{20w}$, $R_{20x}$, and $R_{20y}$ each independently have the above meaning for each unit.)

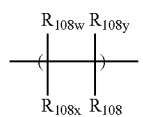

(108)

(In the formula, $R_{108w}$ and $R_{108x}$ each independently represent a halogen atom or a hydrogen atom, and $R_{108y}$ represents a $CH_3$ group, a halogen atom, or a hydrogen atom. $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{108a}$, —O—$R_{108b}$, —COO—$R_{108c}$, —OCO—$R_{108d}$, —CONR$_{118e}$R$_{108f}$, —CN, or a ring structure containing an N atom. $R_{108a}$, $R_{108b}$, $R_{108c}$, $R_{108d}$, $R_{108e}$, and $R_{108f}$ each represent a hydrogen atom, a substituted or unsubstituted aliphatic hydrocarbon structure, a substituted or unsubstituted aromatic ring structure, or a substituted or unsubstituted heterocyclic structure. When multiple units exist, $R_{108}$, $R_{108a}$, $R_{108b}$, $R_{108c}$, $R_{108d}$, $R_{108e}$, $R_{108f}$, $R_{108w}$, $R_{108x}$, and $R_{108y}$ each independently have the above meaning for each unit.)

Examples of the vinyl-based monomer represented by the chemical formula (108) include: styrene and derivatives thereof such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, and p-n-dodecylstyrene; ethylene unsaturated monoolefins such as ethylene, propylene, butylene, and isobutylene; halogenated vinyls such as vinyl chloride, vinylidene chloride, vinyl bromide, and vinyl fluoride; vinyl esters such as vinyl acetate, vinyl propionate, and vinyl benzoate; α-methylene aliphatic monocarboxylates such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, and diethylaminoethyl methacrylate; acrylates such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, and phenyl acrylate; vinyl ethers such as vinyl methyl ether, vinyl ethyl ether, and vinyl isobutyl ether; vinyl ketones such as vinyl methyl ketone, vinyl hexyl ketone, and methyl isopropenyl ketone; N-vinyl compounds such as N-vinylpyrrole, N-vinylcarbazole, N-vinylindole, and N-vinylpyrrolidone; vinyl naphthalenes; and acrylic/methacrylic acid derivatives such as acrylonitrile, methacrylonitrile, and acrylamide.

As an example of a polymer having a carboxyl group represented by the chemical formula (14), a copolymer of methacrylate and methacrylic acid or a copolymer of acrylate and acrylic acid having a carboxyl group obtained by partially hydrolyzing a homopolymer of methacrylate or acrylate may be cited.

In addition, a copolymer of another polymerizable monomer and an acrylate or methacrylate is synthesized, and is deesterified in the same manner as that described above, whereby a copolymer having a carboxyl group can be easily obtained.

A copolymer having a carboxyl group can also be obtained by directly polymerizing acrylic acid or methacrylic acid and another polymerizable monomer.

(Compound Represented by Chemical Formula (15))

An example of the compound represented by the chemical formula (15) to be used in the present invention includes the following.

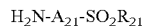

$$H_2N-A_{21}-SO_2R_{21} \quad (15)$$

(In the formula, $R_{21}$ represents OH, a halogen atom, ONa, OK, or $OR_{21a}$. $A_{21}$ and $R_{21a}$ each independently represent a substituted or unsubstituted aliphatic hydrocarbon structure, a substituted or unsubstituted aromatic ring structure, or a substituted or unsubstituted heterocyclic structure.) More specifically, $A_{21}$ represents a linear or branched alkylene group having 1 to 8 carbon atoms, a substituted or unsubstituted phenyl group, a substituted or unsubstituted naphthyl group, or a substituted or unsubstituted heterocyclic structure containing one or more of N, S, and O. When $A_{21}$ represents a ring structure, an unsubstituted ring may be further condensed.

Specific examples of the linear or branched alkylene group having 1 to 8 carbon atoms represented by $A_{21}$ include 2-aminoethanesulfonic acid (taurine), 3-aminopropanesulfonic acid, 4-aminobutanesulfonic acid, 2-amino-2-methylpropanesulfonic acid, and alkali metals thereof.

When $A_{21}$ represents a substituted or unsubstituted phenyl group, the compound is represented by the chemical formula (26).

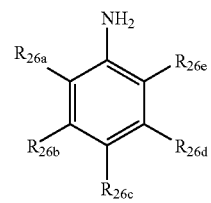

(26)

(In the formula, at least one of $R_{26a}$, $R_{26b}$, $R_{26c}$, $R_{26d}$, and $R_{26e}$ represents $SO_2R_{26f}$ ($R_{26f}$ represents OH, a halogen atom, ONa, OK, or $OR_{26h}$. $R_{26h}$ represents a substituted or unsubstituted aliphatic hydrocarbon structure, a substituted or unsubstituted aromatic ring structure, or a substituted or unsubstituted heterocyclic structure). $R_{26a}$, $R_{26b}$, $R_{26c}$, $R_{26d}$, and $R_{26e}$ are each independently selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{26g}$ ($R_{26g}$ represents an H atom, an Na atom, or a K atom), an acetamide group, an OPh group, an NHPh group, a $CF_3$ group, a $C_2F_5$ group, and a $C_3F_7$ group.)

Examples of the compound represented by the chemical formula (26) include: various aminobenzenesulfonic acid derivatives and salts thereof such as p-aminobenzenesulfonic acid (sulfanilic acid), m-aminobenzenesulfonic acid, o-aminobenzenesulfonic acid, m-toluidine-4-sulfonic acid, o-toluidine-4-sulfonic acid sodium salt, p-toluidine-2-sulfonic acid, 4-methoxyaniline-2-sulfonic acid, o-anisidine-5-sulfonic acid, p-anisidine-3-sulfonic acid, 3-nitroaniline-4-sulfonic acid, 2-nitroaniline-4-sulfonic acid sodium salt, 4-nitroaniline-2-sulfonic acid sodium salt, 1,5-dinitroaniline-4-sulfonic acid, 2-aminophenol-4-hydroxy-5-nitrobenzenesulfonic acid, 2,4-dimethylaniline-5-sulfonic acid sodium salt, 2,4-dimethylaniline-6-sulfonic acid, 3,4-dimethylaniline-5-sulfonic acid, 4-isopropylaniline-6-sulfonic acid, 4-trifluoromethylaniline-6-sulfonic acid, 3-carboxy-4-hydroxyaniline-5-sulfonic acid, and 4-carboxyaniline-6-sulfonic acid; and esterified products such as methyl esterified products and phenyl esterified products of various aminobenzenesulfonic acid derivatives and salts thereof such as 2-aminobenzenesulfonic acid methyl ester, 4-aminobenzenesulfonic acid methyl ester, 2-aminobenzenesulfonic acid phenyl ester, and 4-aminobenzenesulfonic acid phenyl ester.

When $A_{27}$ represents a substituted or unsubstituted naphthyl group, the compound is represented by the chemical formula (27a) or (27b).

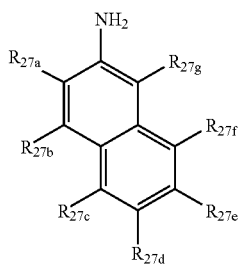

(27a)

(In the formula, at least one of $R_{27a}$, $R_{27b}$, $R_{27c}$, $R_{27d}$, $R_{27e}$, $R_{27f}$ and $R_{27g}$ represents $SO_2R_{27o}$ ($R_{27o}$ represents OH, a halogen atom, ONa, OK, or $OR_{27s}$. $R_{27s}$ represents a substituted or unsubstituted aliphatic hydrocarbon structure, a substituted or unsubstituted aromatic ring structure, or a substituted or unsubstituted heterocyclic structure). $R_{27a}$, $R_{27b}$, $R_{27c}$, $R_{27d}$, $R_{27e}$, $R_{27f}$ and $R_{27g}$ are each independently selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{27p}$ ($R_{27p}$ represents an H atom, an Na atom, or a K atom), an acetamide group, an OPh group, an NHPh group, a $CF_3$ group, a $C_2F_5$ group, and a $C_3F_7$ group.)

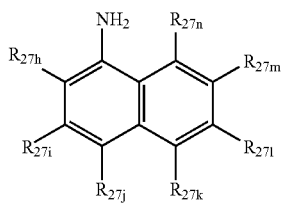

(27b)

(In the formula, at least one of $R_{27h}$, $R_{27i}$, $R_{27j}$, $R_{27k}$, $R_{27l}$, $R_{27m}$, and $R_{27n}$ represents $SO_2R_{27q}$ ($R_{27q}$ represents OH, a halogen atom, ONa, OK, or $OR_{27t}$. $R_{27t}$ represents a substituted or unsubstituted aliphatic hydrocarbon structure, a substituted or unsubstituted aromatic ring structure, or a substituted or unsubstituted heterocyclic structure). $R_{27h}$, $R_{27i}$, $R_{27j}$, $R_{27k}$, $R_{27l}$, $R_{27m}$, and $R_{27n}$ in are each independently selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{27r}$ ($R_{27r}$ represents an H atom, an Na atom, or a K atom), an acetamide group, an OPh group, an NHPh group, a $CF_3$ group, a $C_2F_5$ group, and a $C_3F_7$ group.)

Examples of the compound represented by the chemical formula (27a) or (27b) include: various naphthylaminesulfonic acid derivatives and salts thereof such as 1-naphthylamine-4-sulfonic acid, 1-naphthylamine-5-sulfonic acid, 1-naphthylamine-6-sulfonic acid, 1-naphthylamine-7-sulfonic acid, 1-naphthylamine-8-sulfonic acid, 2-naphthylamine-1-sulfonic acid, 2-naphthylamine-5-sulfonic acid, 1-naphthylamine-2-ethoxy-6-sulfonic acid, 1-amino-2-naphthol-4-sulfonic acid, 6-amino-1-naphthol-3-sulfonic acid, 1-amino-8-naphthol-2,4-disulfonic acid Monosodium salt, and 1-amino-8-naphthol-3,6-disulfonic acid Monosodium salt; and esterified products such as methyl esterified products and phenyl esterified products of various naphthylaminesulfonic acid derivatives and salts thereof such as 1-naphthylamine-8-sulfonic acid methyl ester, 2-naphthylamine-1-sulfonic acid methyl ester, 1-naphthylamine-8-sulfonic acid phenyl ester, and 2-naphthylamine-1-sulfonic acid phenyl ester.

When $A_{25}$ represents a substituted or unsubstituted heterocyclic structure containing one or more of N, S, and O, examples of the ring include a pyridine ring, a piperazine ring, a furan ring, and a thiol ring.

(Method of Producing Polymer Having One or More Units Each Represented by Chemical Formula (16) in Molecule)

A condensation reaction of a polymer having a unit represented by the chemical formula (14) with an aminosulfonic acid compound represented by the chemical formula (15) in the present invention will be described below in detail.

Examples of an available method for a condensation reaction of a carboxyl group with an amino group include: a method which involves using a condensation agent; a method which involves forming a salt and performing condensation through a dehydration reaction; and a method which involves using a dehydrating agent.

A method which involves using a condensation agent as a production method of the present invention will be described in detail.

A phosphoric acid-based condensation agent, a carbodiimide-based condensation agent, or the like can be used as the condensation agent. Examples of an available phosphoric acid-based condensation agent include a phosphite-based condensation agent, a phosphorus chloride-based condensation agent, a phosphoric anhydride-based condensation agent, a phosphate-based condensation agent, and a phosphoric amide-based condensation agent. A phosphite-based condensation agent is preferably used in the reaction in the present invention. Examples of a phosphite used herein include triphenyl phosphite, trimethyl phosphite, triethyl phosphite, diphenyl phosphite, tri-o-tolyl phosphite, di-o-tolyl phosphite, tri-m-tolyl phosphite, di-m-tolyl phosphite, tri-p-tolyl phosphite, di-p-tolyl phosphite, di-o-chlorophenyl phosphite, tri-p-chlorophenyl phosphite, and di-p-chlorophenyl phosphite. Of these, triphenyl phosphite is preferably used.

The amount of the condensation agent to be used is 0.1-fold mole or more, or preferably 1-time mole or more with respect to the compound represented by the chemical formula (15).

A condensation agent itself can also be used as a reaction solvent.

The amount of the compound represented by the chemical formula (15) to be used in the method is in the range of 0.1 to 50.0-fold moles, or preferably 1.0 to 20.0-fold moles with respect to the unit represented by the chemical formula (14) to be used as a starting material. A solvent may be used as required in the reaction in the present invention. Examples of the usable solvent include: hydrocarbons such as hexane, cyclohexane and heptane; ketones such as acetone and methyl ethyl ketone; ethers such as dimethyl ether, diethyl ether and tetrahydrofuran; halogenated hydrocarbons such as dichloromethane, chloroform, carbon tetrachloride, dichloroethane and trichloroethane; aromatic hydrocarbons such as benzene and toluene; aprotic polar solvents such as N,N-dimethylformamide and dimethyl sulfoxide; and pyridine derivatives. Pyridine is particularly preferably used. The amount of the solvent to be used can be appropriately determined in accordance with kinds of starting materials and bases, a reaction condition, and the like.

A reaction temperature is not particularly limited in the method, but is generally in the range of 0° C. to the boiling point of a solvent. However, it is preferable to perform the reaction at an optimum temperature suited for a condensation agent to be used. In the method of the present invention, a reaction time is in the range of, for example, 1 to 48 hours. The solvent can be removed from the reaction solution thus produced containing a polymer having one or more units each represented by the chemical formula (16) in its molecule by an ordinary method such as distillation. Alternatively, using a solvent, for example, water, an alcohol such as methanol or ethanol, or an ether such as dimethyl ether, diethyl ether, or tetrahydrofuran, the target polymer having one or more units each represented by the chemical formula (16) can be re-precipitated and recovered by uniformly mixing a solvent that does not dissolve that polymer with the solution. The resultant polymer having one or more units each represented by the chemical formula (16) in its molecule can be subjected to isolation purification as required. A method for the isolation purification is not particularly limited, and includes a method involving reprecipitation using a solvent that does not dissolve the polymer having one or more units each represented by the chemical formula (16) in its molecule, a method according to column chromatography, or the like.

In addition, out of the polymers each having one or more units each represented by the chemical formula (16), a polymer having one or more units each represented by the chemical formula (1) can be synthesized by copolymerization using a compound represented by the chemical formula (617), another polymerizable monomer, and a polymerization initiator.

(Method of Producing Compound Represented by Chemical Formula (617))

The compound represented by the chemical formula (617) shown in the seventeenth invention can be produced according to the following method.

A method of synthesizing the compound represented by the chemical formula (617) in the present invention will be described in detail. The compound is synthesized by a condensation reaction among: a polymerizable monomer having a carboxyl group such as methacrylic acid or acrylic acid; an acid chloride polymerizable monomer in which a carboxyl group is transformed into an acid chloride such as acrylic chloride or methacrylic chloride; and various compounds having amino groups represented by the chemical formula (817) described below.

Examples of an available method for a condensation reaction between a carboxyl group and an amino group include: a method which involves using a condensation agent; a method which involves forming a salt and performing condensation through a dehydration reaction; a method which involves using a dehydrating agent; and a method which involves transforming a carboxyl group into an acid chloride and allowing an amino group to react with it.

A method which involves transforming a carboxyl group into an acid chloride and allowing an amino group to react with it as a production method according to the present invention will be described below in detail.

Transformation of a polymerizable monomer represented by the chemical formula (717) into an acid chloride can be performed by an ordinary method using thionyl chloride.

(717)

(In the formula, $R_{717w}$ and $R_{717x}$ each independently represent a halogen atom or a hydrogen atom. $R_{717y}$ represents a $CH_3$ group, a halogen atom, or a hydrogen atom. $R_{717}$ represents an H atom, an Na atom, or a K atom. When multiple units exist, $R_{717}$, $R_{717w}$, $R_{717x}$, and $R_{717y}$ each independently have the above meaning for each unit.)

The amount of thionyl chloride to be used is in the range of 0.1 or 50.0 times mole, or preferably 1.0 to 20.0-fold moles with respect to the compound represented by the chemical formula (717). PS Thionyl chloride itself can also be used as a reaction solvent.

The amount of a compound represented by the chemical formula (817) described below to be used in the method is in the range of 0.1 or 50.0-fold moles, or preferably 1.0 to 20.0-fold moles with respect to the compound represented by the chemical formula (717). A solvent can be used as required in the reaction of the present invention. Examples of the solvent to be used include: hydrocarbons such as hexane, cyclohexane, and heptane; ketones such as acetone and methyl ethyl ketone; ethers such as dimethyl ether, diethyl ether, and tetrahydrofuran; halogenated hydrocarbons such as dichloromethane, chloroform, carbon tetrachloride, dichloroethane, and trichloroethane; aromatic hydrocarbons such as benzene and toluene; aprotic polar solvents such as N,N-dimethylformamide and dimethyl sulfoxide; pyridine derivatives; and water. The solvent is preferably soluble in the compound represented by the chemical formula (817) described below. The amount of the solvent to be used can be appropriately determined in accordance with starting materials, reaction conditions, and the like.

A reaction temperature is not particularly limited in the method, but is generally in the range of −30° C. to the boiling point of a solvent. However, it is preferable to perform the reaction at an optimum temperature suited for the compound represented by the chemical formula (817) described below and a reaction solvent. In the method of the present invention, a reaction time, which cannot be uniquely determined is generally in the range of 1 to 48 hours. A reaction solution thus produced containing the compound represented by the chemical formula (617) can be removed by an ordinary method such as distillation.

The resultant compound represented by the chemical formula (617) can be subjected to isolation purification as required. A method for the isolation purification is not particularly limited, and includes a method involving recrystallization using a solvent in which the compound represented by the chemical formula (617) is hardly soluble, a method according to column chromatography, or the like.

(Compound Represented by Chemical Formula (817))

An example of the compound represented by the chemical formula (817) to be used in the present invention includes the following.

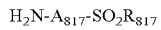

(817)

(In the formula, $R_{817}$ represents OH, a halogen atom, ONa, OK, or $OR_{817a}$. $A_{817}$ and $R_{817a}$ each independently represent a substituted or unsubstituted aliphatic hydrocarbon structure, a substituted or unsubstituted aromatic ring structure, or a substituted or unsubstituted heterocyclic structure.)

More specifically, $A_{817}$ represents a linear or branched alkylene group having 1 to 8 carbon atoms, a substituted or unsubstituted phenyl group, a substituted or unsubstituted naphthyl group, or a substituted or unsubstituted heterocyclic structure containing one or more of N, S, and O. When $A_{817}$ represents a ring structure, an unsubstituted ring may be further condensed.

Examples of the linear or branched alkylene group having 1 to 8 carbon atoms represented by $A_{817}$ include 2-aminoethanesulfonic acid (taurine), 3-aminopropanesulfonic acid, 4-aminobutanesulfonic acid, 2-amino-2-methylpropanesulfonic acid, and alkali metal salts thereof.

When $A_{817}$ represents a substituted or unsubstituted phenyl group, the compound is represented by the chemical formula (26).

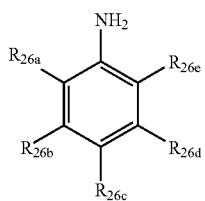

(26)

(In the formula, at least one of $R_{26a}$, $R_{26b}$, $R_{26c}$, $R_{26d}$, and $R_{26e}$ represents $SO_2R_{26f}$ ($R_{26f}$ represents OH, a halogen atom, ONa, OK, or $OR_{26h}$. $R_{26h}$ represents a substituted or unsubstituted aliphatic hydrocarbon structure, a substituted or unsubstituted aromatic ring structure, or a substituted or unsubstituted heterocyclic structure). $R_{26a}$, $R_{26b}$, $R_{26c}$, $R_{26d}$, and $R_{26e}$ are each independently selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{26g}$ ($R_{26g}$ represents an H atom, an Na atom, or a K atom), an acetamide group, an OPh group, an NHPh group, a $CF_3$ group, a $C_2F_5$ group, and a $C_3F_7$ group.)

Examples of the compound represented by the chemical formula (26) include: various aminobenzenesulfonic acid derivatives and salts thereof such as p-aminobenzenesulfonic acid (sulfanilic acid), m-aminobenzenesulfonic acid, o-aminobenzenesulfonic acid, m-toluidine-4-sulfonic acid, o-toluidine-4-sulfonic acid sodium salt, p-toluidine-2-sulfonic acid, 4-methoxyaniline-2-sulfonic acid, o-anisidine-5-sulfonic acid, p-anisidine-3-sulfonic acid, 3-nitroaniline-4-sulfonic acid, 2-nitroaniline-4-sulfonic acid sodium salt, 4-nitroaniline-2-sulfonic acid sodium salt, 1,5-dinitroaniline-4-sulfonic acid, 2-aminophenol-4-hydroxy-5-nitropenzenesulfonic acid, 2,4-dimethylaniline-5-sulfonic acid sodium salt, 2,4-dimethylaniline-6-sulfonic acid, 3,4-dimethylaniline-5-sulfonic acid, 4-isopropylaniline-6-sulfonic acid, 4-trifluoromethylaniline-6-sulfonic acid, 3-carboxy-4-hydroxyaniline-5-sulfonic acid, and 4-carboxyaniline-6-sulfonic acid; and esterified products such as methyl esterified products and phenyl esterified products of various aminobenzenesulfonic acid derivatives and salts thereof such as 2-aminobenzenesulfonic acid methyl ester, 4-aminobenzenesulfonic acid methyl ester, 2-aminobenzenesulfonic acid phenyl ester, and 4-aminobenzenesulfonic acid phenyl ester.

When $A_{817}$ represents a substituted or unsubstituted naphthyl group, the compound is represented by the chemical formula (27a) or (27b).

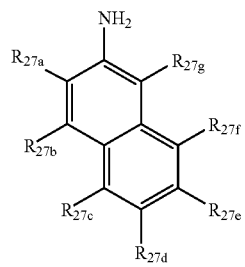

(27a)

(In the formula, at least one of $R_{27a}$, $R_{27b}$, $R_{27c}$, $R_{27d}$, $R_{27e}$, $R_{27f}$, and $R_{27g}$ represents $SO_2R_{27o}$ ($R_{27o}$ represents OH, a halogen atom, ONa, OK, or $OR_{27s}$. $R_{27s}$ represents a substituted or unsubstituted aliphatic hydrocarbon structure, a substituted or unsubstituted aromatic ring structure, or a substituted or unsubstituted heterocyclic structure). $R_{27a}$, $R_{27b}$, $R_{27c}$, $R_{27d}$, $R_{27e}$, $R_{27f}$, and $R_{27g}$ are each independently selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{27p}$ ($R_{27p}$ represents an H atom, an Na atom, or a K atom), an acetamide group, an OPh group, an NHPh group, a $CF_3$ group, a $C_2F_5$ group, and a $C_3F_7$ group.)

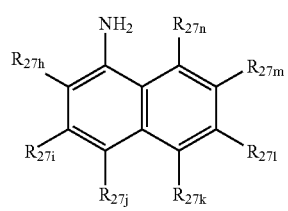

(27b)

(In the formula, at least one of $R_{27h}$, $R_{27i}$, $R_{27j}$, $R_{27k}$, $R_{27l}$, $R_{27m}$, and $R_{27n}$ represents $SO_2R_{27q}$ ($R_{27q}$ represents OH, a halogen atom, ONa, OK, or $OR_{27t}$. $R_{27t}$ represents a substituted or unsubstituted aliphatic hydrocarbon structure, a substituted or unsubstituted aromatic ring structure, or a substituted or unsubstituted heterocyclic structure). $R_{27h}$, $R_{27i}$, $R_{27j}$, $R_{27k}$, $R_{27l}$, $R_{27m}$, and $R_{27n}$ are each independently selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{27r}$ ($R_{27r}$ represents an H atom, an Na atom, or a K atom), an acetamide group, an OPh group, an NHPh group, a $CF_3$ group, a $C_2F_5$ group, and a $C_3F_7$ group.)

Examples of the compound represented by the chemical formula (27a) or (27b) include: various naphthylamine-sulfonic acid derivatives and salts thereof such as 1-naphthylamine-4-sulfonic acid, 1-naphthylamine-5-sulfonic acid, 1-naphthylamine-6-sulfonic acid, 1-naphthylamine-7-sulfonic acid, 1-naphthylamine-8-sulfonic acid, 2-naphthylamine-1-sulfonic acid, 2-naphthylamine-5-sulfonic acid, 1-naphthylamine-2-ethoxy-6-sulfonic acid, 1-amino-2-naphthol-4-sulfonic acid, 6-amino-1-naphthol-3-sulfonic acid, 1-amino-8-naphthol-2,4-disulfonic acid Monosodium salt, and 1-amino-8-naphthol-3,6-disulfonic acid Monosodium salt; and esterified products such as methyl esterified products and phenyl esterified products of various naphthylaminesulfonic acid derivatives and salts thereof such as 1-naphthylamine-8-sulfonic acid methyl ester, 1-naphthylamine-1-sulfonic acid methyl ester, 1-naphthylamine-8-sulfonic acid phenyl ester, and 2-naphthylamine-1-sulfonic acid phenyl ester.

When $A_{817}$ represents a substituted or unsubstituted heterocyclic structure containing one or more of N, S, and O, examples of the ring include a pyridine ring, a piperazine ring, a furan ring, and a thiol ring.

In addition, in the case where out of the compounds each represented by the chemical formula (617), a compound having no sulfonate unit, for example, a compound in which $R_{617}$ represents OH, a halogen atom, ONa, or OK is synthesized, a compound represented by the chemical formula (617) having a sulfonate unit can be synthesized by further using an esterifying agent such as trimethylsilyldiazomethane, trimethyl orthoformate, or triethyl orthoformate. The reaction will be described below in detail.

A solvent can be used as required in the reaction. Examples of the solvent to be used include: hydrocarbons such as hexane, cyclohexane, and heptane; alcohols such as methanol and ethanol; ethers such as dimethyl ether, diethyl ether, tetrahydrofuran, and dioxane; halogenated hydrocarbons such as dichloromethane, chloroform, carbon tetrachloride, dichloroethane, and trichloroethane; aromatic hydrocarbons such as benzene and toluene; aprotic polar solvents such as N,N-dimethylformamide and dimethyl sulfoxide; and pyridine derivatives. Chloroform or methanol is particularly preferably used. The amount of the solvent to be used can be appropriately determined in accordance with starting materials, reaction condition, and the like.

The amount of the esterifying agent to be used is in the range of 0.1 or 50-fold moles, or preferably 1 to 20-fold moles with respect to the no sulfonate unit which $R_{617}$ in the chemical formula (617) represents OH, a halogen atom, ONa, or OK.

A reaction temperature is not particularly limited in the method, but is generally in the range of −20° C. to 30° C. A reaction time, which cannot be uniquely determined, is generally in the range of 1 to 48 hours.

A reaction solution thus produced containing the compound represented by the chemical formula (617) having a sulfonate unit can be removed by an ordinary method such as distillation.

The resultant compound represented by the chemical formula (617) having a sulfonate unit can be subjected to isolation purification as required. A method for the isolation purification is not particularly limited, and includes a method involving recrystallization using a solvent in which the compound represented by the chemical formula (617) having a sulfonate unit is hardly soluble, a method according to column chromatography, or the like.

(Method of Polymerizing Compound Represented by Chemical Formula (617))

Any one of various conventionally known polymerization reactions can be used for a method of polymerizing a compound represented by the chemical formula (617). The compound can also be copolymerized with any one of various conventionally known monomers.

Examples of a copolymerizable monomer include: styrene and derivatives thereof such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, and p-n-dodecylstyrene; ethylene unsaturated monoolefins such as ethylene, propylene, butylene, and isobutylene; halogenated vinyls such as vinyl chloride, vinylidene chloride, vinyl bromide, and vinyl fluoride; vinyl esters such as vinyl acetate, vinyl propionate, and vinyl benzoate; α-methylene aliphatic monocarboxylates such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, and diethylaminoethyl methacrylate; acrylates such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, and phenyl acrylate; vinyl ethers such as vinyl methyl ether, vinyl ethyl-ether, and vinyl isobutyl ether; vinyl ketones such as vinyl methyl ketone, vinyl hexyl ketone, and methyl isopropenyl ketone; N-vinyl compounds such as N-vinylpyrrole, N-vinylcarbazole, N-vinylindole, and N-vinylpyrrolidone; vinyl naphthalenes; and acrylic/methacrylic acid derivatives such as acrylonitrile, methacrylonitrile, and acrylamide.

In the case where out of the compounds each represented by the chemical formula (617), a compound having no sulfonate unit, for example, a compound in which $R_{617}$ represents OH, a halogen atom, ONa, or OK is polymerized, radical polymerization can be particularly preferably used because the conditions for the polymerization can be relatively easily controlled.

When the compound has a sulfonate unit, ion polymerization can also be used.

Examples of an initiator for radical polymerization include t-butylperoxy-2-ethylhexanoate, cumine perpivarate, t-butylperoxylaurate, benzoyl peroxide, lauroyl peroxide, octanoyl peroxide, di-t-butyl peroxide, t-butylcumyl peroxide, dicumyl-peroxide, 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1-bis(t-butylperoxy)3,3,5-trimethylcyclohexane, 1,1-bis(t-butylperoxy)cyclohexane, 1,4-bis(t-butylperoxycarbonyl)cyclohexane, 2,2-bis(t-butylperoxy)octane, n-butyl 4,4-bis(t-butylperoxy)valerate, 2,2-bis(t-butylperoxy)butane, 1,3-bis(t-butylperoxy-isopropyl)benzene, 2,5-dimethyl-2,5-di(t-butylperoxy)hexane, 2,5-dimethyl-2,5-di(benzoylperoxy)hexane, di-t-butyldiperoxyisophthalate, 2,2-bis(4,4-di-t-butylperoxycyclohexyl)propane, di-t-butylperoxy α-methylsuccinate, di-t-butylperoxydimethylglutarate, di-t-butylperoxyhexahydroterephthalate, di-t-butylperoxyazelate, diethylene glycol-bis(t-butylperoxycarbonate), di-t-butylperoxytrimethyladipate, tris(t-butylperoxy)triazine, and vinyl tris(t-butylperoxy)silane. A water-soluble initiator such as potassium persulfate or ammonium persulfate can also be used.

The above initiators can be used alone or in combination.

The amount of the initiator used, which is preferably in the range of 0.0001 to 0.5-fold mole with respect to the total amount of the polymerizable monomer, can be appropriately determined in accordance with the kind of monomer to be used, monomer to be used for copolymerization, and initiator to be used.

A solvent may be used as required in the polymerization reaction of the present invention. Examples of the solvent to be used include: hydrocarbons such as hexane, cyclohexane, and heptane; ketones such as acetone and methyl ethyl ketone; ethers such as dimethyl ether, diethyl ether, and tetrahydrofuran; halogenated hydrocarbons such as dichloromethane, chloroform, carbon tetrachloride, dichloroethane, and trichloroethane; aromatic hydrocarbons such as benzene and toluene; and aprotic polar solvents such as N,N-dimethylformamide and dimethyl sulfoxide. Aprotic polar solvents such as N,N-dimethylformamide and dimethyl sulfoxide are particularly preferably used. The amount of the solvent to be used can be appropriately determined in accordance with the kind of solvent, monomer to be used for copolymerization, initiator to be used, a reaction condition, and the like.

A reaction temperature is not particularly limited in the method, but is generally in the range of −76° C. to the boiling point of a solvent. However, it is desirable to perform the reaction at an optimum temperature suited for an initiator to be used and a monomer to be used for copolymerization. In the method of the present invention, a reaction time, which cannot be uniquely determined, is generally in the range of 0.5 to 48 hours. The solvent can be removed from the reaction solution thus produced containing a polymer having one or more units each represented by the chemical formula (1) in its molecule by an ordinary method such as distillation. Alternatively, using a solvent, for example, water, an alcohol such as methanol or ethanol, or an ether such as dimethyl ether, diethyl ether, or tetrahydrofuran, the target polymer having one or more units each represented by the chemical formula (1) in its molecule can be re-precipitated and recovered by uniformly mixing a solvent that does not dissolved that polymer with the reaction solution. The resultant polymer having one or more units each represented by the chemical formula (1) in its molecule can be subjected to isolation purification as required. A method for the isolation purification is not particularly limited, and includes a method involving reprecipitation using a solvent that does not dissolve the polymer having one or more units each represented by the chemical formula (1) in its molecule, a method according to column chromatography, or the like.

(Method of Producing Polymer Having One or More Units Each Represented by Chemical Formula (18) in Molecule)

As shown in the chemical formula (17), when $R_1$ in the chemical formula (17) represents OH, a halogen atom, ONa, or OK, a polymer in which R in the chemical formula (18) represents -$A_{24}$-$SO_3R_{24}$ can be synthesized by using trimethylsilyldiazomethane, trimethyl orthoformate, or triethyl orthoformate as an esterifying agent. The reaction will be described below in detail.

A solvent can be used as required in the reaction. Examples of the solvent to be used include: hydrocarbons such as hexane, cyclohexane, and heptane; alcohols such as methanol and ethanol; ethers such as dimethyl ether, diethyl ether, tetrahydrofuran, and dioxane; halogenated hydrocarbons such as dichloromethane, chloroform, carbon tetrachloride, dichloroethane, and trichloroethane; aromatic hydrocarbons such as benzene and toluene; aprotic polar solvents such as N,N-dimethylformamide and dimethyl sulfoxide; and pyridine derivatives. Chloroform or methanol is particularly preferably used. The amount of the solvent to be used can be appropriately determined in accordance with starting materials, reaction condition, and the like.

The amount of the esterifying agent to be used is in the range of 0.1 or 50-fold moles, or preferably 1 to 20-fold moles with respect to the unit represented by the chemical formula (17).

A reaction temperature is not particularly limited in the method, but is generally in the range of −20° C. to 30° C. A reaction time, which cannot be uniquely determined, is generally in the range of 1 to 48 hours.

The solvent can be removed from the reaction solution thus produced containing a polymer having one or more units each represented by the chemical formula (18) in its molecule by an ordinary method such as distillation. Alternatively, using a solvent, for example, an alcohol such as methanol or ethanol, or an ether such as dimethyl ether, diethyl ether, or tetrahydrofuran, the polymer having one or more units each represented by the chemical formula (18) in its molecule can be re-precipitated and recovered by uniformly mixing a solvent that does not dissolve that polymer with the solvent. The resultant polymer having one or more units each represented by the chemical formula (18) in its molecule can be subjected to isolation purification as required. A method for the isolation purification is not particularly limited, and includes a method involving reprecipitation using a solvent insoluble in the polymer having one or more units each represented by the chemical formula (18) in its molecule, a method according to column chromatography, or the like.

(Application to Toner)

Applications of the polymer according to the present invention include applications to toner for developing an electrostatic charge image and an image forming process using the toner.

To be specific, the polymer can be used as a charge control agent to be internally or externally added to toner. That is, the present invention relates to a charge control agent containing the polymer described above and a toner for developing an electrostatic charge image containing the charge control agent.

The toner for developing an electrostatic charge image is used for an image forming method or an image forming apparatus described below. The image forming method includes: a charging step of externally applying a voltage to a charging member to evenly charge an electrostatic latent image-bearing member; a developing step of forming a toner image on the electrostatic latent image-bearing member; a transferring step of transferring the toner image on the electrostatic latent image-bearing member onto an image-receiving material via or not via an intermediate transfer member; and a heat-fixing step of fixing the toner image on the image-receiving material under heating.

The image forming apparatus includes means corresponding respectively to the steps of the method, i.e., charging means, developing means, transferring means, and heat-fixing means.

Here, a technology related to toner will be described below.

A large number of electrophotographic methods using toner have been known. A general method involves: utilizing a photoconductive substance to form an electrical latent image on an image-bearing member (photosensitive member) by using various means; developing the latent image with toner to form a visible image; transferring the toner image onto an image-receiving material such as paper as required; and fixing the toner image onto the image-receiving material under heating and/or pressure or the like to provide a copy.

Cascade development, magnetic brush development, impression development, or the like has been known as a method of visualizing an electrical latent image A method involving: using magnetic toner and a rotation developing sleeve having a magnetic pole at its center; and allowing the magnetic toner to be attracted from a place on the developing sleeve to a place on a photosensitive member in a magnetic field has also been used. Development methods used for developing an electrostatic latent image are classified into: a two-component development method involving the use of a two-component developer composed of toner and a carrier; and a one-component development method involving the use of a one-component developer composed only of toner and using no carrier. Here, a colored fine particle generally referred to as toner contains a binder resin and a colorant as essential ingredients, and further contains a charge control agent, magnetic powder, or the like as required. The polymer according to the present invention can be used for such toner.

For example, the polymer compound represented by the chemical formula (19) is used as a charge control agent to be used in the composition of toner for developing an electrostatic charge image, whereby excellent charging properties can be provided and good dispersibility of the compound into a toner resin and good anti-spent property can be provided.

In addition, when the polymer according to the present invention is used, toner for developing an electrostatic charge image can be provided, which prevents image fogging from occurring at the time of output by an image forming apparatus and excellent transferability.

Furthermore, a charge control agent using the polymer according to the present invention can be colorless or weak in tinting power. Therefore, an arbitrary colorant can be selected in accordance with a hue required for color toner. A charge control agent which is colorless or has weak tinting power is preferable because it hardly affects the original hue of a dye or a pigment.

Furthermore, when toner for developing an electrostatic charge image is constituted so as not to contain a heavy metal, toner which is highly safe and is industrially useful can be provided.

(Use as Charge Control Agent)

When the polymer according to the present invention is used as a charge control agent, the polymer preferably has a structure containing a sulfonic group or a derivative of the sulfonic group at its side chain, as in the monomer unit represented by the chemical formula (19).

The presence of a unit having an anionic or electron-withdrawing group exhibits excellent negative chargeability.

The polymer according to the present invention has good compatibility with a binder resin of toner.

Toner containing the polymer of the present invention has a high specific charge amount and good stability over time. Therefore, a vivid image can be stably obtained in electrostatic image formation even-if the toner is stored for a long period of time. In addition, the polymer is colorless or has extremely weak tint, and has good negative chargeability. Therefore, each of black negatively charged toner and color toner can be produced. Furthermore, compatibility can be widely controlled by appropriately selecting the kinds/composition ratios of monomer units constituting the polymer of the present invention.

Here, when a resin composition is selected in such a manner that a charge control agent has a microphase-separated structure in a toner binder, charge can be stably maintained because no electrical continuity of toner occurs.

In addition, the polymer of the present invention contains no heavy metal. Therefore, toner can be stably produced because no polymerization inhibition action due to a heavy metal which may be observed in a metal-containing charge control agent occurs when toner is produced by means of suspension polymerization or emulsion polymerization.

Here, a charge control agent will be described below in further detail.

The charging property of a binder resin itself may be utilized without using a charge control agent for charging toner. In this case, however, the stability of charging over time and humidity resistance become poor, and good image quality is not obtained in some cases.

Therefore, a charge control agent is generally added for maintaining and controlling the charge of toner. Examples of a charge control agent conventionally known in the art today include: charge control agents each having negative frictional chargeability such as azo dye metal complexes, metal complexes of aromatic dicarboxylic acids, and metal complexes of salicylic acid derivatives; and positive charge control agents such as nigrosin-based dyes, triphenylmethane-based dyes, and organic tin compounds including various quaternary ammonium salt dibutyltin oxides.

When the polymer according to the present invention is used for a charge control agent, the polymer may be used in combination with any one of the above conventionally known charge control agents.

It should be noted that, for example, a copolymer of styrene and/or α-methylstyrene and an alkyl(meth)acrylate or alkyl (meth)acrylate amide having a sulfonic group (see JP-A Ser. Nos. 08-179564, JP 08-012467 B, and JP 2807795 B, which are referred to as Patent Documents 1 to 3, respectively) is often used as a conventionally known polymer-based charge control agent.

(Addition to Toner of Polymer According to the Present Invention)

In the present invention, a method involving internal addition to toner or a method involving external addition to toner may be used as a method of incorporating a charge control agent composed of any one of the polymers described above into toner. The addition amount of a charge control agent in the case of internal addition is generally in the range of 0.1 to 50 weight %, or preferably 0.2 to 20 weight % with respect to the total weight of a toner binder and the charge control agent. An addition amount of less than 0.1 wt % is not preferable because the degree of improvement in chargeability of toner may be insufficient. On the other hand, an addition amount in excess of 50 wt % is not preferable from the viewpoint of economy. A weight ratio between a toner binder and a charge control agent in the case of external addition is preferably in the range of 0.01 to 5 wt % with respect to the total weight of the toner binder and the charge control agent. It is particularly preferable to allow the charge control agent to mechanochemically adhere to the toner surface. The polymer of the present invention may also be used in combination with a conventionally known charge control agent. The amount of a charge control agent other than the polymer of the present invention is not limited as long as the addition of the charge control agent has an effect and an effect of the use of the polymer of the present invention is not impaired.

The polymer of the present invention used as a charge control agent has a number average molecular weight of generally 1,000 to 1,000,000, or preferably 1,000 to 300,000. A number average molecular weight of less than 1,000 provides an insufficient charge amount and adversely affects the fluidity of toner because the polymer is completely Compatible with a toner binder and a discontinuous domain is hardly formed. In addition, a number average molecular weight in excess of 1,000,000 makes it difficult to disperse the polymer into toner.

The molecular weight of the polymer of the present invention was measured by means of gel permeation chromatography (GPC). A specific measurement method by GPC involves: dissolving the above polymer into a 0.1 wt % LiBr-containing dimethylformamide (DMF), chloroform, or the like in advance; measuring many samples in the same mobile phase; and determining a molecular weight distribution from a calibration curve of a standard polystyrene resin.

In addition, in the present invention, out of the above polymers, a polymer having a ratio (Mw/Mn) of a weight average molecular weight (Mw) and a number average molecular weight (Mn) measured as described above in the range of 1 to 10 is preferably used as a charge control agent.

It is preferable that a polymer to be used as a charge control agent in the present invention has a melting point in the range of 20 to 150° C., or particularly 40 to 150° C., or has no melting point, but has a glass transition point in the range of 10 to 150° C., or particularly 20 to 150° C. When the polymer has a melting point lower than 20° C., or has no melting point and has a glass transition point lower than 10° C., the fluidity and storage stability of the toner are apt to be adversely affected. On the other hand, when the polymer has a melting point higher than 150° C., or has no melting point and has a glass transition point higher than 150° C., it becomes difficult to knead the charge control agent in the toner, and a charge amount distribution is apt to be over a wide range. In this case, the melting point Tm and the glass transition point Tg may be measured by using a differential scanning calorimeter of a high-precision inner heat input compensation type such as DSC-7 manufactured by PerkinElmer.

The composition of the toner for developing an electrostatic charge image of the present invention is generally 0.1 to 50 wt % of a charge control agent, 20 to 95 wt % of a toner binder, and 0 to 15 wt % of a coloring material based on the toner weight. The toner may contain 60 wt % or less of magnetic powder (for example, powder of a ferromagnetic metal such as iron cobalt, or nickel, or a compound such as magnetite, hematite, or ferrite) serving also as a coloring material as required. The toner may further contain various additives (such as a lubricant (for example, polytetrafluoroethylene, low-molecular-weight polyolefin, an aliphatic acid, or a metal salt or amide thereof) and other charge control agents (for example, a metal-containing azo dye and a salicylic acid metal salt)). Hydrophobic colloidal silica fine powder or the like may also be used for improving the fluidity of the toner. A total amount of those additives is generally 10 wt % or less based on the toner weight.

In the toner of the present invention, in one toner particle, at least part of a toner binder preferably forms a continuous phase and at least part of a charge control agent preferably forms a discontinuous domain. As compared to the case where a charge control agent is completely compatible with a toner binder without the formation of a discontinuous domain, the added charge control agent is easily exposed to the toner surface, and a small addition amount can exert an effect. The domain has a dispersed particle size in the range of preferably 0.01 to 4 μm, or more preferably 0.05 to 2 μm. A dispersed particle size in excess of 4 μm provides insufficient dispersibility, and so, a problem is raised such that a charge amount distribution becomes wide and transparency of toner deteriorates. In addition, a dispersed particle size of less than 0.01 μm requires a large addition amount of a charge control agent as in the case where a charge control agent is completely compatible with a toner binder without the formation of a discontinuous domain. The fact that at least part of the charge control agent forms a discontinuous domain and the dispersed particle size of the domain can be confirmed by observing a section of toner by means of a transmission electron microscope or the like. For clearly observing an interface, a toner section may be observed by means of an electron microscope after the section has been stained with ruthenium tetroxide, osmium tetroxide, or the like.

For the purpose of reducing the particle size of a discontinuous domain formed by the polymer of the present invention, a polymer that is compatible with the polymer of the present invention and is also compatible with a toner binder may also be incorporated as a compatibilizer. An example of the compatibilizer includes a polymer in which a polymer chain containing 50 mol % or more of a monomer having substantially the same structure as that of a constituent monomer of the polymer of the present invention and a polymer chain containing 50 mol % or more of a monomer having substantially the same structure as that of a constituent monomer of the toner binder are bound in graft manner or block manner. The usage amount of the compatibilizer is generally 30 wt % or less, or preferably 1 to 10 weight % with respect to the polymer of the present invention.

(Other Components)

Hereinafter, other components constituting the toner for developing an electrostatic charge image of the present invention will be described below.

The toner for developing an electrostatic charge image according to the present invention may contain a binder resin, a colorant, and other additives to be added as required as well as the above charge control agent.

(Binder Resin)

First, a general thermoplastic resin can be used as the binder resin. Examples of an available thermoplastic resin include polystyrene, polyacrylate, a styrene-acrylate copolymer, polyvinyl chloride, polyvinyl acetate, polyvinylidene chloride, a phenol resin, an epoxy resin, and a polyester resin. Any one of the resins that are generally used for producing toner can be used, and the resin to be used is not particularly limited.

In addition, the charge control agent of the present invention can be mixed with a binder resin before being turned into toner, and the mixture can be used as a toner binder composition of the present invention having a charge controlling ability. Examples of the binder resin include a styrene-based polymer, a polyester-based polymer, an epoxy-based polymer, a polyolefin-based polymer, and a polyurethane-based polymer. Each of these may be used alone or in combination.

Examples of the styrene-based polymer include: a copolymer of styrene and (meth)acrylate and copolymers of other monomers copolymerizable with them; and a copolymer of styrene and a diene-based monomer (such as butadiene or isoprene) and copolymers of other monomers copolymerizable with them. An example of the polyester-based polymer includes a polycondensate of an aromatic dicarboxylic acid and an alkylene oxide adduct of an aromatic diol. Examples of the epoxy-based polymer include a product of a reaction between an aromatic diol and epichlorohydrin and a denatured product thereof. Examples of the polyolefin-based polymer include copolymer chains of polyethylene, polypropylene, and other monomers copolymerizable with them. An example of the polyurethane-based polymer includes a compound obtained by polyaddition of an aromatic diisocyanate and an alkylene oxide adduct of an aromatic diol.

Specific examples of the binder resin used in combination with the charge control agent of the present invention include: a polymer of any one of the polymerizable monomers described below; and a copolymerization product obtained by using a mixture of the polymerizable monomers or two or more kinds of the polymerizable monomers. Specific examples of such a binder resin include: a styrene-based polymer such as a styrene-acrylic acid copolymer or a styrene-methacrylic acid-based copolymer; a polyester-based polymer; an epoxy-based polymer; a polyolefin-based polymer; and a polyurethane-based polymer, which may be preferably used.

Examples of a polymerizable monomer include: styrene and derivatives thereof such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, and p-n-dodecylstyrene; ethylene unsaturated monoolefins such as ethylene, propylene, butylene, and isobutylene; unsaturated polyenes such as butadiene; halogenated vinyls such as vinyl chloride, vinylidene chloride, vinyl bromide, and vinyl fluoride; vinyl esters such as vinyl acetate, vinyl propionate, and vinyl benzoate; α-methylene aliphatic monocarboxylates such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, and diethylaminoethyl methacrylate; acrylates such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, and phenyl acrylate; vinyl ethers such as vinyl methyl ether, vinyl ethyl ether, and vinyl isobutyl ether; vinyl ketones such as vinyl methyl ketone, vinyl hexyl ketone, and methyl isopropenyl ketone; N-vinyl compounds such as N-vinylpyrrole, N-vinylcarbazole, N-vinylindole, and N-vinylpyrrolidone; vinyl naphthalenes; acrylic/methacrylic acid derivatives such as acrylonitrile, methacrylonitrile, and acrylamide; diesters of esters and dibasic acids of the above α,β-unsaturated acids; dicarboxylic acids such as maleic acid, methyl maleate, butyl maleate, dimethyl maleate, phthalic acid, succinic acid, and terephthalic acid; polyol compounds such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A, and polyoxyethylenated bisphenol A; isocyanates such as p-phenylene diisocyanate, p-xylylene diioscyante, and 1,4-tetramethylene diisocynate; amines such as ethyl amine, butyl amine, ethylenediamine, 1,4-diaminobenzene, 1,4-diaminobutane, and monoethanol amine; and epoxy compounds such as diglycidyl ether, ethylene glycol diglycidyl ether, bisphenol A glycidyl ether, and hydroquinone diglycidyl ether.

(Cross-Linking Agent)

In producing a binder resin to be used in combination with the charge control agent of the present invention, any one of such cross-linking agents as described below may be used as required. Examples of a bifunctional cross-linking agent include divinylbenzene, bis(4-acryloxypolyethoxyphenyl) propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, diacrylates of polyethylene glycols #200, #400, and #600, dipropylene glycol diacrylate, polypropylene glycol diacrylate, polyester-type diacrylate (MANDA Nippon Kayaku Co., Ltd), and compounds obtained by changing the "acrylate" in each of the above compounds to the "methacrylate".

Examples of a polyfunctional cross-linking agent that is bifunctional or more include: pentaerythritol triacrylate, trimethylol ethane triacrylate, trimethylol propane triacrylate, tetramethylol methane tetraacrylate, and oligoester acrylate, and methacrylates thereof; 2,2-bis(4-methacryloxy, polyethoxyphenyl)propane; diallyl phthalate; triallyl cyanurate; triallyl isocyanurate; triallyl isocyanurate; and diaryl chlorendate.

(Polymerization Initiator)

In addition, in producing a binder resin to be used in combination with the charge control agent of the present invention, any one of such polymerization initiators as described below may be used as required. Examples of the polymerization initiator include t-butylperoxy-2-ethylhexanoate, cumine perpivarate, t-butylperoxylaurate, benzoyl peroxide, lauroyl peroxide, octanoyl peroxide, di-t-butyl peroxide, t-butylcumyl peroxide, dicumyl peroxide, 2,2'-azobisisobutyronitrile, 2,2'-azobis(2-methylbutyronitrile), 2,2'-azobis(2, 4-dimethylvaleronitrile), 2,2'-azobis(4-methoxy-2,4-dimethylvaleronitrile), 1,1-bis(t-butylperoxy)3,3,5-trimethylcyclohexane, 1,1-bis(t-butylperoxy)cyclohexane, 1,4-bis(t-butylperoxycarbonyl)cyclohexane, 2,2-bis(t-butylperoxy)-octane, n-butyl 4,4-bis(t-butylperoxy)valerate, 2,2-bis(t-butylperoxy)butane, 1,3-bis(t-butylperoxy-isopropyl)benzene, 2,5-dimethyl-2,5-di(t-butylperoxy)hexane, 2,5-dimethyl-2,5-di(t-butylperoxy)hexane, 2,5-dimethyl-2,5-di (benzoylperoxy)hexane, di-t-butyldiperoxyisophthalate, 2,2-bis(4,4-di-t-butylperoxycyclohexyl)propane, di-t-butylperoxy α-methylsuccinate, di-t-butylperoxydimethylglutarate, di-t-butylperoxyhexahydroterephthalate, di-t-butylperoxyazelate, 2,5-dimethyl-2,5-di(t-butylperoxy) hexane, diethylene glycol-bis(t-butylperoxycarbonate), di-t-butylperoxytrimethyladipate, tris(t-butylperoxy)triazine, and vinyl tris(t-butylperoxy)silane. Each of them may be used alone or in combination. The polymerization initiator is used at a concentration of generally 0.05 part by weight or more (preferably 0.1 to 15 parts by weight) with respect to 100 parts by weight of the monomer. The ratio of the charge control agent of the present invention to be internally added to a binder resin is generally 0.1 to 50 wt %, or preferably 0.2 to 20 wt %. When the weight ratio of the charge control agent to be internally added is less than 0.1 wt %, a charge amount is low. When the weight ratio exceeds 50 weight %, charging stability of toner deteriorates.

(Charge Control Agent: Other than Polymer of the Present Invention)

A conventionally used charge control agent other than the charge control agent of the present invention may be used in combination with the charge control agent of the present invention. Specific examples thereof include a nigrosin-based dye, a quaternary ammonium salt, and a monoazo-based metal complex salt dye. The addition amount of the charge control agent, which can be determined in consideration of conditions such as chargeability of a binder resin, a production method including the addition amount and a dispersion method of a colorant, and chargeability of the other additives, is 0.1 to 20 parts by weight, or preferably 0.5 to 10 parts by weight with respect to 100 parts by weight of the binder resin. In addition to the above, an inorganic particle of a metal oxide or the like, or an inorganic substance the surface of which is treated with any one of the above organic substances may be used. Any one of those charge control agents may be used while being mixed with, and added to, a binder resin, or may be used while being allowed to adhere to a toner particle surface.

<Colorant>

Any one of the colorants that are generally used for producing toner can be used as a colorant included in the toner for developing an electrostatic charge image of the present invention without particular limitation. Examples of an available colorant include pigments and/or dyes such as carbon black, titanium white, a monoazo-based red pigment, a disazo-based yellow pigment, a quinacridone-based magenta pigment, and an anthraquinone dye.

More specifically, when the toner for developing an electrostatic charge image of the present invention is used as magnetic color toner, examples of a colorant to be used include C.I. Direct Red 1, C.I. Direct Red 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4, and C.I. Basic Green 6. Examples of a pigment to be used include chrome yellow, cadmium yellow, mineral fast yellow, navel yellow, naphthol yellow S, Hansa yellow G, permanent yellow NCG, tartrazine lake, chrome orange, molybdenum orange, permanent orange GTR, pyrazolone orange, benzidine orange G, cadmium red, permanent red 4R, watching red calcium salt, eosin lake, brilliant carmine 3B, manganese violet, fast violet B, methyl violet lake, prussian blue, cobalt blue, alkali blue lake, Victoria blue lake, phthalocyanine blue, fast sky blue, indanthrene blue BC, chrome green, chromium oxide, pigment green B, malachite green lake, and final yellow green G.

In addition, when the toner for developing an electrostatic charge image of the present invention is used as two-component full-color toner, any one of such colorants as described below may be used. Examples of a coloring pigment for magenta toner include: C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, and 209; C.I. Pigment-Violet 19; and C.I. Vat Red 1, 2, 10, 13, 15, 23, 29, and 35.

In the present invention, each of the above pigments may be used alone, but it is preferable to use a dye and a pigment in combination to improve definition in terms of image quality of a full-color image. Examples of a magenta dye to be used in that case include: oil-soluble dyes such as C.I. Solvent Red 1, 3, 8, 23, 24, 25, 27, 30, 49, 81, 82, 83, 84, 100, 109, and 121, C.I. Disperse Red 9, C.I. Solvent Violet 8, 13, 14, 21, and 27, and C.I. Disperse Violet 1; and basic dyes such as C.I. Basic Red 1, 2, 9, 12, 13, 14, 15, 17, 18, 22, 23, 24, 27, 29, 32, 34, 35, 36, 37, 38, 39, and 40, and C.I. Basic Violet 1, 3, 7, 10, 14, 15, 21, 25, 26, 27, and 28.

Examples of other coloring pigments include: cyan coloring pigments such as C.I. Pigment Blue 2, 3, 15, 16, and 17, C.I. Vat Blue 6, C.I. Acid Blue 45, and copper phthalocyanine pigments each having a phthalocyanine skeleton substituted by 1 to 5 phthalimide methyl groups; and yellow coloring pigments such as C.I. Pigment Yellow 1, 2, 3, 4, 5, 6, 7, 10, 11, 12, 13, 14, 15, 16, 17, 23, 65, 73, and 83, and C.I. Vat Yellow 1, 3, and 20.

Each of the dyes and pigments described above may be used alone, or two or more of them may be arbitrarily mixed for obtaining a desired toner hue.

In consideration of environmental protection and safety for a human body, food pigments such as various food lakes can be suitably used. Examples thereof include Food Red No. 40 Aluminum Lake, Food Red No. 2 Aluminum Lake, Food Red No. 3 Aluminum Lake, Food Red No. 106 Aluminum Lake, Food Yellow No. 5 Aluminum Lake, Food Yellow No. 4 Aluminum Lake, Food Blue No. 1 Aluminum Lake, and Food Blue No. 2 Aluminum Lake. Any one of the above water-insoluble food pigments can also function as a charge control agent. In that case, any one of the aluminum lakes can be used for negative charging. A water-insoluble food pigment capable of functioning as a charge control agent described above not only improves the environmental safety of toner but also contributes to a reduction in cost of toner.

The content of any one of such colorants as described above in toner may be widely changed in accordance with a desired coloring effect and the like. For obtaining the best toner properties, that is, in consideration of coloring power for forming a printed letter, form stability of toner, scattering of toner, and the like, any one of those colorants is used in an amount of generally about 0.1 to 60 parts by weight, or preferably about 0.5 to 20 parts by weight with respect to 100 parts by weight of a binder resin.

(Other Components of Toner)

The toner for developing an electrostatic charge image of the present invention may contain any one of the following compounds as well as the binder resin and colorant components described above to such an extent that an effect of the present invention is not adversely affected. Examples of the compounds include: a silicone resin; polyester; polyurethane; polyamide; an epoxy resin; polyvinyl butyral; rosin; denatured rosin; a terpene resin; a phenol resin; an aliphatic or alicyclic hydrocarbon resin such as low-molecular-weight polyethylene or low-molecular-weight polypropylene; an aromatic petroleum resin; chlorinated paraffin; and a paraffin wax. Of those, examples of a wax preferably used include low-molecular-weight polypropylene and a by-product thereof, low-molecular-weight polyester and an ester-based wax, and an aliphatic derivative. Waxes obtained by fractionating those waxes according to molecular weights are also preferably used in the present invention. Oxidation, block copolymerization, or graft modification may also be performed after the fractionation.

In particular, the toner for developing an electrostatic charge image of the present invention comes to have excellent properties when the toner contains such wax components as described above and these wax components are dispersed into the binder resin in a substantially spherical and/or spindle island fashion in the case where a toner section is observed by means of a transmission electron microscope (TEM).

(Method of Producing Toner)

Any one of the conventionally known methods can be used for specifically producing the toner for developing an electrostatic charge image of the present invention having such a structure as described above. The toner for developing an electrostatic charge image of the present invention can be produced by means of, for example, the so-called pulverization method for obtaining toner by using the following steps. That is, to be specific, the toner for developing an electrostatic charge image of the present invention having a desired particle size can be obtained by: sufficiently mixing resins such as a binder resin, and a charge control agent and a wax to be added as required by the use of a mixer such as a Henschel mixer or a ball mill; melting and kneading the mixture by using a heat kneader such as a heat roll, a kneader, or an extruder to make the resins compatible with each other; dispersing or dissolving into the kneaded product a pigment or a dye as a colorant, or a magnetic substance, and an additive such as a metal compound to be added as required; cooling the resultant for solidification; pulverizing the solidified product by means of a pulverizer such as a jet mill or a ball mill; and classifying the pulverized product. A multi-division classifier is preferably used in the classification step in terms of production efficiency.

The toner for developing an electrostatic charge image of the present invention having a desired particle size can also be obtained by: dissolving a binder resin and a charge control agent and the like into a solvent (for example, an aromatic hydrocarbon such as toluene or xylene, a halogenated compound such as chloroform or ethylene dichloride, a ketone such as acetone or methyl ethyl ketone, or an amide such as dimethylformamide); mixing the solution; subjecting the solution to stirring treatment; placing the resultant in water for reprecipitation; filtering and drying the precipitate; pulverizing the solidified product by means of a pulverizer such as a jet mill or a ball mill; and classifying the pulverized product. A multi-division classifier is preferably used in the classification step in terms of production efficiency.

The toner for developing an electrostatic charge image of the present invention can also be produced by means of the so-called polymerization method described below. That is, in this case, the toner for developing an electrostatic charge image of the present invention can be obtained by: mixing and dispersing a polymerizable monomer of a binder resin, a charge control agent, a pigment or a dye as a colorant, or a magnetic substance, and, as required, materials such as a cross-linking agent, a polymerization initiator, a wax, another binder resin, and other additives; subjecting the resultant to suspension polymerization in an aqueous dispersion medium in the presence of a surfactant or the like to synthesize polymerizable colored resin particles; subjecting the resultant particles to solid-liquid separation; drying the resultant; and classifying the resultant as required. Furthermore, a colored fine particle containing no charge control agent may be prepared according to the above method, and the above polymer may be fixed and added to particle surface by means of a mechanochemical method or the like alone or together with an external additive such as colloidal silica.

(Silica External Additive)

In the present invention, silica fine powder is preferably externally added to toner produced by means of such methods as described above to improve charging stability, developability, fluidity, and durability, where one having a specific surface area of 20 $m^2/g$ or more (particularly 30 to 400 $m^2/g$) measured by nitrogen adsorption measured according to a BET method may be used to provide good results. The amount of the silica fine powder to be used in this case is about 0.01 to 8 parts by weight, or preferably about 0.1 to 5 parts by weight with respect to 100 parts by weight of toner particles. The silica fine powder to be used at this time is preferably treated with any one of treating agents such as silicone varnish, various modified silicone varnishes, silicone oil, various modified silicone oils, silane coupling agents, silane coupling agents each having a functional group, and other organic silicon compounds. Those treating agents may be mixed before use.

(Inorganic Powder)

Any one of the inorganic powders described below is also preferably added for improving the developability and durability of the toner. Examples of the inorganic fine powders include: oxides of metals such as magnesium, zinc, aluminum, cerium, cobalt, iron, zirconium, chromium, manganese, strontium, tin, and antimony; composite metal oxides such as calcium titanate, magnesium titanate, and strontium titanate; metal salts such as calcium carbonate, magnesium carbonate, and aluminum carbonate; clay minerals such as kaolin; phosphoric acid compounds such as apatite; silicon compounds such as silicon carbide and silicon nitride; and carbon powders such as carbon black and graphite. Of those, fine powder of zinc oxide, aluminum oxide, cobalt oxide, manganese dioxide, strontium titanate, or magnesium titanate is preferably used.

(Lubricant)

Any one of the lubricant powders described below may be further added to the toner. Examples of the lubricant powders include: fluorine resins such as Teflon and polyvinylidene fluoride; fluorine compounds such as carbon fluoride; aliphatic metal salts such as zinc stearate; aliphatic acid derivatives such as an aliphatic acid and an aliphatic ester; and molybdenum sulfide.

(With Regard to Carrier)

The toner for developing an electrostatic charge image of the present invention can be singly used as a nonmagnetic one-component developer, or can be applied to any one of the conventionally known various toners such as a nonmagnetic toner constituting a magnetic two-component developer together with a magnetic carrier and a magnetic toner to be singly used as a magnetic one-component toner. Any one of conventionally known carriers can be used as a carrier to be used for a two-component development method. To be specific, particles having an average particle size of 20 to 300 μm and formed of metals such as surface-oxidized or unoxidized iron, nickel, cobalt, manganese, chromium, and a rare earth, and alloys or oxides of them can be used as carrier particles. In the carrier to be used in the present invention, the surfaces of the carrier particles are preferably attached or coated with substances such as a styrene-based resin, an acrylic resin, a silicone-based resin, a fluorine-based resin, and a polyester resin.

(Magnetic Toner)

The toner for developing an electrostatic charge image of the present invention may contain a magnetic material in its toner particles to serve as magnetic toner. In this case, the magnetic material can also function as a colorant. Examples of the magnetic material to be used at this time include: iron oxides such as magnetite, hematite, and ferrite; and metals such as iron, cobalt, and nickel, and alloys and mixtures of these metals with metals such as aluminum, cobalt, copper, lead, magnesium, tin, zinc, antimony, beryllium, bismuth, cadmium, calcium, manganese, selenium, titanium, tungsten, and vanadium. The magnetic material that can be used in the present invention has an average particle size of preferably 2 μm or less, and more preferably about 0.1 to 0.5 μm. The amount of the magnetic material in the toner is preferably 20 to 200 parts by weight, or particularly preferably 40 to 150 parts by weight with respect to 100 parts by weight of the binder resin.

It is necessary to make it possible to faithfully develop finer latent image dots for achieving further improved image quality. To this end, the weight average particle size of the toner particles for developing an electrostatic charge image of the present invention is preferably adjusted to fall within the range of 4 μm to 9 μm. That is, toner particles having a weight average particle size of less than 4 μm are not preferable because transfer efficiency reduces and the amount of transfer residual toner remaining on a photosensitive member is apt to increase, which tends to result in image unevenness based on fogging and insufficient transfer. Toner particles having a weight average particle size in excess of 9 μm are apt to cause scattering around a letter or a line image.

In the present invention, the average particle size and particle size distribution of the toner were measured by using a Coulter Counter TA-II or a Coulter Multisizer (manufactured by Beckman Coulter) connected with an interface (manufactured by Nikkaki-Bios) and a personal computer for outputting a number distribution and a volume distribution. An 1% NaCl aqueous solution is prepared as an electrolyte to be used in the measurement by using first class sodium chloride. For example, a commercially available ISOTON R-II (manufactured by Coulter Scientific Japan Ltd.) may also be used as an electrolyte. A specific measurement method is as follows. 100 to 150 ml of the electrolyte is added with 0.1 to 5 ml of a surfactant (preferably an alkylbenzene sulfonate) as a dispersant. Furthermore, 2 to 20 mg of a sample to be measured is added to prepare a sample for measurement. At the time of measurement, the electrolyte into which the sample to be measured was suspended was subjected to dispersion treatment for about 1 to 3 minutes by using an ultrasonic dispersing unit, and the volume and number of toner having a particle size of 2 μm or more were measured by means of Coulter counter TA-II using a 100 μm aperture to calculate a volume distribution and a number distribution. Subsequently, a volume-based weight average particle size (D4) and a number-based length average particle size (D1) were determined from the volume distribution and the number distribution according to the present invention, respectively.

(Charge Amount)

The toner for developing an electrostatic charge image of the present invention has a charge amount per unit weight (two-component method) of preferably −10 to −80 μC/g, and more preferably −15 to −70 μC/g, for improving transfer efficiency in a transfer method involving the use of a transfer member to which a voltage is applied.

A method of measuring a charge amount (two-component triboelectrification) according to a two-component method used in the present invention will be described below. A charge amount measuring device shown in FIG. 7 was used for the measurement. First, in a constant environment, an EFV 200/300 (manufactured by Powder Tech) is used as a carrier, and a mixture obtained by adding 0.5 g of toner to be measured to 9.5 g of the carrier is placed in a polyethylene bottle having a volume of 50 to 100 ml. The bottle is set in a shaker with a constant amplitude, and is shaken for a predetermined period of time under shaking conditions of: an amplitude of 100 mm; and a shaking speed of 100 reciprocations/min.

Figure 7:
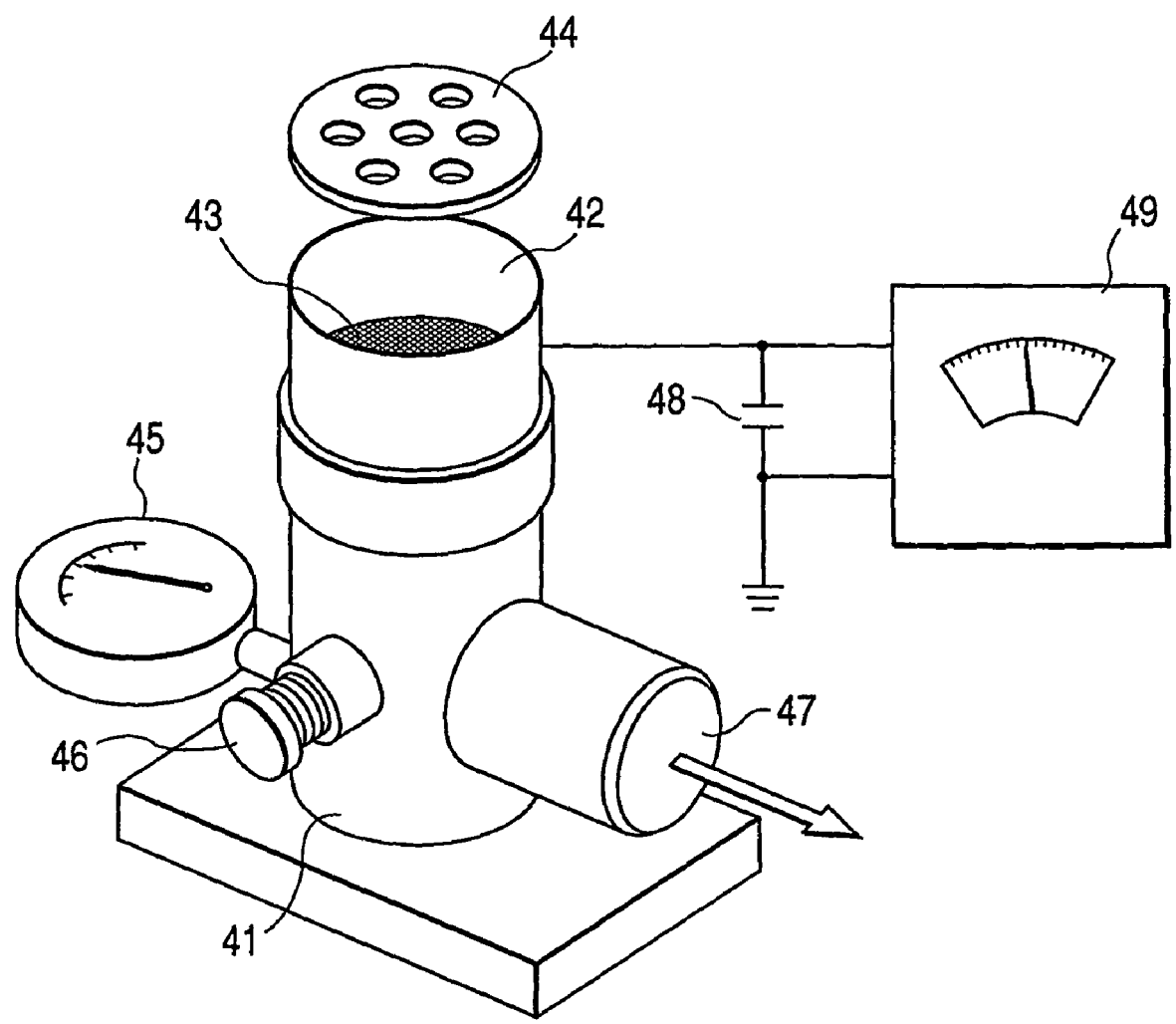
FIG. 7 is a schematic view showing a blow-off charge amount measuring device for measuring a charge amount of toner.

Next, 1.0 to 1.2 g of the mixture are placed in a metallic measurement container 42, which has a 500-mesh screen 43 at its bottom, of a charge amount measuring device 41 shown in FIG. 7, and the container is capped with a metallic cap 44. The weight of the entire measurement container 42 is measured and designated as W1 (g). Next, the toner in the container is sucked through a suction port 47 by means of a sucker (not shown) (at least part of the sucker in contact with the measurement container 42 is made of an insulator), and an air quantity regulating valve 46 is adjusted in such a manner that a vacuum gage 45 indicates a pressure of 2,450 Pa (250 mmAq). Suction is performed for 1 min in this state to suck and remove the toner. The potential of a potentiometer 49 is designated as V (volt). Here, reference numeral 48 denotes a capacitor having a capacity of C (μF). In addition, the weight of the entire measuring device after the suction is measured and designated as W2 (g). The frictional charge amount of the toner is calculated from those measured values according to the following equation.

Frictional charge amount(μC/g)=$C \times V/(W1-W2)$ (Method of Measuring Molecular Weight and Molecular Weight Distribution of Binder Resin)

In addition, a binder resin to be used as a constituent of the toner for developing an electrostatic charge image of the present invention preferably has a peak in a low-molecular-weight region in the range of 3,000 to 15,0000 in molecular weight distribution by means of GPC particularly when produced by means of the pulverization method. That is, when a GPC peak in a low-molecular-weight region exceeds 15,000, an improvement in transfer efficiency may be insufficient. It is not preferable to use a binder resin having a GPC peak in a low-molecular-weight region of less than 3,000 because fusion is apt to occur at the time of surface treatment.

In the present invention, the molecular weight of the binder resin was measured by gel permeation chromatography (GPC). A specific measurement method according to GPC involved: using a sample for measurement obtained by extracting toner with a tetrahydrofuran (THF) solvent for 20 hours by using a Soxhlet extractor; connecting A-801, 802, 803, 804, 805, 806, and 807 manufactured by Showa Denko K. K to constitute a column; and measuring a molecular weight distribution using a calibration curve drawn by using standard polystyrene resin. In addition, in the present invention, a binder resin having a ratio (Mw/Mn) of a weight average molecular weight (Mw) and a number average molecular weight (Mn) measured as described above in the range of 2 to 100 is preferably used.

<Glass Transition Point of Toner>

Furthermore, the toner of the present invention is prepared by using an appropriate material to have, a glass transition point in the range of preferably 40° C. to 75° C., or more preferably 52° C. to 70° C. from the viewpoints of fixability and storage stability In this case, the glass transition point Tg may be measured by using a differential scanning calorimeter of a high-precision inner heat input compensation type such as a DSC-7 manufactured by PerkinElmer. A measurement method is performed in accordance with ASTM D 3418-82. In the present invention, it is recommended that in measuring the glass transition point Tg, a DSC curve be used, which is measured by: increasing the temperature of a sample to be measured once to erase entire hysteresis; quenching the sample; and increasing the temperature again at a rate of temperature rise of 10° C./min in the temperature range of 0 to 200° C.

(Image Forming Method and Apparatus)

The toner for developing an electrostatic charge image of the present invention having such a structure as described above is particularly preferably applied to an image forming method and apparatus respectively including the steps of, and means for, externally applying a voltage to a charging member to charge an electrostatic latent image-bearing member; forming an electrostatic charge image on the charged electrostatic latent image-bearing member; developing the electrostatic charge image with toner to form a toner image on the electrostatic latent image-bearing member; transferring the toner image on the electrostatic latent image-bearing member onto a recording material; and fixing the toner image on the recording material under heating, or to an image forming method in which the transferring step is comprised of: a first transferring step of transferring the toner image on the electrostatic latent image-bearing member onto an intermediate transfer member; and a second transferring step of transferring the toner image on the intermediate transfer member onto the recording material, and an image forming apparatus in which the means for carrying out the transferring step is comprised of a means for carrying out the first transferring step and a means for carrying out the second transferring step.

In the present invention, the reaction solvent, temperature and time in the chemical reaction, the purification-method, the charge control agent, and so forth are not limited to those described above.

The inventors of the present invention have found that the polymer described above has very excellent properties as a charge control agent. This will be shown in Examples described later.

It should be noted that the polymer according to the present invention has high safety for a human body and an environment.

EXAMPLES

Hereinafter, the present invention will be described in more detail by way of examples.

First, the polymer, the method of producing the polymer, and the compound provided by the present invention will be described by way of Examples A-1 to R-2. Next, usefulness of the polymer or the like according to the present invention will be described by way of Examples 1 to 40 while using comparative examples.

The polymer and compound, and the methods of producing them according to the present invention are not limited to the following examples.

In each of the following experiments, the structure of the resultant polymer was determined through analysis according to $^1$H-NMR (FT-NMR: Bruker DPX 400; resonance frequency: 400 MHz; measured nuclear species: $^1$H; solvent used: DMSO-$d_6$; measurement temperature: room temperature), Fourier transformation-infrared absorption (FT-IR) spectrum (Nicolet AVATAR 360FT-IR).

The average molecular weight of the resultant polymer was evaluated by means of gel permeation chromatography (GPC; Tosoh Corporation, column; Polymer Laboratories PLgel 5μ MIXED-C, solvent; DMF/LiBr 0.1% (w/v), in terms of polystyrene).

An electric potential titration device AT510 (manufactured by Kyoto Electronics Manufacturing) was used for acid value titration.

Example A-1

With reference to Makromol. Chem, 186, 1711-1720 (1985), a copolymer containing a unit represented by the following formula (A-0) at a content ratio (mol %) of (M):(F)=90:10 was obtained by copolymerizaiton of methacrylic acid with styrene and used for the following experiment.

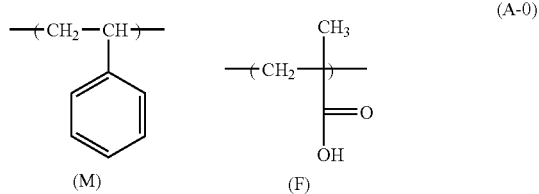

(A-0)

(M)　　　(F)

Under a nitrogen atmosphere, 1.4998 g of the polymer and 1.3710 g of p-toluidine-2-sulfonic acid were placed in a 200-ml three-necked flask. 56.5 ml of pyridine were added to the flask, and the mixture was stirred. Thereafter, 3.84 ml of triphenyl phosphite were added, and heated at 120° C. for 6 hours. After completion of the reaction, the resulting product was re-precipitated in 565 ml of ethanol, and recovered. The resultant polymer was washed with 1-N hydrochloric acid for 1 day, and then, was stirred in water for 1 day to wash the polymer, followed by drying under reduced pressure.

As a result of IR measurement, a peak at 1,695 cm$^{-1}$ derived from a carboxylic acid was reduced, and a peak derived from an amide group was newly observed at 1,658 cm$^{-1}$.

$^1$H-NMR confirmed that the resultant polymer was a copolymer containing 10 mol % of a unit represented by the following formula (A-1) because a peak derived from a methyl group of p-toluidine-2-sulfonic acid shifted.

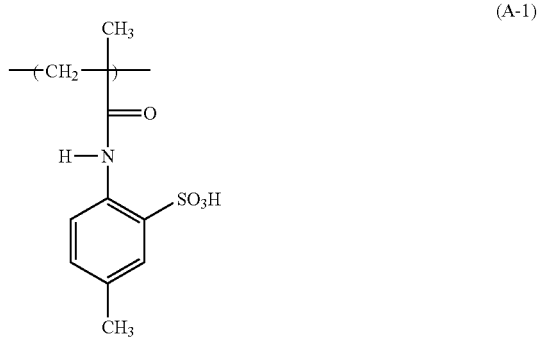

(A-1)

The resultant polymer had a number average molecular weight $M_n$ of 22,000 and a weight average molecular weight $M_w$ of 56,000.

The preparation method was expanded to produce 50 g of the compound. The compound was designated as Exemplified Compound A-1 and used for toner preparation and evaluation.

Example A-2

0.9980 g of the polymer obtained in Example A-1 was placed in a 300-ml round-bottomed flask. Then, 70 ml of chloroform and 17.5 ml of methanol were added to dissolve the polymer, and the solution was cooled to 0° C. 4.89 ml of a 2-mol/L trimethylsilyldiazomethane-hexane solution (manufactured by Aldrich) were added to the solution, and stirred for 4 hours. After the completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9772 g of polymer. $^1$H-NMR confirmed that the resultant polymer was a copolymer containing 10 mol % of a unit represented by the following formula (A-2) because a peak derived from methyl sulfonate was observed at 3 to 4 ppm.

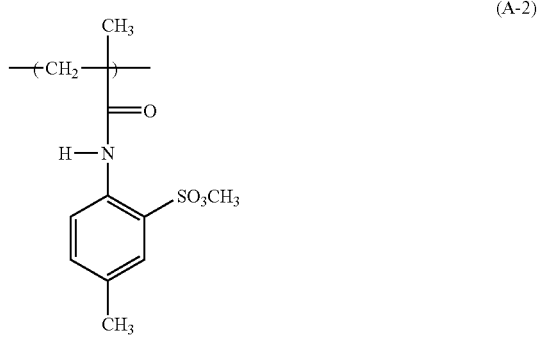

(A-2)

In addition, acid value titration revealed that the sulfonic acid was transformed into methyl sulfonate because no equivalent point derived from the sulfonic acid was observed.

The resultant polymer had a number average molecular weight $M_n$ of 22,000 and a weight average molecular weight $M_w$ of 54,000.

The preparation method was expanded to produce 50 g of the compound. The compound was designated as Exemplified Compound A-2 and used for toner preparation and evaluation.

Example B-1

Poly(methyl methacrylate-co-methacrylic acid) manufactured by ALDRICH was used as a raw material polymer. The polymer was dissolved in chloroform, re-precipitated in methanol 3 times, and was used for reaction. Under a nitrogen atmosphere, 1.5024 g of the polymer and 3.3612 g of 2-aminobenzenesulfonic acid were placed in a 200-ml three-necked flask. 56.5 ml of pyridine was added to the flask, and the mixture was stirred. Thereafter, 10.17 ml of triphenyl phosphite were added, and the whole was heated at 120° C. for 6 hours. After completion of the reaction, the resultant was re-precipitated in 565 ml of ethanol, followed by recovery. The resultant polymer was washed with 1-N hydrochloric acid for 1 day, and then was stirred in water for 1 day to wash the polymer, followed by drying under reduced pressure.

As a result of IR measurement, a peak at 1,695 cm$^{-1}$ derived from a carboxylic acid was reduced, and a peak derived from an amide group was newly observed at 1,658 cm$^{-1}$.

$^1$H-NMR confirmed that the resultant polymer was a copolymer containing 25 mol % of a unit represented by the following formula (B-1) because a peak derived from an aromatic ring of the 2-aminobenzenesulfonic acid structure shifted.

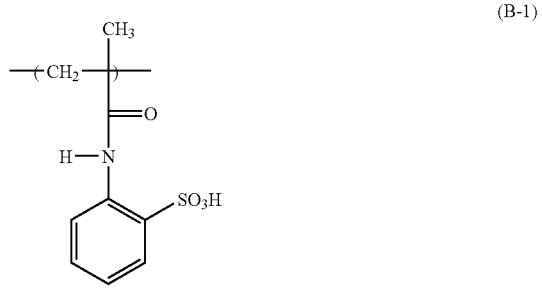
(B-1)

The resultant polymer had a number average molecular weight $M_n$ of 14,000 and a weight average molecular weight $M_w$ of 33,000.

The preparation method was expanded to produce 50 g of the compound. The compound was designated as Exemplified Compound B-1 and used for toner preparation and evaluation.

Example B-2

1.0020 g of the polymer obtained in Example B-1 was placed in a 300-ml round-bottomed flask. Then, 70 ml of chloroform and 17.5 ml of methanol were added to dissolve the polymer, and the solution was cooled to 0° C. 12.94 ml of a 2-mol/L trimethylsilyldiazomethane-hexane solution (manufactured by Aldrich) were added to the solution, and stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9445 g of a polymer.

$^1$H-NMR confirmed that the resultant polymer was a copolymer containing 24 mol % of a unit represented by the following formula (B-2) because a peak derived from methyl sulfonate was observed at 3 to 4 ppm.

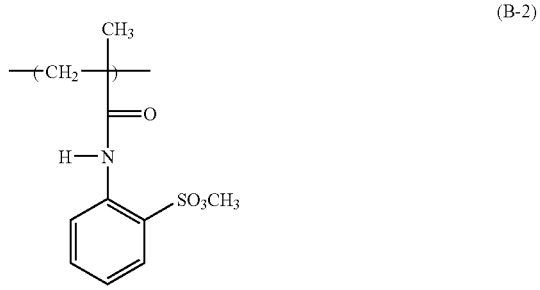
(B-2)

In addition, acid value titration revealed that the sulfonic acid was transformed into methyl sulfonate because no equivalent point derived from the sulfonic acid was observed.

The resultant polymer had a number average molecular weight $M_n$ of 13,000 and a weight average molecular weight $M_w$ of 32,000.

The preparation method was expanded to produce 50 g of the compound. The compound was designated as Exemplified Compound B-2 and used for toner preparation and evaluation.

Example C-1

The same raw material polymer as in Example B-1 was used. Under a nitrogen atmosphere, 1.5003 g of the polymer and 3.3620 g of 4-aminobenzenesulfonic acid were placed in a 200-ml three-necked flask. 56.5 ml of pyridine were added to the flask, and the mixture was stirred. Thereafter, 10.17 ml of triphenyl phosphite were added, and was heated at 120° C. for 6 hours. After completion of the reaction, the resultant was re-precipitated in 565 ml of ethanol, followed by recovery. The resultant polymer was washed with 1-N hydrochloric acid for 1 day, and then, was stirred in water for 1 day to wash the polymer, followed by drying under reduced pressure.

As a result of IR measurement, a peak at 1,695 cm$^{-1}$ derived from a carboxylic acid was reduced, and a peak derived from an amide group was newly observed at 1, 658 cm$^{-1}$.

$^1$H-NMR confirmed that the resultant polymer was a copolymer containing 23 mol % of a unit represented by the following formula (C-1) because a peak derived from an aromatic ring of the 4-aminobenzenesulfonic acid structure shifted.

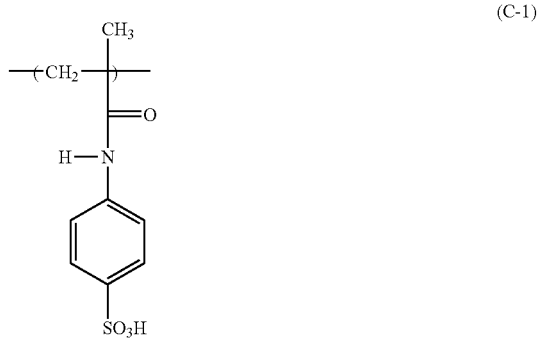
(C-1)

The resultant polymer had a number average molecular weight $M_n$ of 13,000 and a weight average molecular weight $M_w$ of 32,000.

The preparation method was expanded to produce 50 g of the compound. The compound was designated as Exemplified Compound C-1 and used for toner preparation and evaluation.

Example C-2

1.0012 g of the polymer obtained in Example C-1 was placed in a 300-ml round-bottomed flask. Then, 70 ml of chloroform and 17.5 ml of methanol were added to dissolve the polymer, and the solution was cooled to 0° C. 12.94 ml of a 2-mol/L trimethylsilyldiazomethane-hexane solution (manufactured by Aldrich) was added to the solution, and stirred for 4 hours. After completion of the reaction, the solvent was distilled away by using an evaporator, and then the polymer was recovered.

Furthermore, 70 ml of chloroform and 17.5 ml of methanol was added to dissolve the polymer again. Then, the solvent was distilled away by using an evaporator. This operation was repeated 3 times. The recovered polymer was dried under reduced pressure to yield 0.9332 g of a polymer.

$^1$H-NMR confirmed that the resultant polymer was a copolymer containing 22 mol % of a unit represented by the following formula (C-2) because a peak derived from methyl sulfonate was observed at 3 to 4 ppm.

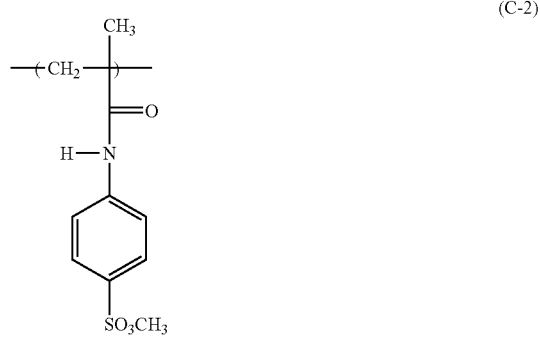

(C-2)

In addition, acid value titration revealed that the sulfonic acid was transformed into methyl sulfonate because no equivalent point derived from the sulfonic acid was observed.

The resultant polymer had a number average molecular weight $M_n$ of 12,000 and a weight average molecular weight $M_w$ of 32,000.

The preparation method was expanded to produce 50 g of the compound. The compound was designated as Exemplified Compound C-2 and used for toner preparation and evaluation.

Example D-1

The same raw material polymer as in Example B-1 was used. Under a nitrogen atmosphere, 1.4980 g of the polymer and 3.3650 g of 3-aminobenzenesulfonic acid were placed in a 200-ml three-necked flask. 56.5 ml of pyridine were added to the flask, and the mixture was stirred. After that, 10.17 ml of triphenyl phosphite were added, and was heated at 120° C. for 6 hours. After completion of the reaction, the resultant was re-precipitated in 565 ml of ethanol, followed by recovery. The resultant polymer was washed with 1-N hydrochloric acid for 1 day, and was then stirred in water for 1 day to wash the polymer, followed by drying under reduced pressure As a result of IR measurement, a peak at 1,695 cm$^{-1}$ derived from a carboxylic acid was reduced, and a peak derived from an amide group was newly observed at 1,658 cm$^{-1}$.

$^1$H-NMR confirmed that the resultant polymer was a copolymer containing 20 mol % of a unit represented by the following formula (D-1) because a peak derived from an aromatic ring of the 3-aminobenzenesulfonic acid structure shifted.

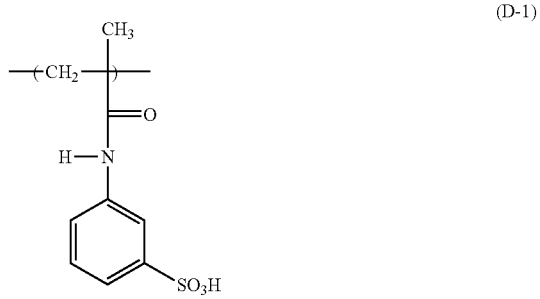

(D-1)

The resultant polymer had a number average molecular weight $M_n$ of 11,000 and a weight average molecular weight $M_w$ of 30,000.

The preparation method was expanded to produce 50 g of the compound. The compound was designated as Exemplified Compound D-1 and used for toner preparation and evaluation.

Example D-2

0.9975 g of the polymer obtained in Example D-1 was placed in a 300-ml round-bottomed flask. Then, 70 ml of chloroform and 17.5 ml of methanol were added to dissolve the polymer, and the solution was cooled to 0° C. 12.94 ml of a 2-mol/L trimethylsilyldiazomethane-hexane solution (manufactured by Aldrich) were added to the solution, and the whole was stirred for 4 hours. After the completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9579 g of a polymer.

H-NMR confirmed that the resultant polymer was a copolymer containing 20 mol % of a unit represented by the following formula (D-2) because a peak derived from methyl sulfonate was observed at 3 to 4 ppm.

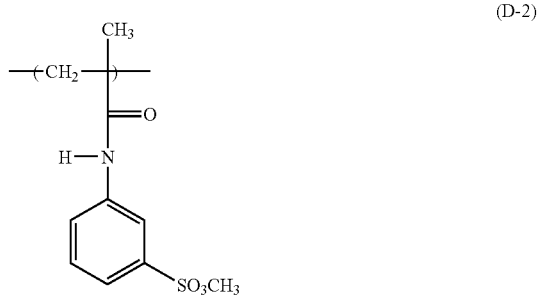

(D-2)

In addition, acid value titration revealed that the sulfonic acid was transformed into methyl sulfonate because no equivalent point derived from the sulfonic acid was observed.

The resultant polymer had a number average molecular weight $M_n$ of 10,000 and a weight average molecular weight $M_w$ of 30,000.

The preparation method was expanded to produce 50 g of the compound. The compound was designated as Exemplified Compound D-2 and used for toner preparation and evaluation.

Example E-1

The same raw material polymer as in Example A-1 was used. Under a nitrogen atmosphere, 1.5012 g of the polymer and 1.4870 g of 4-methoxyaniline-2-sulfonic acid were placed in a 200-ml three-necked flask. 56.5 ml of pyridine were added to the flask, and the mixture was stirred. After that, 3.84 ml of triphenyl phosphite were added, and was heated at 120° C. for 6 hours. After completion of the reaction, the resultant was reprecipitated in 565 ml of ethanol, followed by recovery. The resultant polymer was washed with 1-N hydrochloric acid for 1 day, and was then stirred in water for 1 day to wash the polymer, followed by drying under reduced pressure.

As a result of IR measurement, a peak at 1, 695 $cm^{-1}$ derived from a carboxylic acid was reduced, and a peak derived from an amide group was newly observed at 1,658 $cm^{-1}$.

$^{1}$H-NMR confirmed that the resultant polymer was a copolymer containing 9 mol % of a unit represented by the following formula (E-1) because a peak derived from a methoxy group of 4-methoxyaniline-2-sulfonic acid shifted.

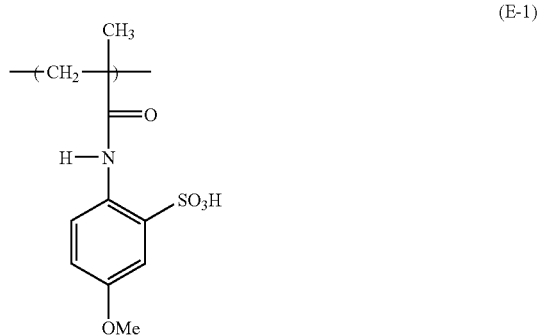

(E-1)

The resultant polymer had a number average molecular weight $M_n$ of 23,000 and a weight average molecular weight $M_w$ of 56,000. The preparation method was expanded to produce 50 g of the compound. The compound was designated as Exemplified Compound E-1 and used for toner preparation and evaluation.

Example E-2

1.0045 g of the polymer obtained in Example E-1 was placed in a 300-ml round-bottomed flask. Then, 70 ml of chloroform and 17.5 ml of methanol were added to dissolve the polymer, and the solution was cooled to 0° C. 4.89 ml of a 2-mol/L trimethylsilyldiazomethane-hexane solution (manufactured by Aldrich) was added to the solution, and was stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9560 g of a polymer.

$^{1}$H-NMR confirmed that the resultant polymer was a copolymer containing 9 mol % of a unit represented by the following formula (E-2) because a peak derived from methyl sulfonate was observed at 3 to 4 ppm.

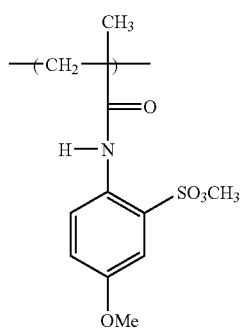

(E-2)

In addition, acid value titration revealed that the sulfonic acid was transformed into methyl sulfonate because no equivalent point derived from the sulfonic acid was observed.

The resultant polymer had a number average molecular weight $M_n$ of 22,000 and a weight average molecular weight $M_w$ of 54,000.

The preparation method was expanded to produce 50 g of the compound. The compound was designated as Exemplified Compound E-2 and used for toner preparation and evaluation.

Example F-1

The same raw material polymer as in Example B-1 was used. Under a nitrogen atmosphere, 1.5068 g of the polymer and 4.8362 g of 4-aminobenzene phenyl sulfonate were placed in a 200-ml three-necked flask. 56.5 ml of pyridine was added to the flask, and the mixture was stirred. Thereafter that, 10.17 ml of triphenyl phosphite was added, and heated at 120° C. for 6 hours. After completion of the reaction, the resultant was re-precipitated in 565 ml of ethanol, followed by recovery. The resultant polymer was washed with 1-N hydrochloric acid for 1 day, and was then stirred in water for 1 day to wash the polymer, followed by drying under reduced pressure.

As a result of IR measurement, a peak at 1,695 $cm^{-1}$ derived from a carboxylic acid was reduced, and a peak derived from an amide group was newly observed at 1,658 $cm^{-1}$.

$^{1}$H-NMR confirmed that the resultant polymer was a copolymer containing 25 mol % of a unit represented by the following formula (F-1) because a peak derived from an aromatic ring of the 4-aminobenzene phenyl sulfonate structure shifted.

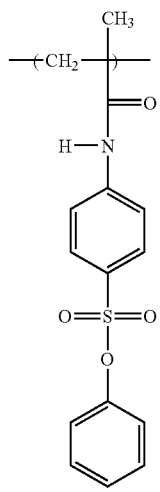

(F-1)

The resultant polymer had a number average molecular weight $M_n$ of 13,000 and a weight average molecular weight $M_w$ of 32,000.

The preparation method was expanded to produce 50 g of the compound. The compound was designated as Exemplified Compound F-1 and used for toner preparation and evaluation.

Example G-1

The same raw material polymer as in Example B-1 was used. Under a nitrogen atmosphere, 1.4889 g of the polymer and 4.8381 g of 2-aminobenzene phenyl sulfonate were placed in a 200-ml three-necked flask. 56.5 ml of pyridine was added to the flask, and the mixture was stirred. Thereafter, 10.17 ml of triphenyl phosphite was added, and heated at 120° C. for 6 hours. After completion of the reaction, the resultant was re-precipitated in 565 ml of ethanol, followed by recovery. The resultant polymer was washed with 1-N hydrochloric acid for 1 day, and then, was stirred in water for 1 day to wash the polymer, followed by drying under reduced pressure.

As a result of IR measurement, a peak at 1,695 cm$^{-1}$ derived from a carboxylic acid was reduced, and a peak derived from an amide group was newly observed at 1,658 cm$^{-1}$.

$^1$H-NMR confirmed that the resultant polymer was a copolymer containing 0.22 mol % of a unit represented by the following formula (G-1) because a peak derived from an aromatic ring of the 2-aminobenzene phenyl sulfonate structure shifted.

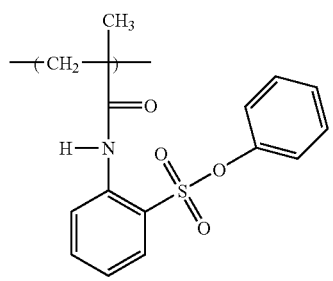

(G-1)

The resultant polymer had a number average molecular weight $M_n$ of 13,000 and a weight average molecular weight $M_w$ of 33,000.

The preparation method was expanded to produce 50 g of the compound. The compound was designated as Exemplified Compound G-1 and used for toner preparation and evaluation.

Example H-1

The same raw material polymer as that of Example B-1 was used. Under a nitrogen atmosphere, 1.5001 g of the polymer and 4.3320 g of 2-amino-1-naphthalenesulfonic acid were placed in a 200-ml three-necked flask. 56.5 ml of pyridine were added to the flask, and the mixture was stirred. After that, 10.17 ml of triphenyl phosphite were added, and the whole was heated at 120° C. for 6 hours. After the completion of the reaction, the resultant was re-precipitated in 565 ml of ethanol, followed by recovery. The resultant polymer was washed with 1-N hydrochloric acid for 1 day, and then, was stirred in water for 1 day to wash the polymer, followed by drying under reduced pressure.

As a result of IR measurement, a peak at 1,695 cm$^{-1}$ derived from a carboxylic acid was reduced, and a peak derived from an amide group was newly observed at 1,658 cm$^{-1}$.

$^1$H-NMR confirmed that the resultant polymer was a copolymer containing 20 mol % of a unit represented by the following formula (H-1) because a peak derived from a naphthyl structure of 2-amino-1-naphthalenesulfonic acid shifted.

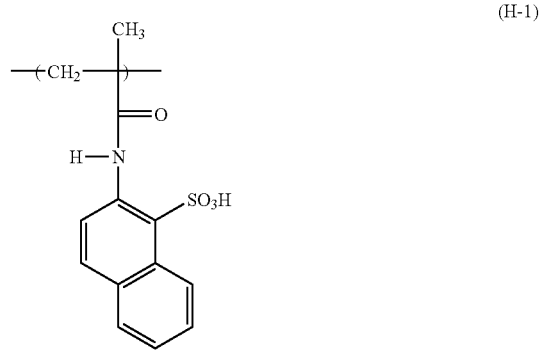

(H-1)

The resultant polymer had a number average molecular weight $M_n$ of 12,000 and a weight average molecular weight $M_w$ of 34,000.

The preparation method was expanded to produce 50 g of the compound. The compound was designated as Exemplified Compound H-1 and used for toner preparation and evaluation.

Example H-2

0.9879 g of the polymer obtained in Example H-1 was placed in a 300-ml round-bottomed flask. Then, 70 ml of chloroform and 17.5 ml of methanol were added to dissolve the polymer, and the solution was cooled to 0° C. 12.94 ml of a 2-mol/L trimethylsilyldiazomethane-hexane solution, (manufactured by Aldrich) was added to the solution, and stirred for 4 hours. After completion of the reaction, the solvent was distilled away by using an evaporator, and then the polymer was recovered. Furthermore, 70 ml of chloroform and 17.5 ml of methanol was added to dissolve the polymer again. Then, the solvent was distilled away by using an evaporator. This operation was repeated 3 times. The recovered polymer was dried under reduced pressure to yield 0.9662 g of a polymer.

$^1$H-NMR confirmed that the resultant polymer was a copolymer containing 20 mol % of a unit represented by the following formula (H-2) because a peak derived from methyl sulfonate was observed at 3 to 4 ppm.

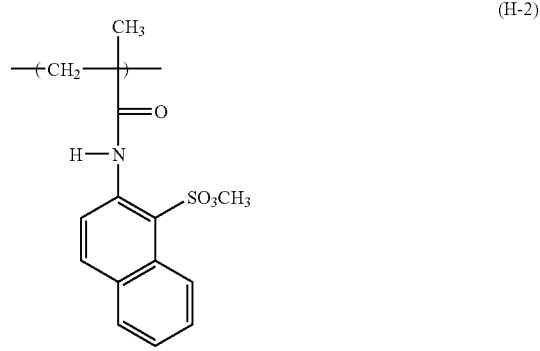

(H-2)

In addition, acid value titration revealed that the sulfonic acid was transformed into methyl sulfonate because no equivalent point derived from the sulfonic acid was observed.

The resultant polymer had a number average molecular weight $M_n$ of 11,000 and a weight average molecular weight $M_w$ of 32,000.

The preparation method was expanded to produce 50 g of the compound. The compound was designated as Exemplified Compound H-2 and used for toner preparation and evaluation.

Example I-1

The same raw material polymer as in Example A-1 was used.

Under a nitrogen atmosphere, 1.5060 g of the polymer and 1.6342 g of 1-naphthylamine-8-sulfonic acid were placed in a 200-ml three-necked flask. 56.5 ml of pyridine was added to the flask, and the mixture was stirred. Thereafter, 3.84 ml of triphenyl phosphite were added, and heated at 120° C. for 6 hours. After completion of the reaction, the resultant was re-precipitated in 565 ml of ethanol, followed by recovery. The resultant polymer was washed with 1-N hydrochloric acid for 1-day, and was then stirred in water for 1 day to wash the polymer, followed by drying under reduced pressure.

As a result of IR measurement, a peak at 1,695 cm$^{-1}$ derived from a carboxylic acid was reduced, and a peak derived from an amide group was newly observed at 1,658 cm$^{-1}$. $^{1}$H-NMR confirmed that the resultant polymer was a copolymer containing 7 mol % of a unit represented by the following formula (I-1) because a peak derived from a naphthyl structure of 1-naphthylamine-8-sulfonic acid shifted.

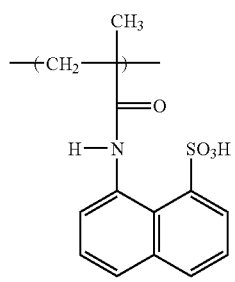

(I-1)

The resultant polymer had a number average molecular weight $M_n$ of 21,000 and a weight average molecular weight $M_w$ of 48,000.

The preparation method was expanded to produce 50 g of the compound. The compound was designated as Exemplified Compound I-1 and used for toner preparation and evaluation.

Example I-2

1.0025 g of the polymer obtained in Example I-1 was placed in a 300-ml round-bottomed flask. Then, 70 ml of chloroform and 17.5 ml of methanol were added to dissolve the polymer, and the solution was cooled to 0° C. 4.89 ml of a 2-mol/L trimethylsilyldiazomethane-hexane solution (manufactured by Aldrich) were added to the solution, and the whole was stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9668 g of a polymer.

$^{1}$H-NMR confirmed that the resultant polymer was a copolymer containing 7 mol % of a unit represented by the following formula (I-2) because a peak derived from methyl sulfonate was observed at 3 to 4 ppm.

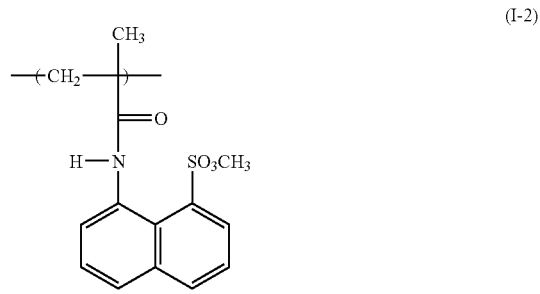

(I-2)

In addition, acid value titration revealed that the sulfonic acid was transformed into methyl sulfonate because no equivalent point derived from the sulfonic acid was observed.

The resultant polymer had a number average molecular weight $M_n$ of 20,000 and a weight average molecular weight $M_w$ of 46,000.

The preparation method was expanded to produce 50 g of the compound. The compound was designated as Exemplified Compound I-2 and used for toner preparation and evaluation.

Example J-1

The same raw material polymer as in Example A-1 was used. Under a nitrogen atmosphere, 1.5052 g of the polymer and 1.1200 g of 2-amino-2-methylpropanesulfonic acid were placed in a 200-ml three-necked flask. 56.5 ml of pyridine was added to the flask, and the mixture was stirred. Thereafter, 3.84 ml of triphenyl phosphite was added, and heated at 120° C. for 6 hours. After completion of the reaction, the resultant was re-precipitated in 565 ml of ethanol, followed by recovery. The resultant polymer was washed with 1-N hydrochloric acid for 1 day, and then, was stirred in water for 1 day to wash the polymer, followed by drying under reduced pressure.

As a result of IR measurement, a peak at 1,695 cm$^{-1}$ derived from a carboxylic acid reduced, and a peak derived from an amide group was newly observed at 1,668 cm$^{-1}$. $^{1}$H-NMR confirmed that the resultant polymer was a copolymer containing 8 mol % of a unit represented by the following formula (J-1) because a peak derived from a methyl group of 2-amino-2-methylpropanesulfonic acid shifted.

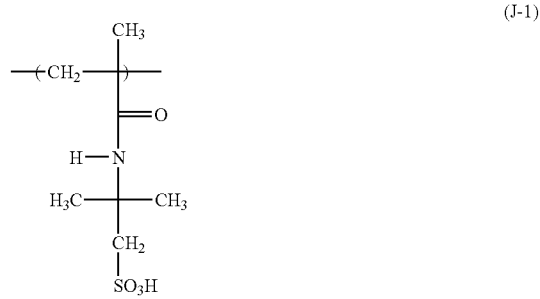

(J-1)

The resultant polymer had a number average molecular weight $M_n$ of 20,000 and a weight average molecular weight $M_w$ of 46,000.

The preparation method was expanded to produce 50 g of the compound. The compound was designated as Exemplified Compound J-1 and used for toner preparation and evaluation.

Example J-2

0.9985 g of the polymer obtained in Example J-1 was placed in a 300-ml round-bottomed flask. Then, 70 ml of chloroform and 17.5 ml of methanol were added to dissolve the polymer, and the solution was cooled to 0° C. 4.89 ml of a 2-mol/L trimethylsilyldiazomethane-hexane solution (manufactured by Aldrich) was added to the solution, and stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9350 g of a polymer.

$^1$H-NMR confirmed that the resultant polymer was a copolymer containing 8 mol % of a unit represented by the following formula (J-2) because a peak derived from methyl sulfonate was observed at 3 to 4 ppm.

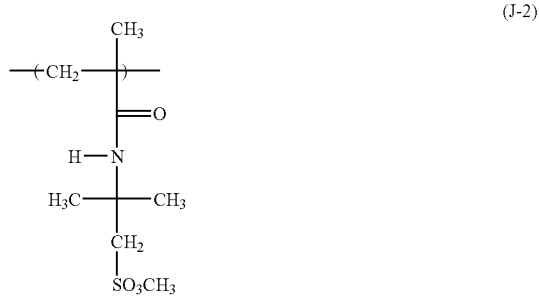

(J-2)

In addition, acid value titration revealed that the sulfonic acid was transformed into methyl sulfonate because no equivalent point derived from the sulfonic acid was observed.

The resultant polymer had a number average molecular weight $M_n$ of 18,000 and a weight average molecular weight $M_w$ of 38,000.

The preparation method was expanded to produce 50 g of the compound. The compound was designated as Exemplified Compound J-2 and used for toner preparation and evaluation.

Example K-1

The same raw material polymer as in Example B-1 was used. Under a nitrogen atmosphere, 1.5043 g of the polymer and 2.4256 g of taurine were placed in a 200-ml three-necked flask. 56.5 ml of pyridine was added to the flask, and the mixture was stirred. Thereafter, 10.17 ml of triphenyl phosphite was added, and heated at 120° C. for 6 hours. After completion of the reaction, the resultant was re-precipitated in 565 ml of ethanol, followed by recovery. The resultant polymer was washed with 1-N hydrochloric acid for 1 day, and then, was stirred in water for 1 day to wash the polymer, followed by drying under reduced pressure.

As a result of IR measurement, a peak at 1,695 cm$^{-1}$ derived from a carboxylic acid was reduced, and a peak derived from an amide group was newly observed at 1,668 cm$^{-1}$. $^1$H-NMR confirmed that the resultant polymer was a copolymer containing 15 mol % of a unit represented by the following formula (K-1) because a peak derived from a methylene structure of taurine shifted.

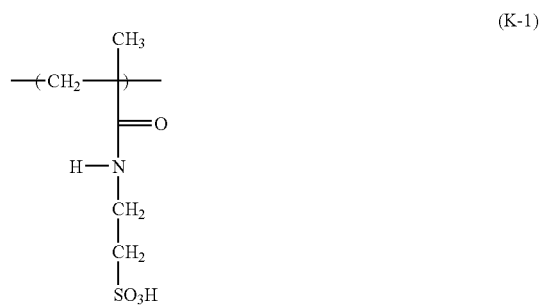

(K-1)

The resultant polymer had a number average molecular weight $M_n$ of 10,000 and a weight average molecular weight $M_w$ of 33,000.

The preparation method was expanded to produce 50 g of the compound. The compound was designated as Exemplified Compound K-1 and used for toner preparation and evaluation.

Example K-2

1.0002 g of the polymer obtained in Example K-1 was placed in a 300-ml round-bottomed flask. Then, 70 ml of chloroform and 17.5 ml of methanol were added to dissolve the polymer, and the solution was cooled to 0° C. 12.94 ml of a 2-mol/L t-rimethylsilyldiazomethane-hexane solution (manufactured by Aldrich) was added to the solution, and stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9652 g of a polymer.

$^1$H-NMR confirmed that the resultant polymer was a copolymer containing 15 mol % of a unit represented by the following formula (K-2) because a peak derived from methyl sulfonate was observed at 3 to 4 ppm. In addition, acid value titration revealed that the sulfonic acid was transformed into methyl sulfonate because no equivalent point derived from the sulfonic acid was observed.

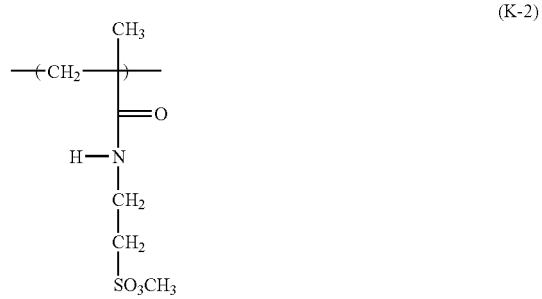

(K-2)

The resultant polymer had a number average molecular weight $M_n$ of 10,000 and a weight average molecular weight $M_w$ of 32,000.

85

The preparation method was expanded to produce 50 g of the compound. The compound was designated as Exemplified Compound K-2 and used for toner preparation and evaluation.

Example L-1

In accordance with JOURNAL OF POLYMER SCIENCE: Polymer Chemistry Edition, 15, 585-591 (1977), 100 g of a compound represented by the following formula (L-0) were synthesized and used for an experiment.

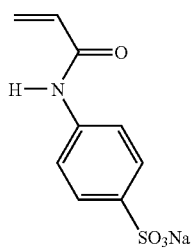

(L-0)

The resultant compound was desalted by using an ion-exchange resin. With reference to SYNTHETIC COMMUNICATIONS, 15 (12), 21, 1057-1062 (1985), a compound represented by the following formula (L-1) was synthesized.

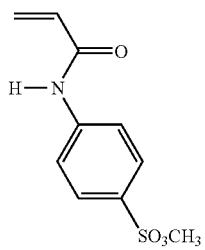

(L-1)

In a stream of nitrogen, 2.0010 g of the desalted product of the compound represented by the chemical formula (L-0), 20 ml of trimethyl orthoformate, and p-benzoquinone as a polymerization inhibitor were placed in a flask, and heated at 70° C. for 5 hours. The reaction mixture was cooled and concentrated under reduced pressure. The resultant was washed with 3 L of water twice, washed with 3 L of hexane twice, and dissolved into chloroform again. Thereafter, the solution was dried with anhydrous magnesium sulfate to distill the solvent off.

Figure 8:
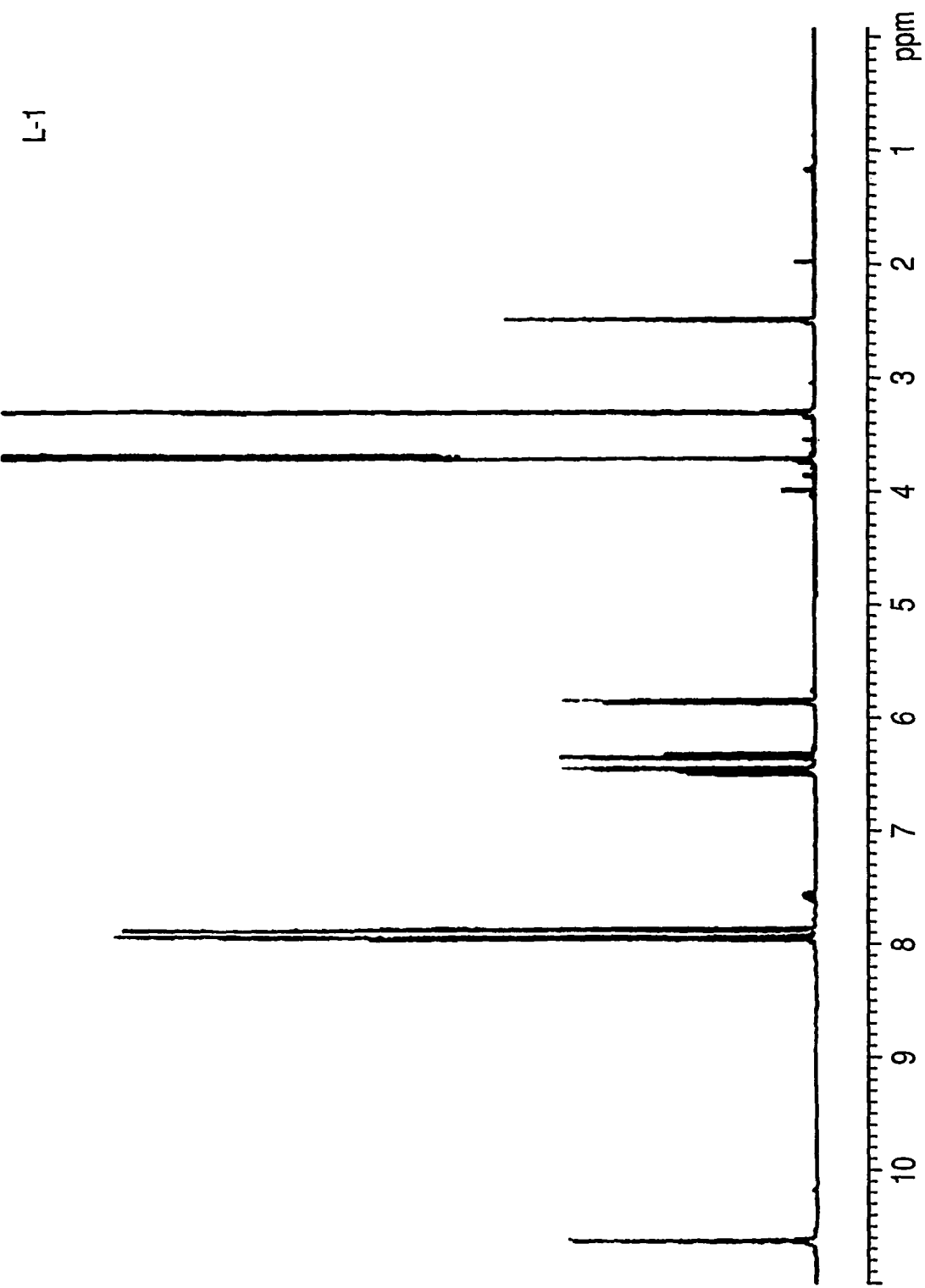
FIG. 8 shows a 1H-NMR chart of the compound L-1 synthesized in Example L-1.

The structure of the resultant compound was determined by means of $^1$H-NMR (FT-NMR: Bruker DPX 400; resonance frequency: 400 Hz; measured nuclear species: $^1$H; solvent used: $D_2O$; measurement temperature: room temperature). $^1$H-NMR confirmed that the sulfonic acid was transformed into methyl sulfonate because a peak derived from methyl sulfonate was observed at 3 to 4 ppm. The resulting $^1$H-NMR chart is shown in FIG. 8.

In addition, elemental analysis confirmed that the abundance of Na was within a detection limit. This suggests that methyl esterification has proceeded.

Acid value titration using an electric potential titration device AT510 (manufactured by Kyoto Electronics Manufacturing) revealed that the sulfonic acid was transformed into methyl sulfonate because no equivalent point derived from the sulfonic acid was observed.

The monomer was used for the subsequent polymerization.

86

Example L-2

0.3015 g of the monomer obtained in Example L-1 and 2.7 ml of styrene were placed in a 30-mL test tube with a ground-glass stopper, and then 20 ml of DMSO were added to dissolve them. The resultant was subjected to nitrogen bubbling for 12 hours for deaeration.

41.2 mg of 2,2'-azobis(isobutyronitrile) was dissolved as an initiator in 5.0 ml of DMSO, and was added to the test tube. Then, the mixture was stirred under heating at 70° C. 9 hours after, the resultant polymer was re-precipitated in methanol, and then, was washed with water to remove an unreacted monomer and a homopolymer of (L-1), thereby recovering 0.9681 g of a polymer.

$^1$H-NMR confirmed that the resultant polymer was a copolymer containing 5 mol % of a unit represented by the following formula (L-2).

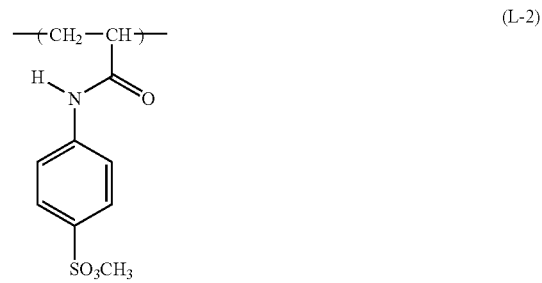

(L-2)

In addition, acid value titration revealed that methyl sulfonate was polymerized without being deesterified because no equivalent point derived from the sulfonic acid was observed.

The resultant polymer had a number average molecular weight $M_n$ of 10,000 and a weight average molecular weight $M_w$ of 22,000.

The preparation method was expanded to produce 50 g of the compound. The compound was designated as Exemplified Compound L-2 and used for toner preparation and evaluation.

Example M-0

With reference to JOURNAL OF POLYMER SCIENCE: Polymer Chemistry Edition, 15, 585-591 (1977), a compound represented by the following formula (M-0) was synthesized.

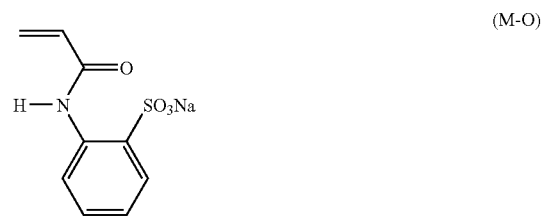

(M-0)

2-Aminobenzenesulfonic acid (50.0 g) was neutralized with sodium hydroxide (12.0 g) in 120 ml water and the solution was heated to dissolve all the salts. After sodium bicarbonate (24.5 g) and picric acid (1.8 g) were added, acryloyl chloride (26.1 g) was added dropwise for 2 hr at room temperature. The solution was stirred for 30 minutes and cooled to 0° C., and the resulting precipitate was recovered by filtration. The precipitate was washed to produce 8.5 g of pure monomer.

The structure of the resultant compound was determined by means of $^1$H-NMR (FT-NMR: Bruker DPX 400; resonance frequency: 400 Hz; measured nuclear species: $^1$H; solvent used: D$_2$O; measurement temperature: room temperature).

The monomer obtained here was used for the subsequent polymerization.

Example M-1

0.3117 g of the monomer obtained in Example M-0 and 2.7 ml of styrene were placed in a 30-mL test tube with a ground-glass stopper, and then 20 ml of DMSO were added to dissolve them. The resultant was subjected to nitrogen bubbling for 12 hours for deaeration.

41.2 mg of 2,2'-azobis(isobutyronitrile) was dissolved as an initiator into 5.0 ml of DMSO, and was added to the test tube. Then, the mixture was stirred under heating at 70° C. 9 hours after, the resultant polymer was purified by using a dialysis membrane, and then, was washed with water and hydrochloric acid to remove an unreacted monomer and a homopolymer of (M-0), thereby recovering 0.9681 g of a polymer.

$^1$H-NMR confirmed that the resultant polymer was a copolymer containing a unit represented by the following formula (M-1) in a content ratio (mol %) of (MM):(MF) =95:5 because a peak derived from a phenyl structure of (M-0) shifted.

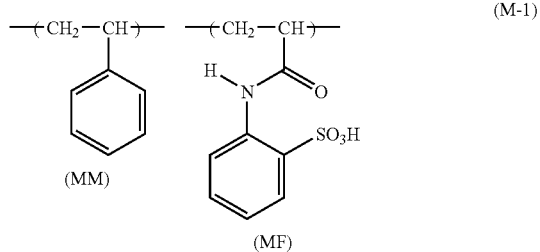

The resultant polymer had a number average molecular weight M$_n$ of 11,600 and a weight average molecular weight M$_w$ of 23,500.

The preparation method was expanded to produce 50 g of the compound. The compound was designated as Exemplified Compound M-1 and used for toner preparation and evaluation.

Example M-2

0.2995 g of the polymer obtained in Example M-1 was placed in a 100-ml round-bottomed flask. Then, 21 ml of chloroform and 5.25 ml of methanol were added to dissolve the polymer, and cooled to 0° C. 0.68 ml of a 2-mol/L trimethylsilyldiazomethane-hexane solution (manufactured by Aldrich) was added to the solution, and stirred for 4 hours. After completion of the reaction, the solvent was distilled away by using an evaporator, and then the polymer was recovered. Furthermore, 21 ml of chloroform and 5.25 ml of methanol were added to dissolve the polymer again. Then, the solvent was distilled away by using an evaporator. This operation was repeated 3 times. The recovered polymer was dried under reduced pressure to yield 0.2880 g of a polymer.

$^1$H-NMR confirmed that the resultant polymer was a copolymer containing 5 mol % of a unit represented by the following formula (M-2) because a peak derived from methyl sulfonate was observed at 3 to 4 ppm.

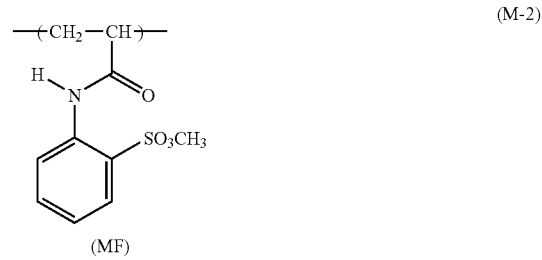

In addition, acid value titration revealed that the sulfonic acid was transformed into methyl sulfonate because no equivalent point derived from the sulfonic acid was observed.

The resultant polymer had a number average molecular weight M$_n$ of 11,000 and a weight average molecular weight M$_w$ of 23,000.

The preparation method was expanded to produce 50 g of the compound. The compound was designated as Exemplified Compound M-2 and used for toner preparation and evaluation.

Example N-1

With reference to JOURNAL OF POLYMER SCIENCE: Polymer Chemistry Edition, 13, 1879-1887 (1975), a copolymer containing a unit represented by the following formula (N-0) in a content ratio (mol %) of (NM):(NF)=0.94:6 was obtained by copolymerization of acrylic acid with styrene and used for the following experiment.

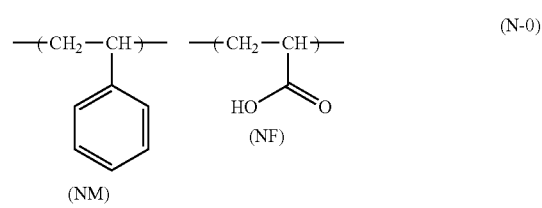

Under a nitrogen atmosphere, 1.5012 g of the polymer and 1.2868 g of 2-aminobenzenesulfonic acid were placed in a 200-ml three-necked flask. 56.5 ml of pyridine was added to the flask, and the mixture was stirred. Thereafter, 3.89 ml of triphenyl phosphite was added, and heated at 120° C. for 6 hours. After completion of the reaction, pyridine was distilled away, and the residue was dissolved into 150 ml of ethyl acetate. The resultant was repeatedly subjected to separation washing 3 times using 2-N hydrochloric acid for purification. Furthermore, the solvent was distilled away, and the polymer was dissolved in 15 ml of THF and was re-precipitated in 200 ml of 2-propanol. Thereafter, the precipitate was recovered by filtration and dried under reduced pressure.

$^1$H-NMR confirmed that the resultant polymer was a copolymer containing 6 mol % of a unit represented by the following formula (N-1) because a peak derived from a phenyl group of 2-aminobenzenesulfonic acid shifted.

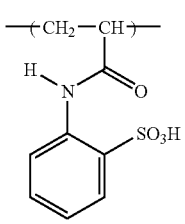

(N-1)

The resultant polymer had a number average molecular weight $M_n$ of 23,000 and a weight average molecular weight $M_w$ of 54,000.

The preparation method was expanded to produce 50 g of the compound. The compound was designated as Exemplified Compound N-1 and used for toner preparation and evaluation.

Example N-2

Figure 9:
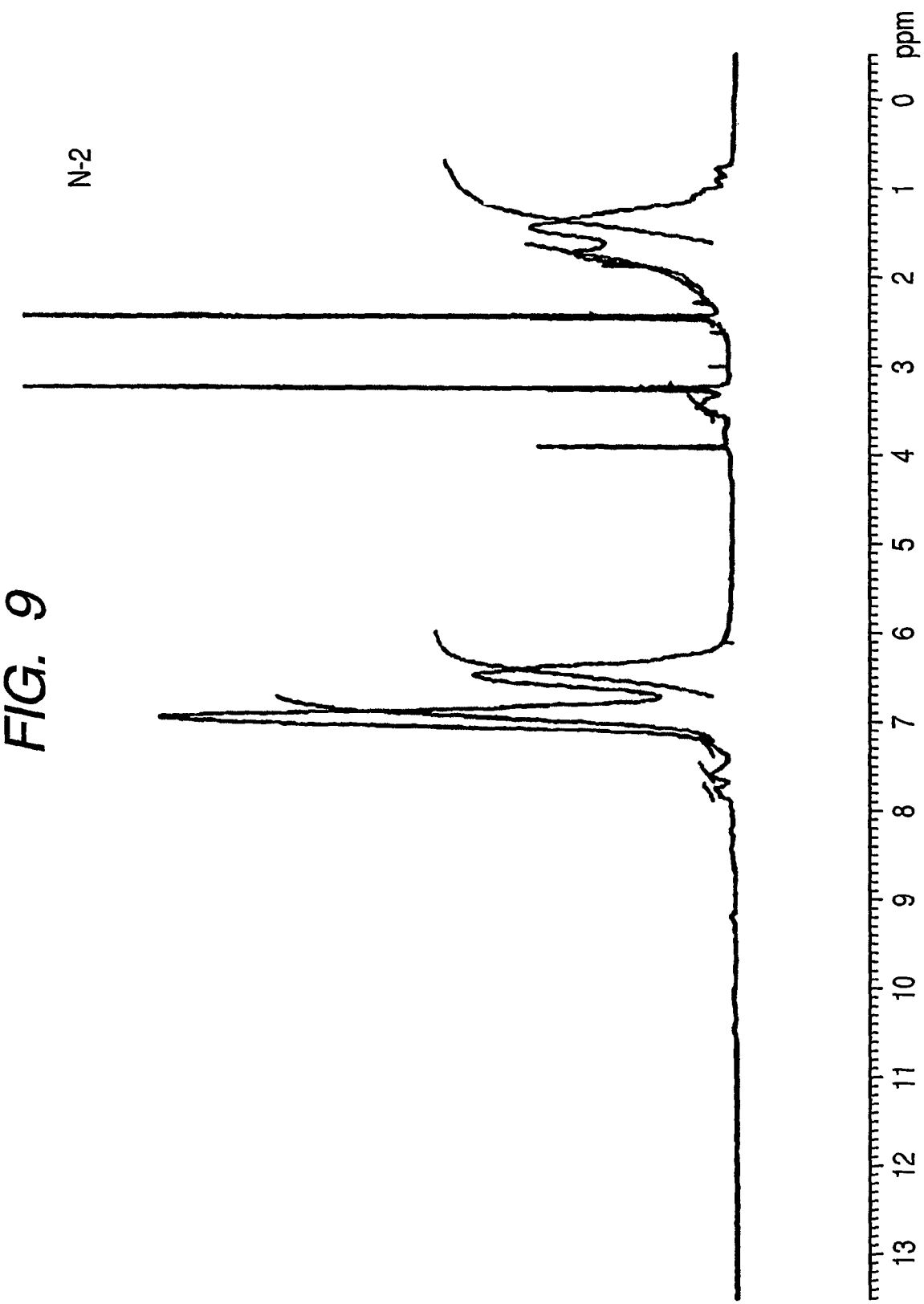
FIG. 9 shows a 1H-NMR chart of the polymer produced in Example N-2, having a unit represented by the formula N-2.

0.9980 g of the polymer obtained in Example N-1 was placed in a 300-ml round-bottomed flask. Then, 70 ml of chloroform and 17.5 ml of methanol were added to dissolve the polymer, and cooled to 0° C. 4.95 ml of a 2-mol/L trimethylsilyldiazomethane-hexane solution (manufactured by Aldrich) was added to the solution, and stirred for 4 hours. After completion of the reaction, the solvent was distilled away by using an evaporator, and then the polymer was recovered. Furthermore, 70 ml of chloroform and 17.5 ml of methanol was added to dissolve the polymer again. Then, the solvent was distilled away by using an evaporator. This operation was repeated 3 times. The recovered polymer was dried under reduced pressure to yield 0.9898 g of a polymer. $^1$H-NMR confirmed that the resultant polymer was a copolymer containing 6 mol % of a unit represented by the following formula (N-2) because a peak derived from methyl sulfonate was observed at 3 to 4 ppm. The resulting $^1$H-NMR chart is shown in FIG. 9.

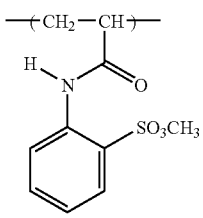

(N-2)

In addition, acid value titration revealed that the sulfonic acid was transformed into methyl sulfonate because no equivalent point derived from the sulfonic acid was observed.

The resultant polymer had a number average molecular weight $M_n$ of 22,000 and a weight average molecular weight $M_w$ of 54,000.

The preparation method was expanded to produce 50 g of the compound. The compound was designated as Exemplified Compound N-2 and used for toner preparation and evaluation.

Example P-1

The same raw material polymer as in Example N-1 was used. Under a nitrogen atmosphere, 1.4998 g of the polymer and 1.5099 g of 4-methoxyaniline-2-sulfonic acid were placed in a 200-ml three-necked flask. 56.5 ml of pyridine was added to the flask, and stirred. Thereafter, 3.89 ml of triphenyl phosphite was added, and heated at 120° C. for 6 hours. After completion of the reaction, pyridine was distilled away, and the residue was dissolved into 150 ml of ethyl acetate. The resultant was repeatedly subjected to separatory washing 3 times using 2-N hydrochloric acid for purification. Furthermore, the solvent was distilled away, and the polymer was dissolved into 15 ml of THF and was re-precipitated in 200 ml of 2-propanol. After that, the precipitate was recovered by filtration and dried under reduced pressure.

$^1$H-NMR confirmed that the resultant polymer was a copolymer containing 6 mol % of a unit represented by the following formula (P-1) because a peak derived from a phenyl group of 4-methoxyaniline-2-sulfonic acid shifted.

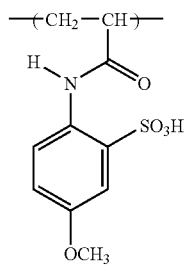

(P-1)

The resultant polymer had a number average molecular weight $M_n$ of 23,000 and a weight average molecular weight $M_w$ of 54,000.

The preparation method was expanded to produce 50 g of the compound. The compound was designated as Exemplified Compound P-1 and used for toner preparation and evaluation.

Example P-2

1.0045 g of the polymer obtained in Example P-1 was added to a 300-ml round-bottomed flask. Then, 70 ml of chloroform and 17.5 ml of methanol were added to dissolve the polymer, and cooled to 0° C. 4.95 ml of a 2-mol/L trimethylsilyldiazomethane-hexane solution (manufactured by Aldrich) was added to the solution, and stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9898 g of a polymer.

$^1$H-NMR confirmed that the resultant polymer was a copolymer containing 6 mol % of a unit represented by the following formula (P-2) because a peak derived from methyl sulfonate was observed at 3 to 4 ppm.

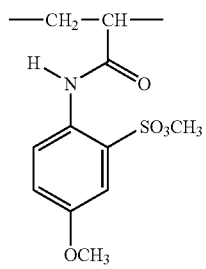

In addition, acid value titration revealed that the sulfonic acid was transformed into methyl sulfonate because no equivalent point derived from the sulfonic acid was observed.

The resultant polymer had a number average molecular weight $M_n$ of 22,000 and a weight average molecular weight $M_w$ of 54,000.

The preparation method was expanded to produce 50 g of the compound. The compound was designated as Exemplified Compound P-2 and used for toner preparation and evaluation.

Example Q-1

The same raw material polymer as in Example N-1 was used. Under a nitrogen atmosphere, 1.4998 g of the polymer and 1.6588 g of 2-amino-1-naphthalenesulfonic acid were placed in a 200-ml three-necked flask. 56.5 ml of pyridine was added to the flask, and stirred. Thereafter, 3.89 ml of triphenyl phosphite were added, and heated at 120° C. for 6 hours. After completion of the reaction, pyridine was distilled away, and the residue was dissolved in 150 ml of ethyl acetate. The resultant was repeatedly subjected to separatory washing 3 times using 2-N hydrochloric acid for purification. Furthermore, the solvent was distilled away, and the polymer was dissolved in 15 ml of THF and was re-precipitated in 200 ml of 2-propanol. Thereafter, the precipitate was recovered by filtration and dried under reduced pressure.

$^1$H-NMR confirmed that the resultant polymer was a copolymer containing 2 mol % of a unit represented by the following formula (Q-1) because a peak derived from a naphthalene group of 2-amino-1-naphthalenesulfonic acid shifted.

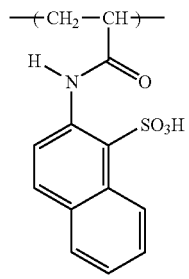

(Q-1)

The resultant polymer had a number average molecular weight $M_n$ of 23,000 and a weight average molecular weight $M_w$ of 54,000.

The preparation method was expanded to produce 50 g of the compound. The compound was designated as Exemplified Compound Q-1 and used for toner preparation and evaluation.

Example Q-2

1.0054 g of the polymer obtained in Example Q-1 was placed in a 300-ml round-bottomed flask. Then, 70 ml of chloroform and 17.5 ml of methanol were added to dissolve the polymer, and cooled to 0° C. 4.95 ml of a 2-mol/L trimethylsilyldiazomethane-hexane solution (manufactured by Aldrich) was added to the solution, and stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9898 g of a polymer.

$^1$H-NMR confirmed that the resultant polymer was a copolymer containing 2 mol % of a unit represented by the following formula (Q-2) because a peak derived from methyl sulfonate was observed at 3 to 4 ppm.

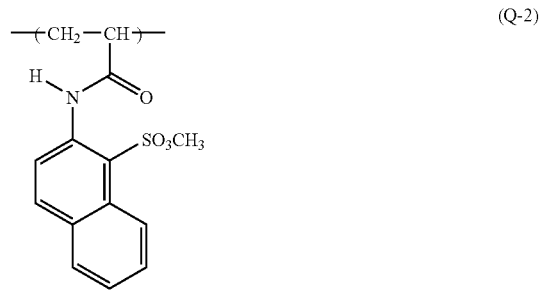

(Q-2)

In addition, acid value titration revealed that the sulfonic acid was transformed into methyl sulfonate because no equivalent point derived from the sulfonic acid was observed.

The resultant polymer had a number average molecular weight $M_n$ of 22,000 and a weight average molecular weight $M_w$ of 54,000.

The preparation method was expanded to produce 50 g of the compound. The compound was designated as Exemplified Compound Q-2 and used for toner preparation and evaluation.

Example R-1

The same raw material polymer as in Example N-1 was used. Under a nitrogen atmosphere, 1.4998 g of the polymer and 1.1383 g of 2-amino-2-methylpropanesulfonic acid were placed in a 200-ml three-necked flask. 56.5 ml of pyridine was added to the flask, and stirred. Thereafter, 3.89 ml of triphenyl phosphite was added, and heated at 120° C. for 6 hours. After completion of the reaction, pyridine was distilled away, and the residue was dissolved in 150 ml of ethyl acetate. The resultant was repeatedly subjected to separatory washing 3 times using 2-N hydrochloric acid for purification. Furthermore, the solvent was distilled away, and the polymer was dissolved into 15 ml of THF and was re-precipitated in 200 ml of 2-propanol. After that, the precipitate was recovered by filtration and dried under reduced pressure.

$^1$H-NMR confirmed that the resultant polymer was a copolymer containing 3 mol % of a unit represented by the following formula (R-1) because a peak derived from a methyl group of 2-amino-2-methylpropanesulfonic acid shifted.

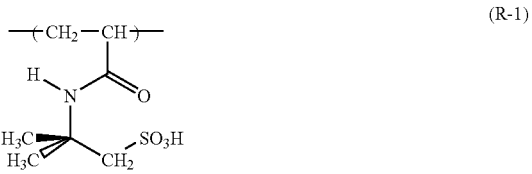

(R-1)

The resultant polymer had a number average molecular weight $M_n$ of 23,000 and a weight average molecular weight $M_w$ of 54,000.

Example R-2

0.9985 g of the polymer obtained in Example R-1 was placed in a 300-ml round-bottomed flask. Then, 70 ml of chloroform and 17.5 ml of methanol were added to dissolve the polymer, and cooled to 0° C. 4.95 ml of a 2-mol/L trimethylsilyldiazomethane-hexane solution (manufactured by Aldrich) was added to the solution, and stirred for 4 hours. After completion of the reaction, the solvent was distilled away by using an evaporator, and then the polymer was recovered. Furthermore, 70 ml of chloroform and 17.5 ml of methanol were added to dissolve the polymer again. Then, the solvent was distilled away by using an evaporator. This operation was repeated 3 times. The recovered polymer was dried under reduced pressure to yield 0.9898 g of a polymer.

$^1$H-NMR confirmed that the resultant polymer was a copolymer containing 2 mol % of a unit represented by the following formula (R-2) because a peak derived from methyl sulfonate was observed at 3 to 4 ppm.

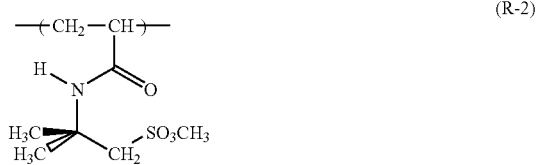

(R-2)

In addition, acid value titration revealed that the sulfonic acid was transformed into methyl sulfonate because no equivalent point derived from the sulfonic acid was observed.

The resultant polymer had a number average molecular weight $M_n$ of 22,000 and a weight average molecular weight $M_w$ of 54,000.

The preparation method was expanded to produce 50 g of the compound. The compound was designated as Exemplified Compound R-2 and used for toner preparation and evaluation.

Next, various toners were produced by using a charge control agent produced by a method selected from the methods of the present invention, and were evaluated (Examples 1 to 40).

Example 1

First, an aqueous solution of $Na_3PO_4$ was added to a 2-L four-necked flask equipped with a high-speed stirring device TK Homomixer. The number of revolutions was adjusted to 10,000 rpm, and the solution was heated to 60° C. An aqueous solution of $CaCl_2$ was gradually added to the solution to prepare an aqueous dispersion medium containing a minute and hardly water-soluble dispersant $Ca_3(PO_4)_2$. Meanwhile, the following compositions were dispersed for 3 hours by using a ball mill. Then, 10 parts by weight of a releasing agent (ester wax) and 10 parts by weight of 2,2'-azobis(2,4-dimethylvaleronitrile) as a polymerization initiator were added to prepare a polymerizable monomer composition.

| | |
|---|---|
| Styrene monomer: | 82 parts by weight |
| Ethylhexyl acrylate: | 18 parts by weight |
| Divinylbenzene monomer: | 0.1 part by weight |
| Cyan colorant (C.I. Pigment Blue 15): | 6 parts by weight |
| Polyethylene oxide resin (having a molecular weight of 3,200 and an acid value of 8): | 5 parts by weight |
| Exemplified Compound H-2: | 2 parts by weight |

Next, the polymerizable monomer composition thus obtained was charged into the aqueous dispersion medium prepared in advance, and granulated while the number of revolutions was kept at 10,000 rpm.

Thereafter, the resultant was allowed to react at 65° C. for 3 hours while being stirred with a paddle stirring blade, and then, was polymerized at 80° C. for 6 hours to complete the polymerization reaction. After completion of the reaction, the resulting suspension was cooled, to which an acid was added to dissolve the hardly water-soluble dispersant $Ca_3(PO_4)_2$. Then, the resultant was filtered, washed with water, and dried to yield blue polymerized particles (1). The grain size of the resultant blue polymerized particles (1) was measured by means of a Coulter Counter Multisizer (manufactured by Coulter). The particles had a weight average particle size of 7.5 µm and a fine powder amount (an abundance ratio of particles each having a particle size of 3.17 µm or less in number distribution) of 5.1 number %.

1.3 parts by weight of hydrophobic silica fine powder treated with hexamethyldisilazane (BET: 270 $m^2$/g) as a fluidity improver were dry-mixed with and externally added to 100 parts by weight of the blue polymerized particles (1) thus prepared by using a Henschel mixer, thereby producing a blue toner (1) of this example. Furthermore, 7 parts by weight of the blue toner (1) and 93 parts by weight of a resin-coated magnetic ferrite carrier (average particle size: 45 µm) were mixed to prepare a two-component blue developer (1) for magnetic brush development.

Examples 2 to 5

Each of blue toners (2) to (5) of Examples 2 to 5 was produced in the same manner as in Example 1 except that Exemplified Compound H-2 was changed to any one of Exemplified Compounds B-1, F-1, H-1, and P-1. The properties of the toners were measured in the same manner as in Example 1. Table 1 shows the results. In addition, the toners were used to prepare two-component blue developers (2) to (5) of Examples 2 to 4 in the same manner as in Example 1.

Comparative Example 1

A blue toner (6) of Comparative Example 1 was produced in the same manner as in Example 1 except that no exemplified compound was used. The properties of the toner were measured in the same manner as in Example 1. Table-1 shows the results. In addition, the toner was used to prepare a two-component blue developer (6) of Comparative Example 1 in the same manner as in Example 1.

(Evaluation)

Toner charge amounts of the two-component blue developers (1) to (5) prepared in Example 1 and the two-component blue developer (6) prepared in Comparative Example 1 10 sec and 300 sec after stirring in a normal-temperature-and-normal-humidity (25° C., 60% RH) environment and a high-temperature-and-high-humidity (30° C., 80% RH) environment were measured by means of the method of measuring a charge amount as described above. Then, the measured value of a two-component blow-off charge amount was rounded to the first decimal place, and the resultant value was evaluated according to the following criteria. Table 1 summarizes the results.

(Chargeability)

⊚: Very good (−20 µC/g or less)
○: Good (−19.9 to −10.0 µC/g)
Δ: Practicable (−9.9 to −5.0 µC/g)
x: Not practicable (−4.9 µC/g or more)

Examples 6 to 10

Each of yellow toners (1) to (5) of Examples 6 to 10 was produced in the same manner as in Example 1 except that: 2.0 parts by weight of each of Exemplified Compounds B-2, L-1, M-1, J-2, and Q-1 were used; and a yellow colorant (Hansa yellow G) was used instead of the cyan colorant. The properties of the toners were measured in the same manner as in Example 1. Table 1 shows the results. In addition, the toners were used to prepare two-component yellow developers (1) to (5) in the same manner as in Example 1.

Comparative Example 2

A yellow toner (6) of Comparative Example 2 was produced in the same manner as in Example 1 except that: no exemplified compound was used; and a yellow colorant (Hansa yellow G) was used instead of the cyan colorant. The properties of the toner were measured in the same manner as in Example 1. Table 1 shows the results. In addition, the toner was used to prepare a two-component yellow developer (6) of Comparative Example 2 in the same manner as in Example 1.

(Evaluation)

Toner charge amounts of the two-component yellow developers (1) to (5) prepared in Examples 6 to 10 and the two-component yellow developer (6) prepared in Comparative Example 210 sec and 300 sec after stirring in a normal-temperature-and-normal-humidity (25° C., 60% RH) environment and a high-temperature-and-high-humidity (30° C., 80% RH) environment were measured by means of the method of measuring a charge amount as described above. Then, the measured value of a two-component blow-off charge amount was rounded to the first decimal place, and the resultant value was evaluated according to the following criteria. Table 1 summarizes the results.

(Chargeability)
◉: Very good (−20 µC/g or less)
○: Good (−19.9 to −10.0 µC/g)
Δ: Practicable (−9.9 to −5.0 µC/g)
x: Not practicable (−4.9 µC/g or more)

Examples 11 to 15

Each of black toners (1) to (5) of Examples 11 to 15 was produced in the same manner as in Example 1 except that: 2.0 parts by weight of each of Exemplified Compounds K-2, C-1, G-1, I-2, and N-1 were used; and carbon black (DBP oil absorption 110 mL/100 g) was used instead of the cyan colorant. The properties of the toners were measured in the same manner as in Example 1. Table 1 shows the results. In addition, the toners were used to prepare two-component black developers (1) to (5) in the same manner as in Example 1.

Comparative Example 3

A black toner (6) of Comparative Example 3 was produced in the same manner as in Example 1 except that: no exemplified compound was used; and carbon black (DBP oil absorption 110 mL/100 g) was used instead of the cyan colorant. The properties of the toner were measured in the same manner as in Example 1. Table 1 shows the results. In addition, the toner was used to prepare a two-component black developer (6) of Comparative Example 3 in the same manner as in Example 1.

(Evaluation)

Toner charge amounts of the two-component black developers (1) to (5) prepared in Examples 11 to 15 and the two-component black developer (6) prepared in Comparative Example 3 10 sec and 300 sec after stirring in a normal-temperature-and-normal-humidity (25° C., 60% RH) environment and a high-temperature-and-high-humidity (30° C., 80% RH) environment were measured by means of the method of measuring a charge amount as described above. Then, the measured value of a two-component blow-off charge amount was rounded to the first decimal place, and the resultant value was evaluated according to the following criteria. Table 1 summarizes the results.

(Chargeability)
◉: Very good (−20 µC/g or less)
○: Good (−19.9 to −10.0 µC/g)
Δ: Practicable (−9.9 to −5.0 µC/g)
x: Not practicable (−4.9 µC/g or more)

Example 16

| | |
|---|---|
| Styrene-butyl acrylate copolymer resin (having a glass transition temperature of 70° C.): | 100 parts by weight |
| Magenta pigment (C.I. Pigment Red 114): | 5 parts by weight |
| Exemplified Compound N-2: | 2 parts by weight |

The above compositions were mixed, and the mixture was melted and kneaded by means of a biaxial extruder (L/D=30). The kneaded product was cooled, roughly pulverized by means of a hammer mill, and finely pulverized by means of a jet mill. Thereafter, the finely pulverized product was classified to yield magenta colored particles (1). The grain size of the magenta colored particles (1) was measured. The particles had a weight average particle size of 7.2 µm and a fine powder amount of 5.7 number %.

1.5 parts by weight of hydrophobic silica fine powder treated with hexamethyldisilazane (BET: 250 m$^2$/g) as a fluidity improver were dry-mixed with 100 parts by weight of the magenta colored particles (1) by using a Henschel mixer, thereby producing a magenta toner (1) of this example. Furthermore, 7 parts by weight of the resultant magenta toner (1) and 93 parts by weight of a resin-coated magnetic ferrite carrier (average particle size: 45 µm) were mixed to prepare a two-component magenta developer (1) for magnetic brush development.

Examples 17 to 20

Each of magenta toners (2) to (5) of Examples 17 to 20 was produced in the same manner as in Example 16 except that Exemplified Compound N-2 was changed to any one of Exemplified Compounds C-2, I-1, R-2, and M-2. The properties of the toners were measured in the same manner as in Example 1. Table 1 shows the results. In addition, the toners were used to prepare two-component magenta developers (2) to (5) of Examples 17 to 20 in the same manner as in Example 16.

Comparative Example 4

A magenta toner (6) of Comparative Example 4 was produced in the same manner as in Example 16 except that no exemplified compound was used. The properties of the toner were measured in the same manner as in Example 1. Table 1 shows the results. In addition, the toner was used to prepare a two-component magenta developer (6) of Comparative Example 4 in the same manner as in Example 16.

(Evaluation)

Toner charge amounts of the two-component magenta developers (1) to (5) prepared in Examples 17 to 20 and the two-component magenta developer (6) prepared in Comparative Example 410 sec and 300 sec after stirring in a normal-temperature-and-normal-humidity (25° C., 60% RH) environment and a high-temperature-and-high-humidity (30° C., 80% RH) environment were measured by means of the method of measuring a charge amount as described above. Then, the measured value of a two-component blow-off charge amount was rounded to the first decimal place, and the resultant value was evaluated according to the following criteria. Table 1 summarizes the results.

(Chargeability)
◉: Very good (−20 µC/g or less)
○: Good (−19.9 to −10.0 µC/g)
Δ: Practicable (−9.9 to −5.0 µC/g)
x: Not practicable (−4.9 µC/g or more)

Examples 21 to 25

Each of black toners (7) to (11) of Examples 21 to 25 was produced in the same manner as in Example 16 except that: 2.0 parts by weight of each of Exemplified Compounds A-2, D-1, E-2, P-2, and M-2 were used; and carbon black (DBP oil absorption 110 mL/100 g) was used instead of the magenta pigment. The properties of the toners were measured in the same manner as in Example 1. Table 1 shows the results. In addition, the toners were used to prepare two-component black developers (7) to (11) in the same manner as in Example 16.

Comparative Example 5

A black toner (12) of Comparative Example 5 was produced in the same manner as in Example 16 except that: no exemplified compound was used; and carbon black (DBP oil absorption 110 mL/100 g) was used instead of the magenta pigment. The properties of the toner were measured in the same manner as in Example 1. Table 1 shows the results. In addition, the toner was used to prepare a two-component black developer (12) of Comparative Example 5 in the same manner as in Example 16.

(Evaluation)
Toner charge amounts of the two-component black developers (7) to (11) prepared in Examples 21 to 25 and the two-component black developer (12) prepared in Comparative Example 510 sec and 300 sec after stirring in a normal-temperature-and-normal-humidity (25° C., 60% RH) environment and a high-temperature-and-high-humidity (30° C., 80% RH) environment were measured by means of the method of measuring a charge amount as described above. Then, the measured value of a two-component blow-off charge amount was rounded to the first decimal place, and the resultant value was evaluated according to the following criteria. Table 1 summarizes the results.

(Chargeability)
◉: Very good (−20 µC/g or less)
○: Good (−19.9 to −10.0 µC/g)
Δ: Practicable (−9.9 to −5.0 µC/g)
x: Not practicable (−4.9 µC/g or more)

Example 26

| | |
|---|---|
| Polyester resin: | 100 parts by weight |
| Carbon black (DBP oil absorption 110 mL/100 g): | 5 parts by weight |
| Exemplified Compound E-1: | 2 parts by weight |

The polyester resin was synthesized as follows. 751 parts of an adduct of bisphenol A with 2 moles of propylene oxide, 104 parts of terephthalic acid, and 167 parts of trimellitic anhydride were subjected to polycondensation by using 2 parts of dibutyltin oxide as a catalyst to produce the polyester resin having a softening point of 125° C.

The above compositions were mixed, and the mixture was melted and kneaded by means of a biaxial extruder (L/D=30). The kneaded product was cooled, roughly crushed by means of a hammer mill, and finely pulverized by means of a jet mill. Thereafter, the finely pulverized product was classified to yield black colored particles (13). The grain size of the black colored particles (13) was measured. The particles had a weight average particle size of 7.6 µm and a fine powder amount of 4.9 number %.

1.5 parts by weight of hydrophobic silica fine powder treated with hexamethyldisilazane (BET: 250 m$^2$/g) as a fluidity improver were dry-mixed with 100 parts by weight of the black colored particles (13) by using a Henschel mixer, thereby producing a black toner (13) of this example. Furthermore, 7 parts by weight of the resultant black toner (13) and 93 parts by weight of a resin-coated magnetic ferrite carrier (average particle size: 45 µm) were mixed to prepare a two-component black developer (13) for magnetic brush development.

Examples 27 to 30

Each of black toners (14) to (17) of Examples 27 to 30 was produced in the same manner as in Example 26 except that Exemplified Compound E-1 was changed to any one of Exemplified Compounds A-1, D-2, Q-2, and N-2. The properties of the toners were measured in the same manner as in Example 1. Table 1 shows the results. In addition, the toners were used to prepare two-component black developers (14) to (17) of Examples 27 to 30 in the same manner as in Example 26.

Comparative Example 6

A black toner (18) of Comparative Example 6 was produced in the same manner as in Example 26 except that no exemplified compound was used. The properties of the toner were measured in the same manner as in Example 1. Table 1 shows the results. In addition, the toner was used to prepare a two-component black developer (18) of Comparative Example 6 in the same manner as in Example 26.

(Evaluation)
Toner charge amounts of the two-component black developers (13) to (17) prepared in Examples 26 to 30 and the two-component black developer (18) prepared in Comparative Example 610 sec and 300 sec after stirring in a normal-temperature-and-normal-humidity (25° C., 60% RH) environment and a high-temperature-and-high-humidity (30° C., 80% RH) environment were measured by means of the method of measuring a charge amount as described above. Then, the measured value of a two-component blow-off charge amount was rounded to the first decimal place, and the resultant value was evaluated according to the following criteria. Table 1 summarizes the results.

(Chargeability)
◉: Very good (−20 µC/g or less)
○: Good (−19.9 to −10.0 µC/g)
Δ: Practicable (−9.9 to −5.0 µC/g)
x: Not practicable (−4.9 µC/g or more)

TABLE 1

| Example | Exemplified Compound No. | Toner No. | Particle size distribution Average particle size (μm) | Fine powder amount (%) | Chargeability Normal temperature and normal humidity (Q/M) 10 Sec | 300 Sec | High temperature and high humidity (Q/M) 10 Sec | 300 Sec |
|---|---|---|---|---|---|---|---|---|
| 1 | H-2 | Blue 1 | 7.5 | 5.1 | ⊚ | ⊚ | ⊚ | ⊚ |
| 2 | B-1 | Blue 2 | 7.6 | 5.5 | ⊚ | ⊚ | ⊚ | ⊚ |
| 3 | F-1 | Blue 3 | 6.9 | 5.1 | ⊚ | ⊚ | ⊚ | ⊚ |
| 4 | H-1 | Blue 4 | 7.3 | 5.6 | ⊚ | ⊚ | ⊚ | ⊚ |
| 5 | P-1 | Blue 5 | 7.2 | 5.5 | ⊚ | ⊚ | ⊚ | ⊚ |
| 6 | B-2 | Yellow 1 | 7.4 | 5.0 | ⊚ | ⊚ | ⊚ | ⊚ |
| 7 | L-1 | Yellow 2 | 7.0 | 5.3 | ⊚ | ⊚ | ⊚ | ⊚ |
| 8 | M-1 | Yellow 3 | 7.0 | 5.2 | ⊚ | ⊚ | ⊚ | ⊚ |
| 9 | J-2 | Yellow 4 | 6.9 | 4.8 | ⊚ | ⊚ | ⊚ | ⊚ |
| 10 | Q-1 | Yellow 5 | 7.2 | 5.0 | ⊚ | ⊚ | ⊚ | ⊚ |
| 11 | K-2 | Black 1 | 7.4 | 5.1 | ⊚ | ⊚ | ⊚ | ⊚ |
| 12 | C-1 | Black 2 | 7.3 | 5.5 | ⊚ | ⊚ | ⊚ | ⊚ |
| 13 | G-1 | Black 3 | 7.3 | 5.1 | ⊚ | ⊚ | ⊚ | ⊚ |
| 14 | I-2 | Black 4 | 7.3 | 5.1 | ⊚ | ⊚ | ⊚ | ⊚ |
| 15 | N-1 | Black 5 | 7.2 | 5.0 | ⊚ | ⊚ | ⊚ | ⊚ |
| 16 | N-2 | Magenta 1 | 7.2 | 5.7 | ⊚ | ⊚ | ⊚ | ⊚ |
| 17 | C-2 | Magenta 2 | 7.3 | 5.4 | ⊚ | ⊚ | ⊚ | ⊚ |
| 18 | I-1 | Magenta 3 | 7.0 | 5.2 | ⊚ | ⊚ | ⊚ | ⊚ |
| 19 | R-2 | Magenta 4 | 7.1 | 5.9 | ⊚ | ⊚ | ⊚ | ⊚ |
| 20 | M-2 | Magenta 5 | 7.1 | 5.5 | ⊚ | ⊚ | ⊚ | ⊚ |
| 21 | A-2 | Black 7 | 7.2 | 4.8 | ⊚ | ⊚ | ⊚ | ⊚ |
| 22 | D-1 | Black 8 | 7.5 | 5.7 | ⊚ | ⊚ | ⊚ | ⊚ |
| 23 | E-2 | Black 9 | 7.1 | 5.4 | ⊚ | ⊚ | ⊚ | ⊚ |
| 24 | P-2 | Black 10 | 7.4 | 5.4 | ⊚ | ⊚ | ⊚ | ⊚ |
| 25 | M-2 | Black 11 | 7.2 | 5.4 | ⊚ | ⊚ | ⊚ | ⊚ |
| 26 | E-1 | Black 13 | 7.6 | 4.9 | ⊚ | ⊚ | ⊚ | ⊚ |
| 27 | A-1 | Black 14 | 7.2 | 5.7 | ⊚ | ⊚ | ⊚ | ⊚ |
| 28 | D-2 | Black 15 | 7.2 | 5.6 | ⊚ | ⊚ | ⊚ | ⊚ |
| 29 | Q-2 | Black 16 | 7.5 | 5.5 | ⊚ | ⊚ | ⊚ | ⊚ |
| 30 | N-2 | Black 17 | 7.2 | 5.2 | ⊚ | ⊚ | ⊚ | ⊚ |
| Comparative example 1 | — | Blue 6 | 7.1 | 5.2 | X | X | X | X |
| 2 | — | Yellow 6 | 7.3 | 5.4 | X | X | X | X |
| 3 | — | Black 6 | 7.1 | 5.1 | X | Δ | X | Δ |
| 4 | — | Red 6 | 7.5 | 5.6 | X | Δ | X | Δ |
| 5 | — | Black 12 | 7.6 | 5.7 | X | Δ | X | X |
| 6 | — | Black 18 | 7.6 | 4.9 | X | Δ | X | Δ |

Examples 31 to 36 and Comparative Examples 7 to 12

First, an example of an image forming apparatus used for an image forming method of each of Examples 31 to 36 and Comparative Examples 7 to 12 will be described.

FIG. 1 is a schematic sectional view for explaining an image forming apparatus for performing an image forming method of each of examples and comparative examples of the present invention. A photosensitive drum 1 shown in FIG. 1 has a photosensitive layer 1a having an organic photoconductor on a substrate 1b, and is structured to rotate in a direction indicated by an arrow. The surface of the photosensitive drum 1 is charged to a surface potential of about −600 V by a charging roller 2 serving as a charging member which is opposite to the photosensitive drum 1 and rotates while being in contact with the drum. As shown in FIG. 1, the charging roller 2 is structured by coating a core bar 2b with a conductive elastic layer 2a.

Figure 2:
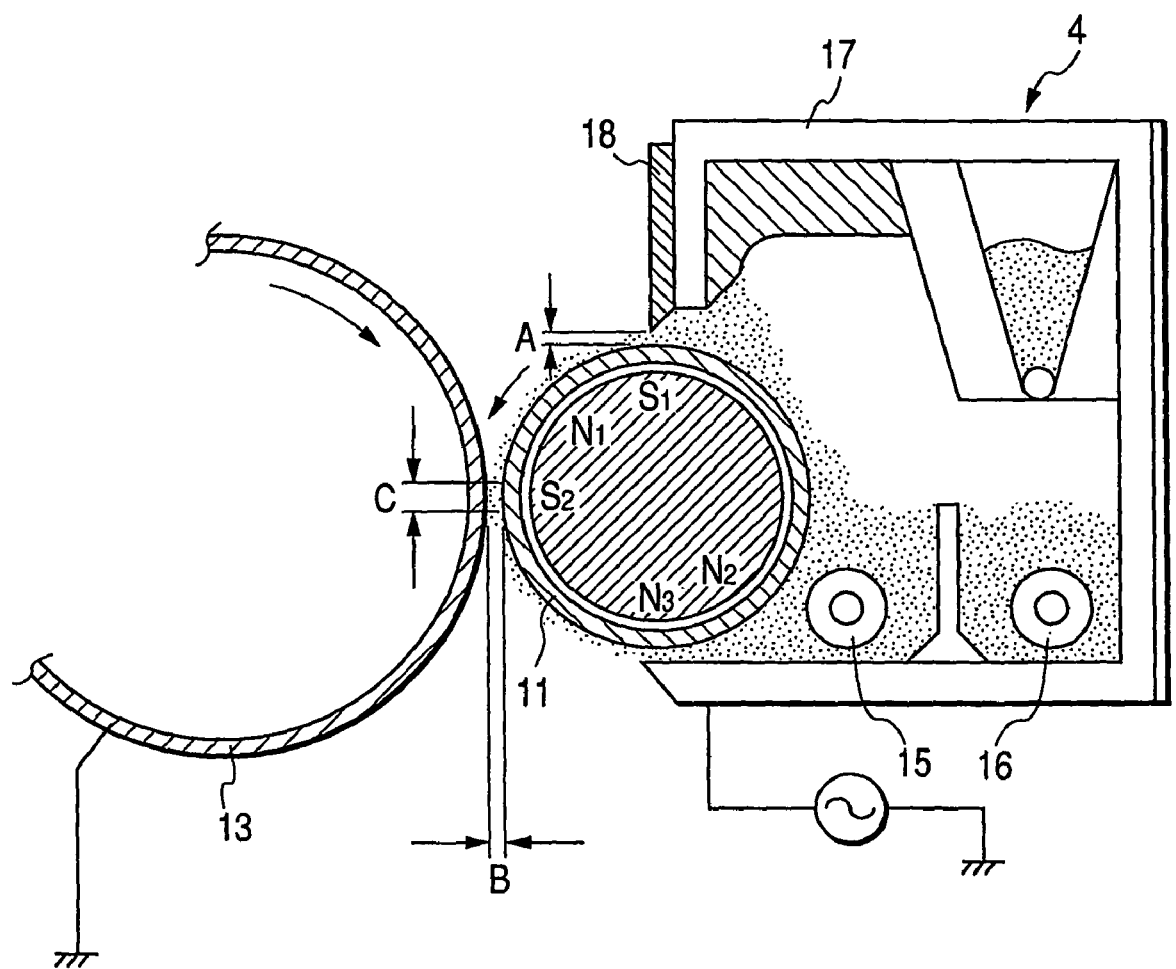
FIG. 2 is a sectional view of a main part of a developing device for a two-component developer used in each of Examples 31 to 36 and Comparative Examples 7 to 12.

Next, the photosensitive drum 1 whose surface is charged is exposed to light 3, where an electrostatic charge image having an exposed-area potential of −100 V and a dark-area potential of −600 V is formed on the photosensitive member by turning on/off the light in accordance with digital image information using a polygon mirror. Subsequently, the electrostatic charge image on the photosensitive drum 1 is subjected to reversal development by using multiple developing devices 4-1, 4-2, 4-3, and 4-4, and visualized. As a result, a toner image is formed on the photosensitive drum 1, where each of the two-component developers prepared in Examples 1, 6, 11, 16, 21, and 26 and Comparative Examples 1 to 6 is used as a developer. Thus, a toner image is formed by means of a yellow toner, a magenta toner, a cyan toner, or a black toner. FIG. 2 is an enlarged sectional view of each developing device 4 for a two-component developer used at that time.

In FIG. 2, reference numeral 11 denotes a developer carrier; 13, a photosensitive drum; 15, a conveyance screw; 16, a stirring screw; 17, a developer container; and 18, a developer regulating member.

Next, the toner image on the photosensitive drum 1 is transferred onto an intermediate transfer member 5 rotating while being in contact with the photosensitive drum 1. As a result, a visualized image having 4 colors overlapping one another is formed on the intermediate transfer member 5. The transfer residual toner that remains on the photosensitive drum 1 without being transferred is recovered in a residual toner container 9 by a cleaner member 8.

As shown in FIG. 1, the intermediate transfer member 5 is composed of a core bar 5b as a support and an elastic layer 5a applied on the core bar 5b. In this example, the intermediate transfer member 5 was used which was obtained by coating the pipe-shaped core bar 5b with the elastic layer 5b obtained by sufficiently dispersing carbon black as a conductivity imparting material into nitrile-butadiene rubber (NBR). The hardness of the elastic layer 5b measured in accordance with "JIS K-6301" was 30 degrees, and the elastic layer had a volume resistivity of $10^9$ Ω·cm. A transfer current necessary for transfer from the photosensitive drum 1 onto the intermediate transfer member 5 was about 5 μA, which was obtained by applying +500 V from a power source to the core bar 5b.

The visualized image having 4 toner colors overlapping one another formed on the intermediate transfer member 5 is transferred onto an image-receiving material such as paper by a transfer roller 7, and then, is fixed by a heat-fixing device H. The transfer roller 7 has a core bar 7b having an outer diameter of 10 mm coated with an elastic layer 7a obtained by sufficiently dispersing carbon as a conductivity imparting material into a foam of an ethylene-propylene-diene-based tertiary copolymer (EPDM). The elastic layer had a volume specific resistivity of $10^6$ Ω·cm and a hardness of 35 degrees measured in accordance with "JIS K-6301". A transfer current of 15 μA was allowed to flow by applying a voltage to the transfer roller 7.

Figure 5:
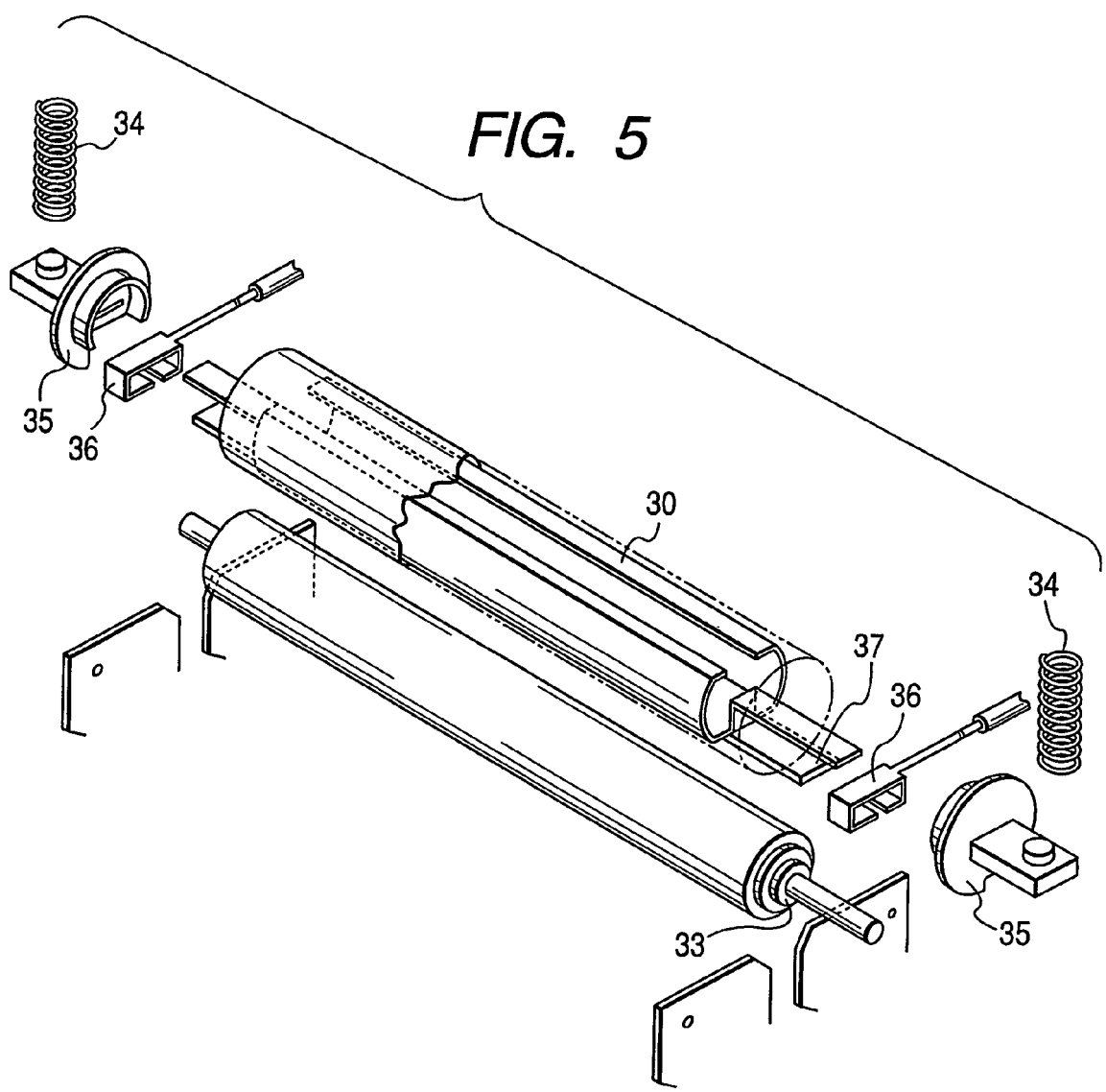
FIG. 5 is an exploded perspective view of a main part of a fixing device used in each example of the present invention.
Figure 6:
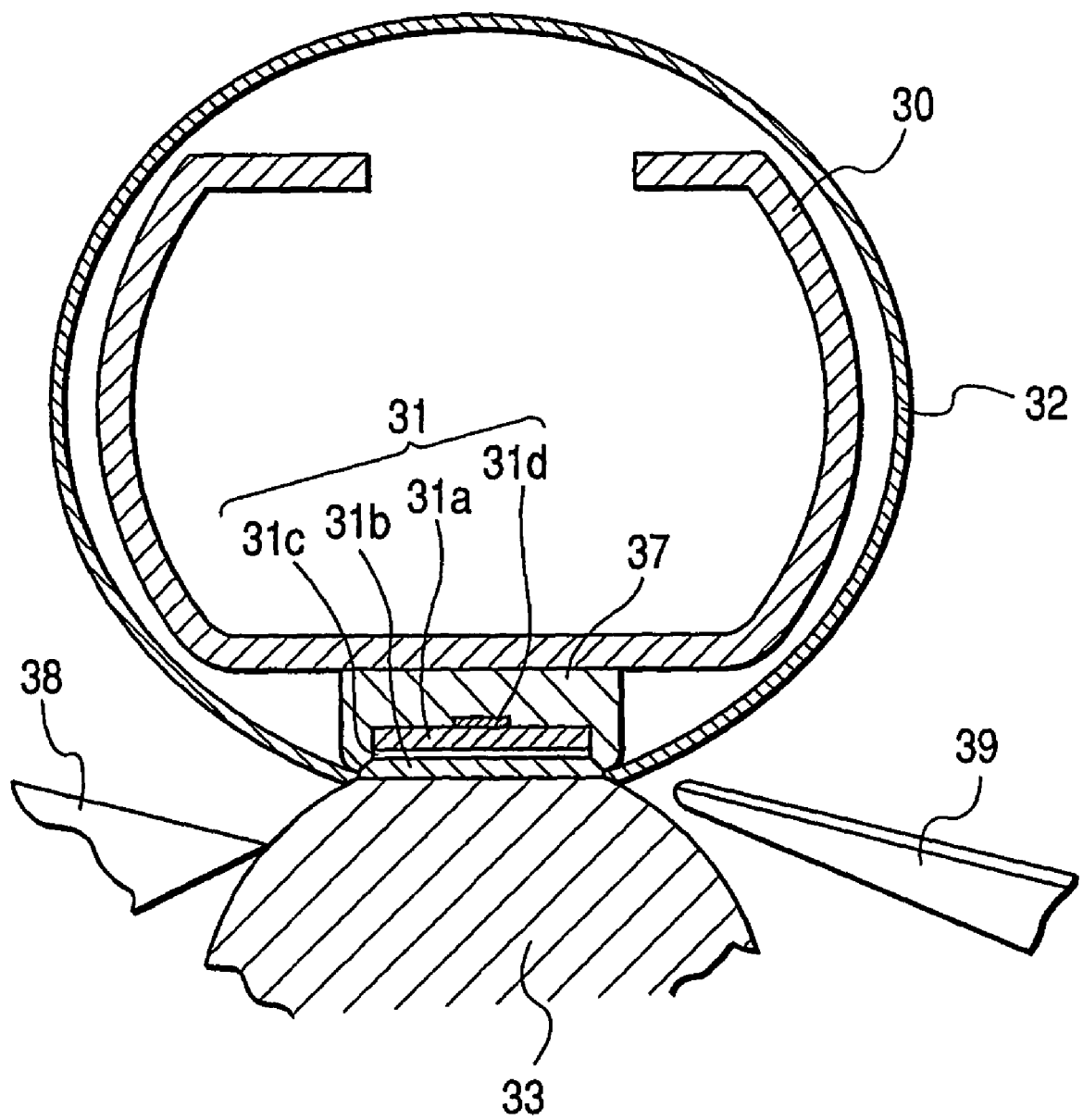
FIG. 6 is an enlarged sectional view of the main part of the fixing device used in each example of the present invention showing a film state at the time of non-driving.

In the apparatus shown in FIG. 1, a heat-roll fixing device having no oil application mechanism shown in each of FIG. 5 and FIG. 6 was used as the heat-fixing device H. At this time, a roller having a surface layer made of a fluorine-based resin was used for each of an upper roller and a lower roller. In addition, each roller had a diameter of 60 mm. A fixing temperature at the time of fixing was set at 160° C., while a nip width was set to be 7 mm. The transfer residual toner on the photosensitive drum 1 recovered by cleaning was conveyed to a developing unit by a reuse mechanism for recycle.

In FIG. 1, reference numeral 6 denotes an image-receiving material, reference numeral 10 denotes a cleaning portion, and reference symbol H denotes a heat-fixing device.

(Evaluation)

Under the above conditions, a print out test was performed in a monochrome intermittent mode (that is, a mode in which a developing unit is suspended for 10 sec every time one sheet is printed out, and deterioration in toner is accelerated by a preliminary operation at the time of restart) in a normal-temperature-and-normal-humidity (25° C., 60% RH) environment and a high-temperature-and-high-humidity (30° C., 80% RH) environment at a print out rate of 8 sheets (A4 size)/min using each of the two-component developers prepared by using the toners of Examples 1, 6, 11, 16, 21, and 26 and the two-component developers prepared by using the toners of Comparative Examples 1 to 6 while sequentially supplying the developer. The resultant printed-out image was evaluated for the following items. Table 2 summarizes the results of the evaluation.

(Printed-Out Image Evaluation)

1. Image Density

A predetermined number of sheets of ordinary plain paper for a copying machine (75 g/m²) were printed out. An image density was evaluated according to the degree to which an image maintained its image density at the time of completion of printing as compared to an initial image. The relative density of a white portion having an original density of 0.00 with respect to a printed-out image was measured by using a Macbeth reflection densitometer (manufactured by Macbeth), and was used for evaluation.

⊚: Excellent (An image density at the time of completion is 1.40 or more.)

○: Good (An image density at the time of completion is 1.35 or more and less than 1.40.)

Δ: Acceptable (An image density at the time of completion is 1.00 or more and less than 1.35.)

×: Unacceptable (An image density at the time of completion is less than 1.00.)

2. Image Fogging

A predetermined number of sheets of ordinary plain paper for a copying machine (75 g/m²) were printed out. A solid white image at the time of completion of printing was evaluated for image fogging. To be specific, the image was evaluated for image fogging by means of the following method. The worst value of a white portion reflection density after printing and an average reflection density of paper before printing measured by using a reflection densitometer (manufactured by TOKYO DENSHOKU CO., LTD, REFLECTO-METER ODEL TC-6DS) were represented by Ds and Dr, respectively, and (Ds-Dr) was determined from These values. The resultant value was defined as a fogging amount (level), and was evaluated according to the following criteria.

⊚: Very good (A fogging amount is 0% or more and less than 1.5%.)

○: Good (A fogging amount is 1.5% or more and less than 3.0%.)

Δ: Practicable (A fogging amount is 3.0% or more and less than 5.0%.)

×: Not practicable (A fogging amount is 5.0% or more.)

3. Transferability

Solid black images were printed out on a predetermined number of sheets of ordinary plain paper for a copying machine (75 g/m²). The image omission amount of an image at the time of completion of printing was visually inspected, and was evaluated according to the following criteria.

⊚: Very good (Nearly no omission occurs)

○: Good (Omission slightly occurs)

Δ: Practicable

×: Not practicable

In addition, in each of Examples 31 to 36 and Comparative Examples 7 to 12, the occurrence sates of: flaws on the surfaces of the photosensitive drum and the intermediate transfer member; and fixing of residual toner to the surfaces, and influences of the flaws and the residual toner on a printed-out image (matching with an image forming apparatus) when 5,000 images were output were visually evaluated. In a system using each of the two-component developers of Examples 31 to 36, neither flaws on the surfaces of the photosensitive drum and the intermediate transfer member nor fixing of the toner to the surfaces was inspected, so matching with the image forming apparatus was very good. On the other hand, in a system using each of the two-component developers of Comparative Examples 7 to 12, fixing of the toner to the surface of the photosensitive drum was inspected. Furthermore, in the system using each of the two-component developers of Comparative Examples 7 to 12, fixing of the toner to the surface of the intermediate transfer member and a flaw on the surface were inspected. A problem in matching with the image forming apparatus such as the occurrence of a vertical stripe-like image defect on an image was raised.

TABLE 2

| Example | Two-component developer | Normal temperature and normal humidity | | | High temperature and high humidity | | |
|---|---|---|---|---|---|---|---|
| | | Image density | Image fogging | Transferability | Image density | Image fogging | Transferability |
| 31 | Blue 1 | ⊚ | ⊚ | ⊚ | ⊚ | ⊚ | ⊚ |
| 32 | Yellow 1 | ⊚ | ⊚ | ⊚ | ⊚ | ⊚ | ○ |
| 33 | Black 1 | ⊚ | ⊚ | ⊚ | ⊚ | ⊚ | ⊚ |
| 34 | Red 1 | ⊚ | ⊚ | ⊚ | ⊚ | ⊚ | ⊚ |
| 35 | Black 7 | ⊚ | ⊚ | ⊚ | ⊚ | ⊚ | ⊚ |
| 36 | Black 13 | ⊚ | ⊚ | ⊚ | ⊚ | ⊚ | ⊚ |
| Comparative example 7 | Blue 6 | X | X | X | X | X | X |
| 8 | Yellow 6 | X | X | X | X | X | X |
| 9 | Black 6 | Δ | Δ | X | Δ | X | X |
| 10 | Magenta 6 | Δ | Δ | X | Δ | X | X |
| 11 | Black 12 | Δ | Δ | X | X | X | X |
| 12 | Black 18 | Δ | Δ | X | Δ | X | X |

Examples 37 to 39 and Comparative Examples 13 to 15

Figure 3:
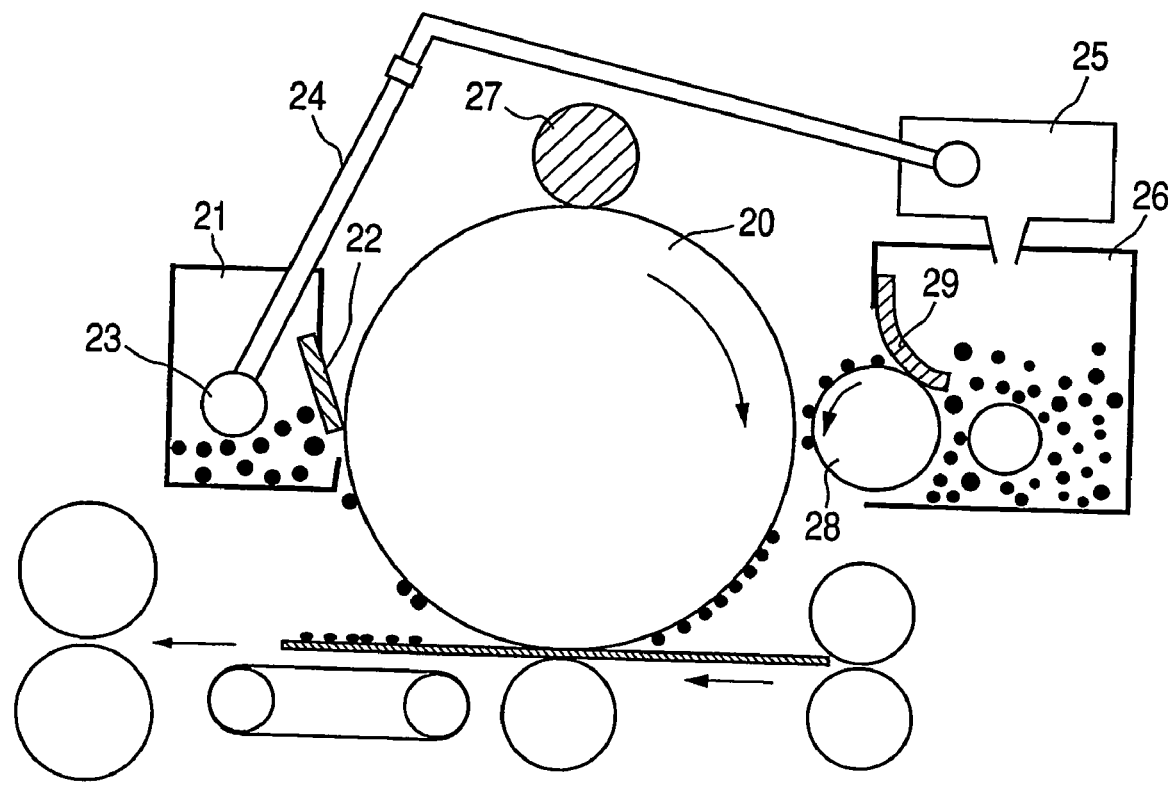
FIG. 3 is a schematic view for explaining an image forming apparatus having a toner reuse mechanism used in each of Examples 37 to 39 and Comparative Examples 13 to 15.

In performing an image forming method of each of Examples 37 to 39 and Comparative Examples 13 to 15, each of the toners produced in Examples 1, 6, and 11 and Comparative Examples 1 to 3 was used as a developer. As means for forming an image, an image forming apparatus modified by providing a reuse mechanism for a commercially available laser beam printer LBP-EX (manufactured by Canon Inc.) as shown in FIG. 3, was used. That is, the image forming apparatus shown in FIG. 3 is provided with a system which performs: scraping not transferred toner remaining on a photosensitive drum 20 after transfer by using an elastic blade 22 of a cleaner 21 brought into abutment with the photosensitive drum 20; sending the scraped toner to the inside of the cleaner 21 by using a cleaner roller; returning the toner to a developing unit 26 by using a supply pipe 24 provided with a conveyance screw through a cleaner reuse 23 and a hopper 25; and recycling the recovered toner.

In the image forming apparatus shown in FIG. 3, the surface of the photosensitive drum 20 is charged by a primary charging roller 27. A rubber roller with conductive carbon dispersed therein, coated with a nylon resin (having a diameter of 12 mm and an abutment pressure of 50 gf/cm) was used as the primary charging roller 27. An electrostatic latent image having a dark-area potential VD of −700 V and a light-area potential VL of −200 V was formed on the electrostatic latent image-bearing member (the photosensitive member 20) through laser exposure (600 dpi, not shown). As a toner-carrying member, a developing sleeve 28 having a surface roughness Ra of 1.1 whose surface was coated with a resin with carbon black dispersed therein was used. In FIG. 3, reference numeral 29 denotes a blade.

Figure 4:
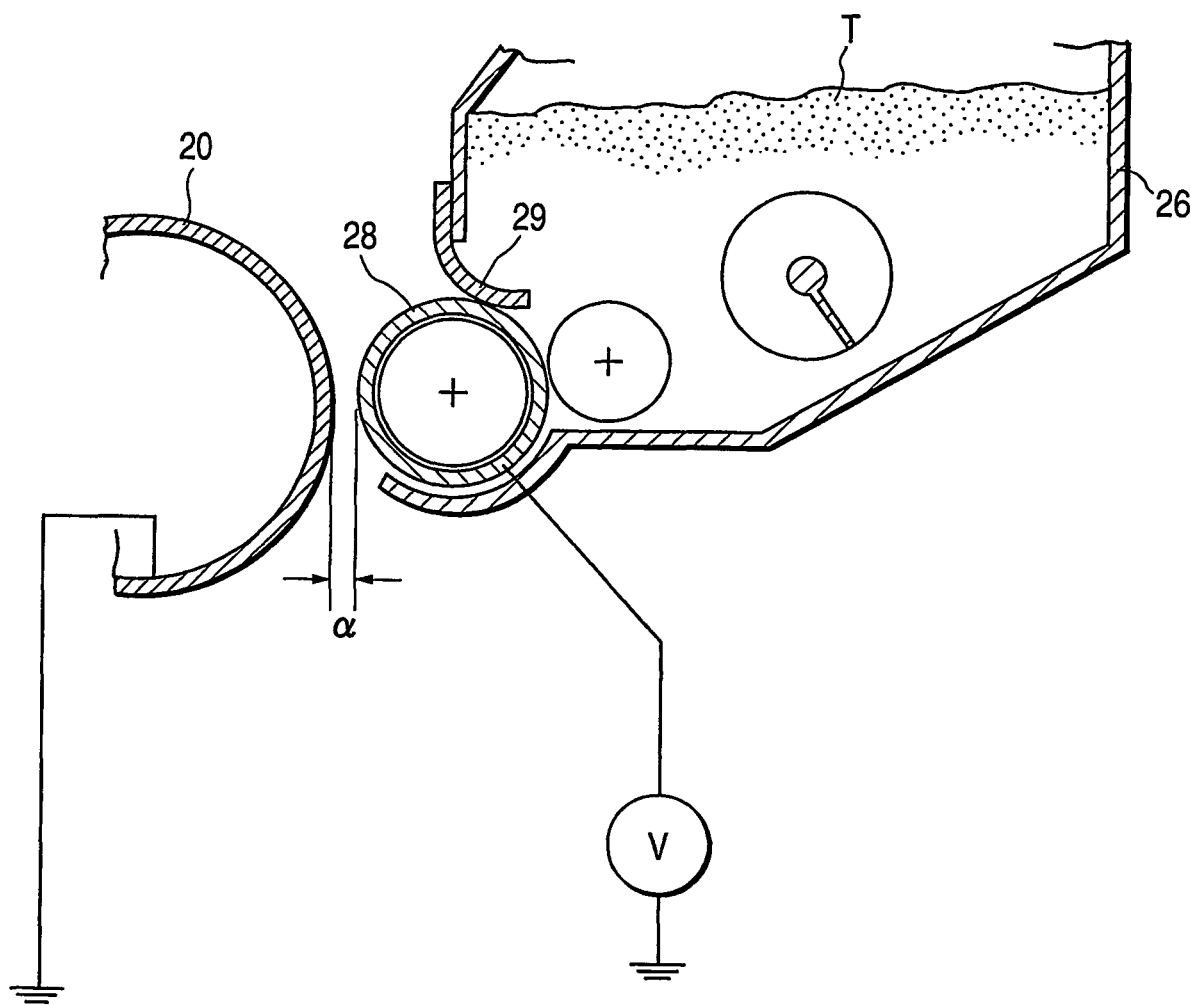
FIG. 4 is a sectional view of a main part of a developing device for a one-component developer used in each of Examples 37 to 39 and Comparative Examples 13 to 15.

FIG. 4 shows an enlarged sectional view of the main part of a developing device for a one-component developer used in each of Examples 37 to 39 and Comparative Examples 13 to 15. As for conditions for developing an electrostatic latent image, the speed of the developing sleeve 28 was set to be 1.1 times as high as the travelling speed of the surface of the photosensitive drum 20; and an interval a between the photosensitive drum 20 and the developing sleeve 28 (between S-D) to be 270 μm. A blade 29 made of urethane rubber was used as a member for regulating the thickness of a layer of toner (T) while abutting against the surface of the photosensitive member. The temperature of a heat-fixing device for fixing a toner image was set to be 160° C. A fixing device shown in each of FIG. 5 and FIG. 6 was used as the fixing device.

In FIG. 5, reference numeral 30 denotes a stay; 33, a heating roller; 34, a coil spring; 35, a film edge regulating flange; and 36, a feeder connector.

In FIG. 6, reference numeral 30 denotes a stay; 31, a heating member; 31a, a heater substrate; 31b, a heat generator; 31c, a surface protection layer; 31d, a thermometer element; 32, a fixation film; 33, a heating roller; 38, an inlet guide; and 39, an outlet guide (separation guide).

Under the above conditions, up to 30,000 sheets were printed out in a continuous mode (that is, a mode in which deterioration in toner is accelerated without suspension of a developing unit) in a normal-temperature-and-normal-humidity (25° C., 60% RH) environment at a print out rate of 8 sheets (A4 size)/min while toner was sequentially supplied. The image density of the resultant printed-out image was measured, and the image was evaluated for durability according to the following criteria. In addition, an image printed out on the 10,000th sheet was inspected and evaluated for image fogging according to the following criteria. At the same time, the state of each device constituting an image forming apparatus after the durability test was inspected to evaluate matching between each device and each of the above toners. Table 3 summarizes the evaluation results.

(Transition of Image Density in Durability Test)

A predetermined number of sheets of ordinary plain paper for a copying machine (75 g/m$^2$) were printed out. An image density was evaluated according to the degree to which an image maintained its image density at the time of completion of printing as compared to an image at the initial stage. The relative density of a white portion having an original density of 0.00 with respect to a printed-out image was measured by using a Macbeth reflection densitometer (manufactured by Macbeth), and was used for evaluation.

⊚: Excellent (An image density at the time of completion is 1.40 or more.)

○: Good (An image density at the time of completion is 1.35 or more and less than 1.40.)

Δ: Acceptable (An image density at the time of completion is 1.00 or more and less than 1.35.)

x: Unacceptable (An image density at the time of completion is less than 1.00.)

(Image Fogging)

A predetermined number of sheets of ordinary plain paper for a copying machine (75 g/m$^2$) were printed out. A solid white image at the time of completion of printing was evaluated for image fogging. To be specific, the image was evaluated for image fogging by means of the following method.

The worst value of a white portion reflection density after printing and an average reflection density of paper before printing measured by using a reflection densitometer (manufactured by TOKYO DENSHOKU CO., LTD, REFLECTO-METER ODEL TC-6DS) were represented by Ds and Dr, respectively, and (Ds-Dr) was determined from these values. The resultant value was defined as a fogging amount, and was evaluated according to the following criteria.

⊚: Very good (A fogging amount is 0% or more and less than 1.5%.)
○: Good (A fogging amount is 1.5% or more and less than 3.0%.)
Δ: Practicable (A fogging amount is 3.0% or more and less than 5.0%.)
x: Not practicable (A fogging amount is 5.0% or more.)

(1) Surface Properties
The occurrence states of flaws or scratches on the fixation film surface after the completion of the print out test were visually inspected and evaluated.
⊚: Very good (No occurrence)
○: Good (Nearly no occurrence)
Δ: Practicable
x: Not practicable (2) Fixing State of Residual Toner
The fixing state of residual toner on the surface of a fixation film after the completion of the print out test was visually inspected and evaluated.
⊚: Very good (No occurrence)
○: Good (Nearly no occurrence)
Δ: Practicable
x: Not practicable

TABLE 3

| | | Printed-out image evaluation | | | | | Evaluation of matching with each device | | | |
| | | Transition of image density at the time of duration | | | | Image fogging | | | Fixing device | |
| Example | Toner | Initial | 1,000 sheets | 10,000 sheets | 30,000 sheets | 10,000 sheets | Developing sleeve | Photosensitive drum | Surface property | Toner fixing |
|---|---|---|---|---|---|---|---|---|---|---|
| 37 | Blue 1 | ⊚ | ⊚ | ⊚ | ⊚ | ⊚ | ⊚ | ⊚ | ⊚ | ⊚ |
| 38 | Yellow 1 | ⊚ | ⊚ | ⊚ | ⊚ | ⊚ | ⊚ | ⊚ | ⊚ | ⊚ |
| 39 | Black 1 | ⊚ | ⊚ | ⊚ | ⊚ | ⊚ | ⊚ | ⊚ | ⊚ | ⊚ |
| Comparative example 13 | Blue 6 | Δ | X | X | X | X | X | X | X | X |
| 14 | Yellow 6 | Δ | X | X | X | X | X | X | X | X |
| 15 | Black 6 | ○ | Δ | X | X | X | X | X | X | X |

(Image Forming Apparatus Matching Evaluation)

1. Matching with Developing Sleeve
After the completion of the print out test, the fixing state of residual toner to the surface of a developing sleeve and an influence of the residual toner on a printed-out image were visually evaluated.
⊚: Very good (No fixing occurs.)
○: Good (Nearly no fixing occurs.)
Δ: Practicable (Fixing occurs, but affects an image little.)
x: Not practicable (Fixing is remarkable, and causes image unevenness.)

2. Matching with Photosensitive Drum
The occurrence states of: flaws on the surface of a photosensitive drum; and fixing of residual toner to the surface, and influences of the flaws and the residual toner on a printed-out image were visually evaluated.
⊚: Very good (Neither flaw nor fixing occurs)
○: Good (Flaws slightly occur, but does not affect an image.)
Δ: Practicable (Fixing and flaws occur, but have not much influence on an image.)
x: Not practicable (Fixing is remarkable, and causes vertical stripe-like image defects.)

3. Matching with Fixing Device
The state of the fixation film surface was observed, and the results of surface properties and the fixing state of residual toner were generally averaged to evaluate durability.

Example 40

A print out test was performed in a continuous mode (that is, a mode in which consumption of toner is accelerated without suspension of a developing unit) while the blue toner (1) of Example 1 was sequentially supplied in the same manner as in Example 37 except that: the toner reuse mechanism of the image forming apparatus shown in FIG. 3 was removed; and the print out rate was changed to 16 sheets (A4 size)/min. The resultant printed-out image and matching with an image forming apparatus were evaluated for the same items as those of Examples 37 to 39 and Comparative Examples 13 to 15. As a result, good results were obtained for all of the items.

INDUSTRIAL APPLICABILITY

The polymer according to the present invention can be applied to, for example, a charge control agent in toner used for electrophotography.

This application claims priority from Japanese Patent Application No. 2004-142882 filed on May 12, 2004, which is hereby incorporated by reference herein.

The invention claimed is:
1. A charge control agent for controlling a charged state of powder, which contains a polymer having a unit having a structure represented by the chemical formula (6):

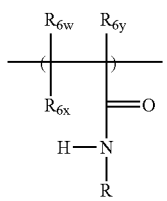
(6)

wherein R represents $-A_6-SO_2R_6$; $R_{6w}$ and $R_{6x}$ each represent a hydrogen atom, and $R_{6y}$ represents a $CH_3$ group or a hydrogen atom; $A_6$ represents a branched alkylene group having 4 carbon atoms represented by the chemical formula (406); $R_6$ represents a halogen atom or $OR_{6a}$ where $R_{6a}$ represents a linear or branched alkyl group having 3 carbon atoms, a branched alkyl group having 4 carbon atoms, a linear or branched alkyl group having 5 to 8 carbon atoms, or a substituted or unsubstituted phenyl group:

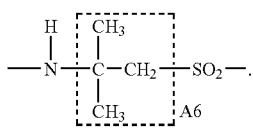
(406)

2. A charge control agent for controlling a charged state of powder, which contains a polymer having a unit having a structure represented by the chemical formula (7):

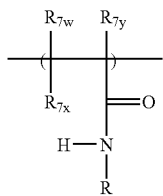
(7)

wherein R represents $-A_7-SO_2R_7$; $R_{7w}$ and $R_{7x}$ each represent a hydrogen atom, and $R_{7y}$ represents a $CH_3$ group or a hydrogen atom; $A_7$ represents a branched alkylene group having 4 carbon atoms represented by the chemical formula (407); $R_7$ represents a halogen atom or $OR_{7a}$ where $R_{7a}$ represents a linear or branched alkyl group having 2 to 8 carbon atoms, or a substituted or unsubstituted phenyl group:

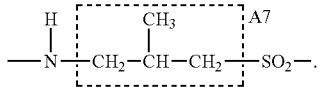
(407)

3. A charge control agent for controlling a charged state of powder, which contains a polymer having a unit having a structure represented by the chemical formula (507):

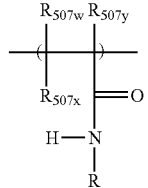
(507)

wherein R represents $-A_{507}-SO_2R_{507}$; $R_{507w}$ and $R_{507x}$ each represent a hydrogen atom, and $R_{507y}$ represents a $CH_3$ group or a hydrogen atom; $A_{507}$ represents a substituted heterocyclic structure; $R_{507}$ represents OH, a halogen atom, ONa, OK, or $OR_{507a}$ where $R_{507a}$ represents a linear or branched alkyl group having 1 to 8 carbon atoms, or a substituted or unsubstituted phenyl group.

4. A charge control agent for controlling a charged state of powder, which contains a polymer having a unit having a structure represented by the chemical formula (509a) or (509b):

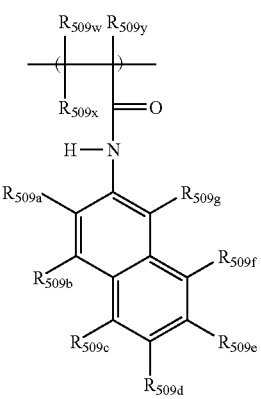
(509a)

wherein $R_{509w}$ and $R_{509x}$ each represent a hydrogen atom, and $R_{509y}$ represents a $CH_3$ group or a hydrogen atom; one of $R_{509a}$, $R_{509b}$, $R_{509c}$, $R_{509d}$, $R_{509e}$, $R_{509f}$, and $R_{509g}$ represents $SO_2R_{509o}$ ($R_{509o}$ represents a halogen atom or $OR_{509s}$, where $R_{509s}$ represents a linear or branched alkyl group having 1 to 8 carbon atoms, or a substituted or unsubstituted phenyl group); the others represent hydrogen atoms;

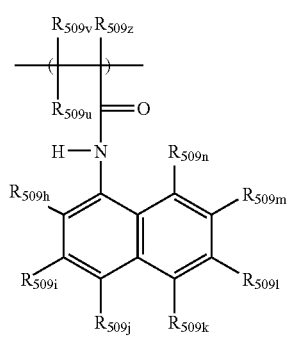
(509b)

wherein $R_{509v}$ and $R_{509u}$ each represent a hydrogen atom, and $R_{509z}$ represents a $CH_3$ group or a hydrogen atom; one of $R_{509h}$, $R_{509i}$, $R_{509j}$, $R_{509k}$, $R_{509l}$, $R_{509m}$, and $R_{509n}$ represents $SO_2R_{509q}$ ($R_{509q}$ represents a halogen atom or $OR_{509t}$ where $R_{509t}$ represents a linear or branched alkyl group having 1 to 8 carbon atoms, or a substituted or unsubstituted phenyl group); the others represent hydrogen atoms.

5. A charge control agent for controlling a charged state of powder, which contains a polymer having a unit having a structure represented by the chemical formula (9a) or (9b):

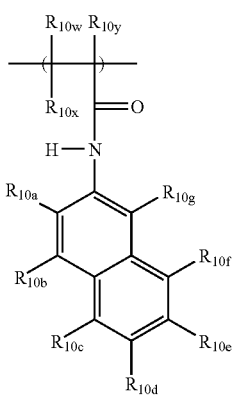

(9a)

wherein $R_{10w}$ and $R_{10x}$ each represents a hydrogen atom, and $R_{10y}$ represents a $CH_3$ group or a hydrogen atom; at least one of $R_{10a}$, $R_{10b}$, $R_{10c}$, $R_{10d}$, $R_{10e}$, $R_{10f}$ and $R_{10g}$ represents $SO_2R_{10o}$; $R_{10o}$ represents OH, a halogen atom, ONa, OK, or $OR_{10s}$; $R_{10s}$ represents a linear or branched alkyl group having 1 to 8 carbon atoms, or a substituted or unsubstituted phenyl group; each of $R_{10a}$, $R_{10b}$, $R_{10c}$, $R_{10d}$, $R_{10e}$, $R_{10f}$ and $R_{10g}$ is selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{10p}$, an acetamide group, an OPh group, an NHPh group, a $CF_3$ group, a $C_2F_5$ group, and a $C_3F_7$ group; $R_{10p}$ represents an H atom, an Na atom, or a K atom; up to five of $R_{10a}$, $R_{10b}$, $R_{10c}$, $R_{10d}$, $R_{10e}$, $R_{10f}$ and $R_{10g}$ can represent hydrogen atoms;

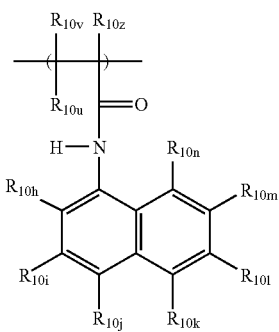

(9b)

wherein $R_{10v}$ and $R_{10u}$ each represent a hydrogen atom, and $R_{10z}$ represents a $CH_3$ group or a hydrogen atom; at least one of $R_{10h}$, $R_{10i}$, $R_{10j}$, $R_{10k}$, $R_{10l}$, $R_{10m}$, and $R_{10n}$ represents $SO_2R_{10q}$; $R_{10q}$ represents OH, a halogen atom, ONa, OK, or $OR_{10t}$; $R_{10t}$ represents a linear or branched alkyl group having 1 to 8 carbon atoms, or a substituted or unsubstituted phenyl group; each of $R_{10h}$, $R_{10i}$, $R_{10j}$, $R_{10k}$, $R_{10l}$, $R_{10m}$, and $R_{10n}$ is selected from a hydrogen atom, a halogen atom, an alkyl group having 1 to 20 carbon atoms, an alkoxy group having 1 to 20 carbon atoms, an OH group, an $NH_2$ group, an $NO_2$ group, $COOR_{10r}$, an acetamide group, an OPh group, an NHPh group, a $CF_3$ group, a $C_2F_5$ group, and a $C_3F_7$ group; $R_{10r}$ represents an H atom, an Na atom, or a K atom; up to five of $R_{10h}$, $R_{10i}$, $R_{10j}$, $R_{10k}$, $R_{10l}$, $R_{10m}$, and $R_{10n}$ can represent hydrogen atoms.

6. A charge control agent for controlling a charged state of powder, which contains a polymer having a unit having a structure represented by the chemical formula (10):

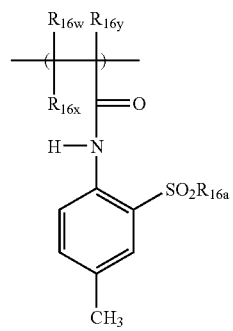

(10)

wherein $R_{16w}$ and $R_{16x}$ each represent a hydrogen atom, and $R_{16y}$ represents a $CH_3$ group or a hydrogen atom; $R_{16a}$ represents OH, a halogen atom, ONa, OK, or $OR_{16b}$ where $R_{16b}$ represents a linear or branched alkyl group having 1 to 8 carbon atoms, or a substituted or unsubstituted phenyl group.

7. A charge control agent for controlling a charged state of powder, which contains a polymer having a unit having a structure represented by the chemical formula (12):

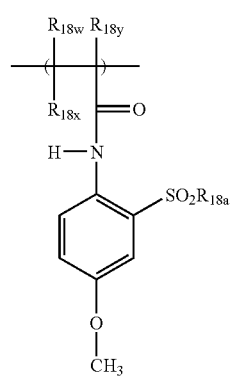

(12)

wherein $R_{10w}$ and $R_{18x}$ each represent a hydrogen atom, and $R_{18y}$ represents a $CH_3$ group or a hydrogen atom; $R_{18a}$ represents OH, a halogen atom, ONa, OK, or $OR_{18b}$ where $R_{18b}$ represents a linear or branched alkyl group having 1 to 8 carbon atoms, or a substituted or unsubstituted phenyl group.

8. A charge control agent for controlling a charged state of powder, which contains a polymer having a unit having a structure represented by the chemical formula (301):

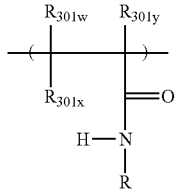

(301)

wherein R represents $-A_{301}-SO_2R_{301}$; $R_{301w}$ and $R_{301x}$ each independently represent a halogen atom or a hydrogen atom, and $R_{301y}$ represents a $CH_3$ group, a halogen atom, or a hydrogen atom; at least one of $R_{301w}$, $R_{301x}$, and $R_{301y}$ represents a halogen atom; $A_{301}$ represents a substituted or unsubstituted aliphatic hydrocarbon structure, a substituted or unsubstituted aromatic ring structure, or a substituted or unsubstituted heterocyclic structure; $R_{301}$ represents OH, a halogen atom, ONa, OK, or $OR_{301a}$ where $R_{3O1a}$ represents a linear or branched alkyl group having 1 to 8 carbon atoms, or a substituted or unsubstituted phenyl group.

9. A charge control agent according to claim 1, which further contains at least one unit derived from a vinyl-based monomer represented by chemical formula (108) in addition to the unit represented by the chemical formula (6):

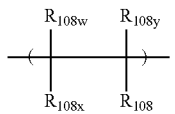

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, $-CO-R_{108a}$, $-O-R_{108b}$, $-COO-R_{108c}$, $-OCO-R_{108d}$, $-CONR_{108e}R_{108f}$, $-CN$, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

10. A charge control agent according to claim 2, which further contains at least one unit derived from a vinyl-based monomer represented by chemical formula (108) in addition to the unit represented by the chemical formula (7):

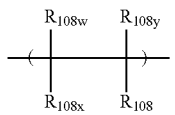

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, $-CO-R_{108a}$, $-O-R_{108b}$, $-COO-R_{108c}$, $-OCO-R_{108d}$, $-CONR_{108e}R_{108f}$, $-CN$, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

11. A charge control agent according to claim 3, which further contains at least one unit derived from a vinyl-based monomer represented by chemical formula (108) in addition to the unit represented by the chemical formula (507):

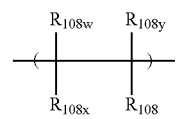

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, $-CO-R_{108a}$, $-O-R_{108b}$, $-COO-R_{108c}$, $-OCO-R_{108d}$, $-CONR_{108e}R_{108f}$, $-CN$, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

12. A charge control agent according to claim 4, which further contains at least one unit derived from a vinyl-based monomer represented by chemical formula (108) in addition to the unit represented by the chemical formula (509a) or (509b):

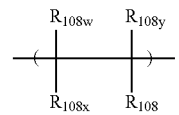

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, $-CO-R_{108a}$, $-O-R_{108b}$, $-COO-R_{108c}$, $-OCO-R_{108d}$, $-CONR_{108e}R_{108f}$, $-CN$, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

13. A charge control agent according to claim 5, which further contains at least one unit derived from a vinyl-based monomer represented by chemical formula (108) in addition to the unit represented by the chemical formula (9a) or (9b):

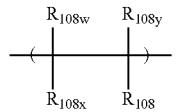

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{108a}$, —O—$R_{108b}$, —COO—$R_{108c}$, —OCO—$R_{108d}$, —CONR$_{108e}$R$_{108f}$, —CN, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

14. A charge control agent according to claim 6, which further contains at least one unit derived from a vinyl-based monomer represented by chemical formula (108) in addition to the unit represented by the chemical formula (10):

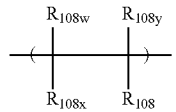

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{108a}$, —O—$R_{108b}$, —COO—$R_{108c}$, —OCO—$R_{108d}$, —CONR$_{108e}$R$_{108f}$, —CN, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

15. A charge control agent according to claim 7, which further contains at least one unit derived from a vinyl-based monomer represented by chemical formula (108) in addition to the unit represented by the chemical formula (12):

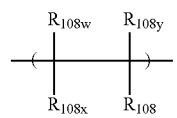

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{108a}$, —O—$R_{108b}$, —COO—$R_{108c}$, —OCO—$R_{108d}$, —CONR$_{108e}$R$_{108f}$, —CN, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

16. A charge control agent according to claim 8, which further contains at least one unit derived from a vinyl-based monomer represented by chemical formula (108) in addition to the unit represented by the chemical formula (301):

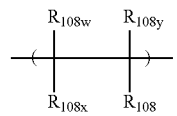

(108)

wherein $R_{108w}$ and $R_{108x}$ each independently represent a halogen atom or a hydrogen atom, and $R_{108y}$ represents a $CH_3$ group, a halogen atom, or a hydrogen atom; $R_{108}$ represents a hydrogen atom, a substituted or unsubstituted aliphatic hydrocarbon structure, a substituted or unsubstituted aromatic ring structure, a substituted or unsubstituted heterocyclic structure, a halogen atom, —CO—$R_{108a}$, —O—$R_{108b}$, —COO—$R_{108c}$, —OCO—$R_{108d}$, —CONR$_{108e}$R$_{108f}$, —CN, or a ring structure containing an N atom; $R_{108a}$, $R_{108b}$, $R_{108c}$, $R_{108d}$, $R_{108e}$, and $R_{108f}$ each independently represent a hydrogen atom, a substituted or unsubstituted aliphatic hydrocarbon structure, a substituted or unsubstituted aromatic ring structure, or a substituted or unsubstituted heterocyclic structure.

* * * * *